US006274327B1

(12) United States Patent
Hiles et al.

(10) Patent No.: US 6,274,327 B1
(45) Date of Patent: Aug. 14, 2001

(54) POLYPEPTIDES HAVING KINASE ACTIVITY, THEIR PREPARATION AND USE

(75) Inventors: Ian D. Hiles; Michael J. Fry; Ritu Dhand; Michael D. Waterfield; Peter J. Parker; Masayuki Otsu; George Panayoutou; Stefano Volinia; Ivan Gout, all of London (GB)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/085,957

(22) Filed: May 27, 1998

Related U.S. Application Data

(62) Division of application No. 08/780,872, filed on Jan. 9, 1997, now Pat. No. 5,846,824, which is a division of application No. 08/162,081, filed as application No. PCT/GB93/00761 on Apr. 13, 1993, now Pat. No. 5,824,492.

(30) Foreign Application Priority Data

Apr. 13, 1992 (GB) .................................................. 9208135

(51) Int. Cl.[7] .............................. G01N 33/53; C12Q 1/68; C12Q 1/48; C12Q 1/42
(52) U.S. Cl. .................................. 435/7.1; 435/6; 435/7.1; 435/7.2; 435/7.8; 435/15; 435/21; 435/69.1; 435/69.2; 435/194; 435/252.3; 435/348; 514/263; 530/350
(58) Field of Search .................................. 435/6, 7.1, 7.2, 435/7.8, 15, 21, 69.2, 69.1, 194, 252.3, 348; 514/263; 530/350

(56) References Cited

PUBLICATIONS

Carpenter et al. 1990. Purification and Characterization of Phopoinositide 3–Kinase from Rat Liver. J. of Biol. Chem. 265 (32): 19704–19711.*
Escobedo et al. 1991. cDNA Cloning of a Novel 85 kd Protein That Has SH2 Domians and Regulates Binding of P13–Kinase to the PDGF Beta–Receptor. Cell. 65: 75–82.*
Escobedo et al. 1991. A Phosphatidylinositol–3 Kinase Binds to Platelet–Derived growth Factor Receptors through a Specfic Receptor Sequence Containing Phosphotyrosine. Mol. Cell. Bio. 11 (2):1125–1132.*
Otsu et al. 1991. Characterization of Two 85 kd Proteins That Associate with Receptor Tyrosine Kinases, Middle–T/pp60 c–src Complexes, and P13–Kinase. 65: 91–104.*
Shibasaki et al. 1991. Two Types of Phosphatidylinositol 3–Kinase from Bovine Thymus. J. Bio. Chem. 266: 8108–8114.*
Maurer et al. 1980. Methods of Enzymology. Academic Press, Inc. pp. 49–70.*
Harlow et al. 1988. Antibodes: A laboratory Manual. Cold Spring Harbor Labs. New York.*

* cited by examiner

*Primary Examiner*—James C. Housel
*Assistant Examiner*—Ja-Na A. Hines

(57) ABSTRACT

This invention relates to new polypeptides which exhibit kinase activity or, more specifically, which show phosphoinositide (PI) 3-kinase activity. Such polypeptides are involved in pathways responsible for cellular growth and differentiation. An isolated polypeptide which possesses PI3-kinase activity when produced by recombinant production in insect cells is disclosed.

10 Claims, 76 Drawing Sheets

FIG. 2A 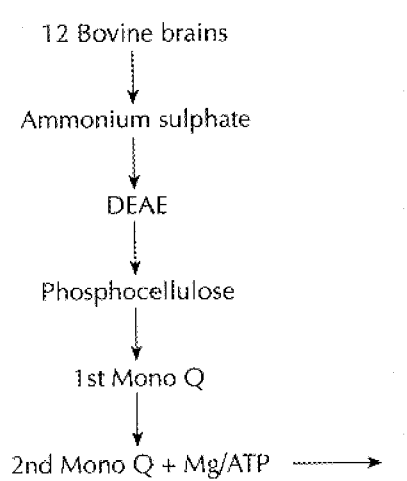 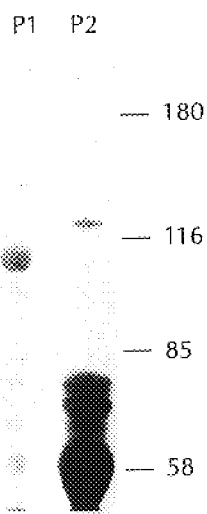

FIG. 4A 1 2 3 4 5 6 7

—180

—116

—84

—58 anti-ALPHA

FIG. 4B 1 2 3 4 5 6 7

—180

—116

—84

—58 anti-BETA

—180

—116

—85

—58

Figure 1A:
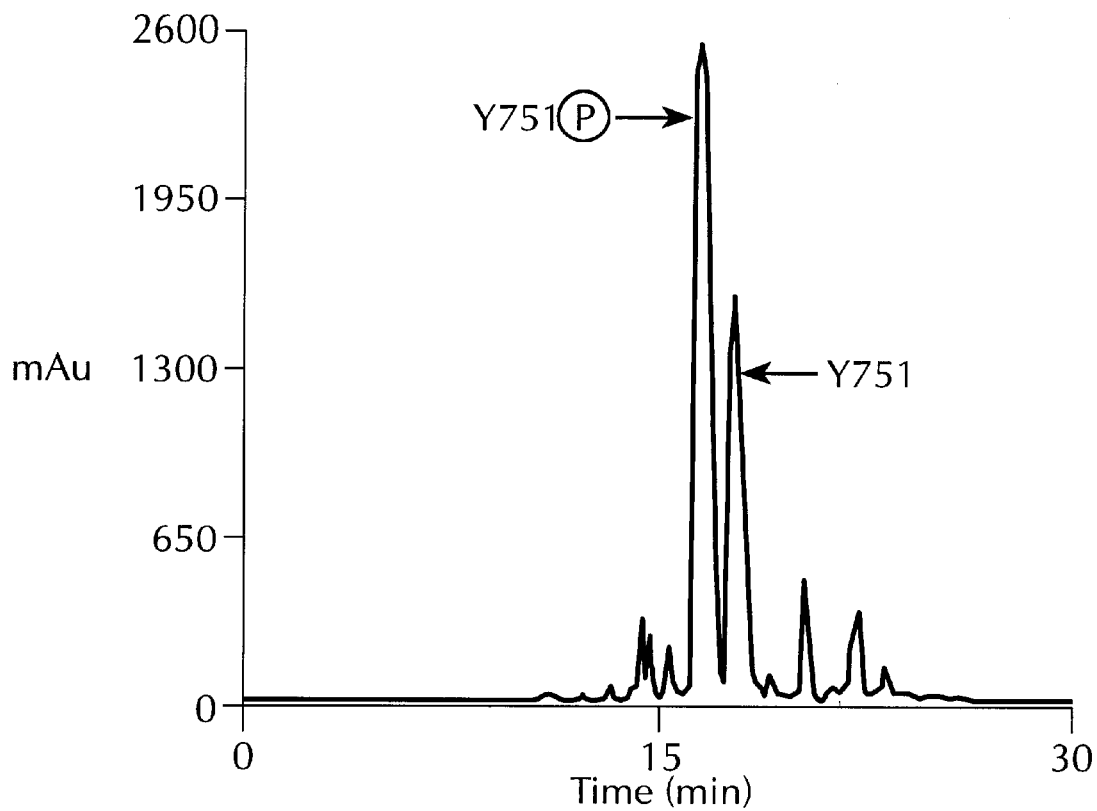
Figure 1B:
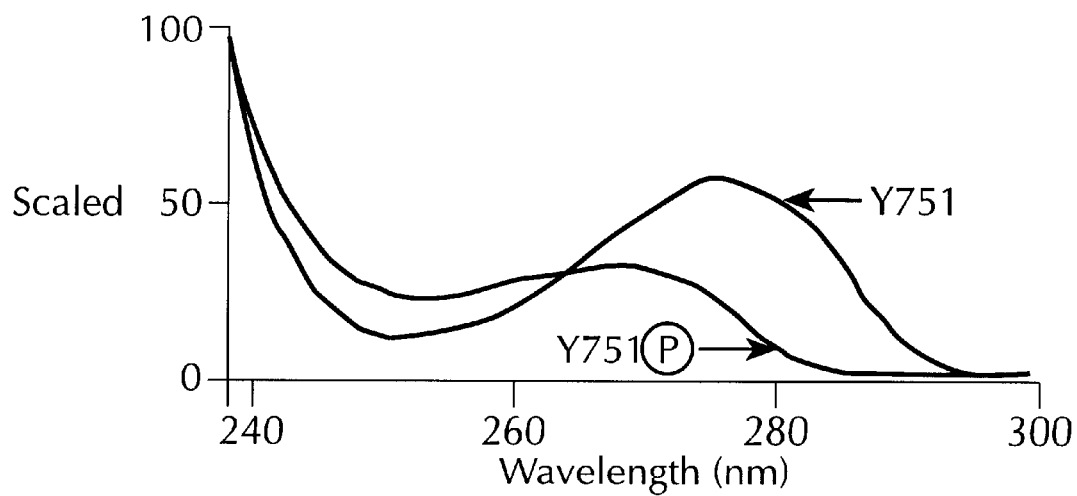

```
C   Y   Y   Y   pG  Y   Y
O   7   7   8   A   4   5
N   5   5   5   T   1   2
    1   1   7       6   7
        S
```

— PI3P

— Ori

```
C   Y   Y   Y   pG  Y   Y
O   7   7   8   A   4   5
N   5   5   5   T   1   2
    1   1   7       6   7
        S
```

```
751         D M S K D E S V D Y V P M L D M K
751.S             C D E S V D Y V P M L
740               G E S D G G Y M D M S K
1313        E F C P D P L Y E V M L K

Consensus         E E E E Y M P M X X
                  D D D D D   V
```

FIG. 9A

```
  M   P   P   R   P   S   S   G   E   L   W   G   I   H   L   M       16
ATGCCTCCAAGACCATCATCAGGTGAACTGTGGGGCATCCACTTGATG                      48

P   P   R   I   L   V   E   C   L   L   P   N   G   M   I   V       32
CCCCCAAGAATCCTAGTAGAATGTTTACTACCAAATGGATGATAGTG                       96

T   L   E   C   L   R   E   A   T   L   I   T   I   K   H   E       48
ACTTTAGAATGCCTCCGTGAGGCTACGTTAATAACGATAAAGCATGAA                     144

L   F   K   E   A   R   K   Y   P   L   H   Q   L   L   Q   D       64
CTATTTAAAGAAGCAAGAAAATACCCTCTCCATCAACTTCTTCAAGAT                     192

E   S   S   Y   I   F   V   S   V   T   Q   E   A   E   R   E       80
GAATCTTCTTACATTTTCGTAAGTGTTACCCAAGAAGCAGAAAGGGAA                     240

E   F   F   D   E   T   R   R   L   C   D   L   R   L   F   Q       96
GAATTTTTTGATGAAACAAGACGACTTTGTGACCTTCGGCTTTTTCAA                     288

P   F   L   K   V   I   E   P   V   G   N   R   E   E   K   I      112
CCCTTTTTAAAAGTAATTGAACCAGTAGGCAACCGTGAAGAAAAGATC                     336

L   N   R   E   I   G   F   A   I   G   M   P   V   C   E   F      128
CTCAATCGAGAAATTGGTTTTGCTATCGGCATGCCAGTGTGTGAATTC                     384

D   M   V   K   D   P   E   V   Q   D   F   R   R   N   I   L      144
GATATGGTTAAAGATCCAGAAGTACAGGACTTCCGAAGAAATATTCTC                     432
```

FIG. 9B

```
  N   V   C   K   E   A   V   D   L   R   D   L   N   S   P   H       160
AATGTTTGTAAAGAAGCTGTGGATCTTAGGGATCTTAATTCACCTCAT                      480
                         A
  S   R   A   M   Y   V   Y   P   P   N   V   E   S   S   P   E       176
AGTAGAGCAATGTATGTTTATCCTCCAAATGTAGAATCTTCACCAGAA                      528

L   P   K   H   I   Y   N   K   L   D   K   G   Q   I   I   V       192
CTGCCAAAGCACATATATAATAAATTGGATAAAGGGCAAATAATAGTG                      576

V   I   W   V   I   V   S   P   N   N   D   K   Q   K   Y   T       208
GTGATTTGGGTAATAGTTTCTCCAAATAATGACAAACAGAAGTATACT                      624

L   K   I   N   H   D   C   V   P   E   Q   V   I   A   E   A       224
CTGAAAATCAACCATGACTGTGTGCCAGAACAAGTAATTGCTGAAGCA                      672

I   R   K   K   T   R   S   M   L   L   S   S   E   Q   L   K       240
ATCAGGAAAAAAACTCGAAGTATGTTGCTATCATCTGAACAACTAAAA                      720

L   C   V   L   E   Y   Q   G   K   Y   I   L   K   V   C   G       256
CTCTGTGTTTTAGAATATCAGGGCAAGTATATTTTAAAAGTGTGTGGA                      768

C   D   E   Y   F   L   E   K   Y   P   L   S   Q   Y   K   Y       272
TGTGATGAATACTTCCTAGAAAAATATCCTCTGAGTCAGTATAAGTAT                      816

I   R   S   C   I   M   L   G   R   M   P   N   L   M   L   M       288
ATAAGAAGCTGTATAATGCTTGGAGGATGCCCAATTTGATGCTGATG                       864
```

FIG. 9C

| | |
|---|---|
| A K E S L Y S Q L P M D C F T M | 304 |
| GCTAAAGAAAGCCTCTATTCTCAACTGCCAATGGACTGTTTTACAATG | 912 |
| | |
| P S Y S R R I S T A T P Y M N G | 320 |
| CCATCATATTCCAGACGCATCTCCACAGCTACGCCATATATGAATGGA | 960 |
| *B* | |
| E T S T K <u>S L W V I N S A L R I</u> | 336 |
| GAAACATCTACAAAATCCCTTTGGGTTATAAATAGTGCACTCAGAATA | 1008 |
| | |
| <u>K</u> I L C A T Y V N V I R D I D | 352 |
| AAAATTCTTTGTGCAACCTATGTGAATGTAAATATTCGAGACATTGAC | 1056 |
| | |
| K I Y V R T G I Y H G G E P L C | 368 |
| AAGATTTATGTTCGAACAGGTATCTACCATGGAGGAGAACCCTTATGT | 1104 |
| | |
| D N V N T Q R V P C S N P R W N | 384 |
| GATAATGTGAACACTCAAAGAGTACCTTGTTCCAATCCCAGGTGGAAT | 1152 |
| | |
| E W L N Y D I Y I P D L P R A A | 400 |
| GAATGGCTGAATTACGATATATACATTCCTGATCTTCCTCGTGCTGCT | 1200 |
| | |
| R L C L S I C S V K G R K G A K | 416 |
| CGACTTTGCCTTTCCATTTGTTCTGTTAAAGGCCGAAAGGGTGCTAAA | 1248 |
| | |
| E E H C P L A W G N I N L F D Y | 432 |
| GAGGAACACTGTCCATTGGCCTGGGGAAATATAAACTTGTTTGATTAC | 1296 |

FIG. 9D

```
  T   D   T   L   V   S   G   K   M   A   L   N   L   W   P   V      448
ACAGATACTCTAGTATCTGGAAAAATGGCTTTGAATCTTTGGCCAGTA                    1344
                                C
  P   H   G   L   E   D   L   L   N   P   I   G   V   T   G   S      464
CCTCATGGACTAGAAGATTTGCTGAACCCTATTGGTGTTACTGGATCA                    1392

N   P   N   K   E   T   P   C   L   E   L   E   F   D   W   F      480
AATCCAAATAAAGAAACTCCATGTTTAGAGTTGGAGTTTGACTGGTTC                    1440

S   S   V   V   K   F   P   D   M   S   V   I   E   E   H   A      496
AGCAGTGTGGTAAAGTTTCCAGATATGTCAGTGATTGAAGAGCATGCC                    1488

N   W   S   V   S   R   E   A   G   F   S   Y   S   H   A   G      512
AATTGGTCTGTATCCCGTGAAGCAGGATTTAGTTATTCCCATGCAGGA                    1536

L   S   N   R   L   A   R   D   N   E   L   R   E   N   D   K      528
CTGAGTAACAGACTAGCTAGAGACAATGAATTAAGAGAAAATGATAAA                    1584

E   Q   L   R   A   I   C   T   R   D   P   L   S   E   I   T      544
GAACAGCTCCGAGCAATTTGTACACGAGATCCTCTATCTGAAATCACT                    1632

E   Q   E   K   D   F   L   W   S   H   R   H   Y   C   V   T      560
GAGCAAGAGAAAGATTTTCTGTGGAGCCACAGACACTATTGTGTAACT                    1680

I   P   E   I   L   P   K   L   L   S   V   K   W   N   S          576
ATCCCCGAAATTCTACCCAAATTGCTTCTGTCTGTTAAATGGAACTCT                    1728
```

FIG. 9E

```
      R   D   E   V   A   Q   M   Y   C   L   V   K   D   W   P   P     592
     AGAGATGAAGTAGCTCAGATGTACTGCTTGGTAAAAGATTGGCCTCCA                  1776

I   K   P   E   Q   A   M   E   L   L   D   C   N   Y   P   D     608
     ATCAAGCCTGAACAGGCTATGGAGCTTCTGGACTGCAATTACCCAGAT                  1824

P   M   V   R   G   F   A   V   R   C   L   E   K   Y   L   T     624
     CCTATGGTTCGAGGTTTTGCTGTTCGGTGCTTAGAAAAATATTTAACA                  1872
                                                  D
      D   D   K   L   S   Q   Y   L   I   Q   L   V   Q   V   L   K     640
     GATGACAAACTTTCTCAGTACCTAATTCAGCTAGTACAGGTACTAAAA                  1920

Y   E   Q   Y   L   D   N   L   L   V   R   F   L   L   K   K     656
     TATGAACAGTATTTGGATAACCTGCTTGTGAGATTTTTACTCAAAAAA                  1968
                                 E
      A   L   T   N   Q   R   I   G   H   F   F   F   W   H   L   K     672
     GCGTTAACTAATCAAAGGATCGGTCACTTTTTCTTTTGGCATTTAAAA                  2016
                                                 F
      S   E   M   H   N   K   T   V   S   Q   R   F   G   L   L   L     688
     TCTGAGATGCACAATAAAACAGTTAGTCAGAGGTTTGGCCTGCTTTTG                  2064

E   S   Y   C   R   A   C   G   M   Y   L   K   H   L   N   R     704
     GAGTCCTATTGCCGTGCATGTGGGATGTATCTGAAGCACCTTAATAGG                  2112
                                                  G
      Q   V   E   A   M   E   K   L   I   N   L   T   D   I   L   K     720
     CAAGTTGAGGCTATGGAAAAGCTCATTAACTTGACTGACATTCTCAAA                  2160
```

FIG. 9F

```
  Q  E  K  K  D  E  T  Q  K  V  Q  M  K  F  L  V      736
CAAGAGAAGAAGGATGAAACACAAAAGGTACAGATGAAGTTTTTAGTT      2208

E  Q  M  R  R  P  D  F  M  D  A  L  Q  G  F  L      752
GAGCAAATGCGGCGACCAGATTTCATGGATGCTCTCCAGGGCTTTCTG      2256

S  P  L  N  P  A  H  Q  L  G  N  L  R  L  E  E      768
TCTCCTCTAAACCCTGCTCATCAGCTGGGAAATCTCAGGCTTGAAGAG      2304

C  R  I  M  S  S  A  K  R  P  L  W  L  N  W  E      784
TGTCGAATTATGTCTTCTGCAAAAAGGCCACTGTGGTTGAATTGGGAG      2352

N  P  D  I  M  S  E  L  L  F  Q  N  N  E  I  I      800
AACCCAGACATCATGTCAGAATTACTCTTTCAGAACAATGAGATCATC      2400

F  K  N  G  D  D  L  R  Q  D  M  L  T  L  Q  I      816
TTTAAAAATGGGGATGATTTACGGCAAGATATGCTAACCCTTCAGATT      2448

I  R  I  M  E  N  I  W  Q  N  Q  G  L  D  L  R      832
ATTCGCATTATGGAAAATATCTGGCAAAATCAAGGTCTTGATCTTCGA      2496

M  L  P  Y  G  C  L  S  I  G  D  C  V  G  L  I      848
ATGTTACCTTATGGATGTCTGTCAATCGGTGACTGTGTGGGACTTATC      2544

E  V  V  R  N  S  H  T  I  M  Q  I  Q  C  K  G      864
GAGGTGGTGAGAAATTCTCACACTATAATGCAGATTCAGTGTAAAGGA      2592
```

FIG. 9G

```
                          H
    G  L  K  G  A  L  Q  F  N  S  H  T  L  H  Q  W          880
GGCCTGAAAGGTGCACTGCAGTTTAACAGCCACACACTCCATCAGTGG            2640

L  K  D  K  N  K  G  E  I  Y  D  A  A  I  D  L          896
CTCAAAGACAAGAACAAGGGGGAAATATATGATGCGGCCATCGATTTG            2688
              I
    F  T  R  S  C  A  G  Y  C  V  A  T  F  I  L  G          912
TTTACACGATCATGTGCTGGATATTGTGTTGCCACCTTCATTTTGGGA            2736

I  G  D  R  H  N  S  N  I  M  V  K  D  D  G  Q          928
ATTGGAGATCGTCACAATAGTAATATCATGGTTAAAGATGATGGACAA            2784
                    J
    L  F  H  I  D  F  G  H  F  L  D  H  K  K  K             944
CTGTTTCATATAGATTTTGGACACTTTTTGGATCACAAGAAGAAAAAA            2832
                          K
    F  G  Y  K  R  E  R  V  P  F  V  L  T  Q  D  F          960
TTTGGTTATAAACGAGAGCGCGTGCCGTTTGTTTTGACACAAGATTTC            2880

L  I  V  I  S  K  G  A  Q  E  C  T  K  T  R  E          976
TTAATAGTGATTAGTAAAGGAGCCCAAGAATGCACAAAGACAAGAGAA            2928

F  E  R  F  Q  E  M  C  Y  K  A  Y  L  A  I  R          992
TTTGAGAGGTTTCAGGAGATGTGTTACAAGGCTTATCTAGCTATTCGG            2976
```

FIG. 9H

```
                               L
   Q  H  A  N  L  F  I  N  L  F  S  M  M  L  G  S     1008
  CAGCATGCCAATCTCTTCATAAATCTTTTCTCAATGATGCTTGGCTCT     3024

G  M  P  E  L  Q  S  F  D  D  I  A  Y  I  R  K     1024
  GGAATGCCAGAACTGCAATCTTTTGATGATATTGCATACATTCGAAAG     3072
                            M
   T  L  A  L  D  K  T  E  Q  E  A  L  E  Y  F  M     1040
  ACCCTAGCTTTAGATAAAACTGAGCAAGAGGCTTTGGAGTATTTCATG     3120

K  Q  M  N  D  A  H  H  G  G  W  T  T  K  M  D     1056
  AAACAAATGAATGATGCACACCATGGTGGCTGGACAACAAAAATGGAT     3168
              N
   W  I  F  H  T  I  K  Q  H  A  L  N  *              1069
  TGGATCTTCCACACAATTAAGCAGCATGCTTTGAACTGA              3207
```

FIG. 10B

```
P110      VCEFDMVKDPEVQDFRRNILNVCKEAVDLRDLNSPHSRAMYVYPPN 170
          ..|  :  .|  :|. :: .| .:  . .|:.  ..  ...: :...|
VPS34     NITFCVSQDLDVP.LKVKIKSLEGHKPLLKPSQKILNPELMLIGSN 49

171 VESSPEL..PKHIYNKLDKGQIIVVIWVIVSPNNDKQKYTLKINHDCVPE 218
       | .|.:|  . ::::|  . .:::.|:.   |  .:........:
    50 VFPSSDLIVSLQVFDKERNRNLTLPIYTPYIPFRNSRIWDYWL....... 92

219 QVIAEAIRKKTRSMLLSSEQLKLCVLEYQGKYILKVCGCDEYFLEKYPLS 268
       .:.  :.:  :  :||  :|::.::||.|
    93 .....TLPIRIKQLTFSS.HLRIILWEYNG.................... 116

269 QYKYIRSCIMLGRMPNLMLMAKESLYSQLPMDCFTMPSYSRRISTATPYM 318
                                              |...|::
   117 .......................................SKQIPFF 123

319 NGETSTKSLWVINSALRIKILCATYVNVNIRDIDKIYVRTGIYHGGEPLC 368
       | |||.  :  : ::.|:         |::::.: .| ::.. .|.:.
   124 NLETSI..FNLKDCTLK............RGFESLKFRYDVIDHCEVVT 158

369 DNVNTQRVPCSNPRWNEWLNYDIYIPDLPRAARLC.LSICSVKGRKGAKE 417
       || :       .| ||  ..:  .:::.|  ::|   :.|:..:  ::.:.
   159 DNKD..........QENLN.KYFQGEFTRLPWLDEITISKLRKQRENRT 196
```

FIG. 10C

```
418 .EHCPLAWG.NINLFDYTDTLVSGKMALNLWPVPHGLEDLLNPIGVTGS. 464
    .:....:. :: :::.. .::.. .:   :|   .| |  |:...
197 WPQGTFVLNLEFPMLELPVVFIEREIMNTQMNIP....TLKNNPGLSTDL 242

465 .NPNKETPCLELEF.DWFSSVVKFPDMSVIEEHANWSVSREAGFSYSHAG 512
    :||::.|  :.:.: |.: |.:|| |    .:::|  ..  |  ...:|:
243 REPNRNDPQIKISLGDKYHSTLKFYD....PDQPNNDPIEEKYRRLERAS 288

513 LSNRLARDNELRENDKEQLRAICTRDPLSEITEQEKDFLWSHRHYCVTIP 562
    ,..|.::.     ..:: |. |.. .|  ..:|.:||: :|..|.| :. .
289 KNANLDKQVKPDIKKRDYLNKIINYPPGTKLTAHEKGSIWKYRYYLMNNK 338

563 EILPKLLLSVKWNSRDEVAQMYCLVKDWPPIKPEQAMELLDCNYPDPMVR 612
    . |.||| |..:.. .|  .::. |:..|::|.  ::|:|||::.:.:  ||
339 KALTKLLQSTNLREESERVEVLELMDSWAEIDIDDALELLGSTFKNLSVR 388

613 GFAVRCLEKYLTDDKLSQYLIQLVQVLKYEQY.................. 644
    ::||.  |.|  .|..|. ||:|||:..:  :|..
389 SYAVNRLKK.ASDKELELYLLQLVEAVCFENLSTFSDKSNSEFTIVDAVS 437

645 ............................LDNLLVRFLLKK 656
                                :  . |.  ||:::
438 SQKLSGDSMLLSTSHANQKLLKSISSESETSGTESLPIVISPLAEFLIRR 487
```

FIG. 10D

```
657  ALTNQRIGHFFFWHLKSEMHNKTVSQRFGLLLESY.CRACGMYLKHLNRQ  705
     ||.|.|:|  ||:|.||||  .:|.    ::  :|.|:  :|   .  || |
488  ALVNPRLGSFFYWYLKSESEDKPY...LDQILSSFWSRLDKKSRNILNDQ  534

706  VEAMEKLINLTDILKQEKKDETQKVQMKF.LVEQMRRPDFMDALQGFLSP  754
     |  ::  |  :  .:.:|.  |.....|:::  .  |:|  .  ||   :   :..:   |
535  VRLINVLRECCETIKRLKDTTAKKMELLVHLLETKVRP...LVKVRPIALP  582

755  LNPAHQLGNLRLEECRIMSSAKRPLWLNWENPDIMSELLFQNNEIIFKNG  804
     |:|.    :.::    |.::::.|.  .||.:.:...       ||   ..:|| |
583  LDPDVLICDVCPETSKVFKSSLSPLKITFKTT......LNQPYHLMFKVG  626
                                              *.
805  DDLRQDMLTLQIIRIMENIWQNQGLDLRMLPYGCLSIGDCVGLIEVVRNS  854
     ||||||  |.:|||.:|::::.|:.:||::  ||  .|..|.   |  ||.:.|
627  DDLRQDQLVVQIISLMNELLKNENVDLKLTPYKILATGPQEGAIEFIPN.  675
              *.                                     .  *      *  .         ***
855  HTIMQIQCK.GGLKGALQFNSHTLHQWLKDKNKGEIYDAAIDLFTRSCAG  903
     .|:    |  :|   |:  |  |.:      ::  .:...  ::  :  .:|  |.:||||
676  DTLASILSKYHGILGYLKL......HYPDENATLGVQGWVLDNFVKSCAG  719

904  YCVATFILGIGDRHNSNIMVKDDGQLFHIDFGHFLDHKKKKFGYKRERVP  953
     |||  |:|||:||||  .|::|..||::||  |||.:|:::...|.|             |
720  YCVITYILGVGDRHLDNLLVTPDGHFFHADFGYILGQDPKPF.......P  762

954  FVLTQDFLIVISKGAQECTKTREFERFQEMCYKAYLAIRQHANLFINLFS  1003
     ::..  |:  .  |..|:.    ::::|..  |:  ||  :|.:|.|::|||.
763  PLMKLPPQIIEAFGGAESS...NYDKFRSYCFVAYSILRRNAGLILNLFE  809

1004 MMLGSGMPE..LQSFDDIAYIRKTLALDKTEQEALEYFMKQMNDAHHGGW  1051
     :|  .|.:|:    ::.  :.|    :|.  :.|:..|::|   .|   .:||. :: :
810  IMKTSNIPDIRIDPNGAILRVRERFNLNMSEEDATVHFQNLINDSVNALL  859

1052 TTKMDWIFHTIKQH  1065
     ..  :|   :|.:  |.
860  PIVIDH.LHNLAQY  872
```

```
1    ATGCCTCCAAGACCATCATCAGGTGAACTGTGGGGCATCCACTTGATG           48
     ---------+---------+---------+---------+---------+
     TACGGAGGTTCTGGTAGTAGTCCACTTGACACCCCGTAGGTGAACTAC
     M  P  P  R  P  S  S  G  E  L  W  G  I  H  L  M

49   CCCCCAAGAATCCTAGTGGAATGTTTACTACCAAATGGAATGATAGTG          96
     ---------+---------+---------+---------+---------+
     GGGGGTTCTTAGGATCACCTTACAAATGATGGTTTACCTTACTATCAC
     P  P  R  I  L  V  E  C  L  L  P  N  G  M  I  V

97   ACTTTAGAATGCCCTCCCGTGAGGCTACATTAGTAACTATAAAGCATGAA      144
     ---------+---------+---------+---------+---------+
     TGAAATCTTACGGGAGGGCACTCCGATGTAATCATTGATATTTCGTACTT
     T  L  E  C  L  R  E  A  T  L  V  T  I  K  H  E

145  CTATTTAAAGAAGCAAGAAAATACCCTCTCCATCAACTTCTTCAAGAT        192
     ---------+---------+---------+---------+---------+
     GATAAATTTCTTCGTTCTTTTATGGGAGAGGTAGTTGAAGAAGTTCTA
     L  F  K  E  A  R  K  Y  P  L  H  Q  L  L  Q  D
```

FIG. 16B

```
     GAATCTCTTACATTTTCGTAAGTGTTACCCAAGAAGCAGAAAGGGAA
193  ----------+---------+---------+---------+----  240
     CTTAGAGAATGTAAAAGCATTCACAATGGGTTCTTCGTCTTTCCCTT
      E  S  Y  I  F  V  S  V  T  Q  E  A  E  R  E

GAATTTTTGATGAAACAAGACGACTTTGTGATCTTCGGCTTTTTCAA
241  ----------+---------+---------+---------+----  288
     CTTAAAAACTACTTTGTTCTGCTGAAACACTAGAAGCCGAAAAAGTT
      E  F  F  D  E  T  R  R  L  C  D  L  R  L  F  Q

CCATTTTTAAAAGTAATTGAACCAGTAGGCAACCCGTGAAGAAAAGATC
289  ----------+---------+---------+---------+----  336
     GGTAAAAATTTTCATTAACTTGGTCATCCGTTGGGCACTTCTTTTCTAG
      P  F  L  K  V  I  E  P  V  G  N  R  E  E  K  I

CTCAATCGAGAAATTGGTTTTGCTATCGGCATGCCAGTGTGCGAATTT
337  ----------+---------+---------+---------+----  384
     GAGTTAGCTCTTTAACCAAAACGATAGCCGTACGGTCACACGCTTAAA
      L  N  R  E  I  G  F  A  I  G  M  P  V  C  E  F
```

FIG. 16C

```
385  GATATGGTTAAAGATCCTCTGAAGTACAGGACTTCCGAAGAAATATTCTT
     ----+----+----+----+----+----+----+----+----+----  432
     CTATACCAATTTCTAGGACTTCATGTCCTGAAGGCTTCTTTATAAGAA
      D  M  V  K  D  P  E  V  Q  D  F  R  R  N  I  L

433  AATGTTTGTAAAGAAGCTGTGGATCTTAGGGATCTTAATTCACCTCAT
     ----+----+----+----+----+----+----+----+----+----  480
     TTACAAACATTTCTTCGACACCTAGAATCCCTAGAATTAAGTGGAGTA
      N  V  C  K  E  A  V  D  L  R  D  L  N  S  P  H

481  AGTAGAGCAATGTATGTCTATCCGCCACATGTAGAATCTTCACCAGAG
     ----+----+----+----+----+----+----+----+----+----  528
     TCATCTCGTTACATACAGATAGGCGGTGTACATCTTAGAAGTGGTCTC
      S  R  A  M  Y  V  Y  P  P  H  V  E  S  S  P  E

529  CTGCCAAAGCACACATATAATAAATTGGATAGAGGCCAAATAATAGTG
     ----+----+----+----+----+----+----+----+----+----  576
     GACGGTTTCGTGTATATTATTTAACCTATCTCCGGTTTATTATCAC
      L  P  K  H  I  Y  N  K  L  D  R  G  Q  I  I  V
```

FIG. 16D

```
       GTGATTGGGGTAATAGTTTCTCCAAATAATGACAAGCAGAAGTATACT
577    ---------+---------+---------+---------+---------+    624
       CACTAAACCCATTATCAAAGAGGTTTATTACTGTTCGTCTTCATATGA
        V  I  W  V  I  V  S  P  N  N  D  K  Q  K  Y  T

CTGAAAATCAACCATGTGTGCCAGAACAAGTAATTGCTGAAGCA
625    ---------+---------+---------+---------+---------+    672
       GACTTTTAGTTGGTACTGACACACGGTCTTGTTCATTAACGACTTCGT
        L  K  I  N  H  D  C  V  P  E  Q  V  I  A  E  A

ATCAGGAAAAAAACTAGAAGTATGTTGCTATCATCTGAACAATTAAAA
673    ---------+---------+---------+---------+---------+    720
       TAGTCCTTTTTTTGATCTTCATACAACGATAGTAGACTTGTTAATTTT
        I  R  K  K  T  R  S  M  L  L  S  S  E  Q  L  K

CTCTGTGTTTTAGAATATCAGGGCAAGTACATTTAAAAGTGTGTGGA
721    ---------+---------+---------+---------+---------+    768
       GAGACACAAAATCTTATAGTCCCGTTCATGTAAAATTTCACACACCT
        L  C  V  L  E  Y  Q  G  K  Y  I  L  K  V  C  G
```

FIG. 16E

```
769  TGTGATGAATACTTCCTAGAAAAATATCCTCTGAGTCAGTATAAGTAT  816
     ---------+---------+---------+---------+---------+
     ACACTACTTATGAAGGATCTTTTTATAGGAGACTCAGTCATATTCATA
      C  D  E  Y  F  L  E  K  Y  P  L  S  Q  Y  K  Y

817  ATAAGAAGCTGTATAAATGCTTGGGAGGATGCCCAATTTGAAGATGATG  864
     ---------+---------+---------+---------+---------+
     TATTCTTCGACATATTTACGAACCCTCCTACGGGTTAAACTTCTACTAC
      I  R  S  C  I  M  L  G  R  M  P  N  L  K  M  M

865  GCTAAAGAAAGCCCTTATTCTCAACTGCCAATGGACTGTTTTACAATG  912
     ---------+---------+---------+---------+---------+
     CGATTTCTTTCGGAAATAAGAGTTGACGGTTACCTGACAAAATGTTAC
      A  K  E  S  L  Y  S  Q  L  P  M  D  C  F  T  M

913  CCATCTTATTCCAGACGCATTCCACAGCTACACCATATATGAATGGA  960
     ---------+---------+---------+---------+---------+
     GGTAGAATAAGGTCTGCGTAAGGTGTCGATGTGGTATATACTTACCT
      P  S  Y  S  R  R  I  S  T  A  T  P  Y  M  N  G
```

FIG. 16F

```
961   GAAACATCTACAAAATCCCTTTGGGTTATAAATAGAGCACTCAGAATA   1008
      ------+---------+---------+---------+---------+
      CTTTGTAGATGTTTTAGGGAAACCCAATATTTATCTCGTGAGTCTTAT
      E  T  S  T  K  S  L  W  V  I  N  R  A  L  R  I

1009  AAAATTCTTTGTGCAACCTACGTGAATCTAAATATTCGAGACATTGAC   1056
      ------+---------+---------+---------+---------+
      TTTTAAGAAACACGTTGGATGCACTTAGATTTATAAGCTCTGTAACTG
      K  I  L  C  A  T  Y  V  N  L  N  I  R  D  I  D

1057  AAGATTTATGTTCGAACAGGTATCTACCATGGAGGAGAACCCTTATGT   1104
      ------+---------+---------+---------+---------+
      TTCTAAATACAAGCTTGTCCATAGATGGTACCTCCTCTTGGGAATACA
      K  I  Y  V  R  T  G  I  Y  H  G  G  E  P  L  C

1105  GACAATGTGAACACTCAAAGAGTACCTTGTTCCAATCCCAGGTGGAAT   1152
      ------+---------+---------+---------+---------+
      CTGTTACACTTGTGAGTTTCTCATGGAACAAGGTTAGGGTCCACCTTA
      D  N  V  N  T  Q  R  V  P  C  S  N  P  R  W  N
```

FIG. 16G

```
1153  GAATGGCTGAATTATGATATATACATTCCTGATCTTCCTCGTGCTGCT
      ----+----+----+----+----+----+----+----+----+----+  1200
      CTTACCGACTTAATACTATATATGTAAGGACTAGAAGGAGCACGACGA
       E  W  L  N  Y  D  I  Y  I  P  D  L  P  R  A  A

1201  CGACTTTGCCTTTCCATTGCTCTGTTAAAGGCCGAAAGGGTGCTAAA
      ----+----+----+----+----+----+----+----+----+----+  1248
      GCTGAAACGGAAAGGTAAACGAGACAATTTCCGGCTTTCCCACGATTT
       R  L  C  L  S  I  C  S  V  K  G  R  K  G  A  K

1249  GAGGAACACTGTCCATTGGCATGGGGGAAATATAAACTTGTTTGATTAC
      ----+----+----+----+----+----+----+----+----+----+  1296
      CTCCCTTGTGACAGGTAACCGTACCCCCTTTATATTTGAACAAACTAATG
       E  E  H  C  P  L  A  W  G  N  I  N  L  F  D  Y

1297  ACAGACACTCTAGTATCTGGAAAAATGGCTTTGAATCTTTGGCCAGTA
      ----+----+----+----+----+----+----+----+----+----+  1344
      TGTCTGTGAGATCATAGACCTTTTTACCGAAACTTAGAAACCGGTCAT
       T  D  T  L  V  S  G  K  M  A  L  N  L  W  P  V
```

FIG. 16H

```
1345  CCTCATGGATTAGAAGATTTGCTGAACCCTATTGGTGTTACTGGATCA  1392
      ---------+---------+---------+---------+---------+--
      GGAGTACCTAATCTTCTAAACGACTTGGGATAACCACAATGACCTAGT
       P  H  G  L  E  D  L  L  N  P  I  G  V  T  G  S

1393  AATCCAAATAAAGAAACTCCATGCTTAGAGTTGGAGTTTGACTGGTTC  1440
      ---------+---------+---------+---------+---------+--
      TTAGGTTTATTTCTTTTGAGGTACGAATCTCAACCTCAAACTGACCAAG
       N  P  N  K  E  T  P  C  L  E  L  E  F  D  W  F

1441  AGCAGTGTGGTAAAGTTCCCAGATATGTCAGTGATTGAAGAGCATGCC  1488
      ---------+---------+---------+---------+---------+--
      TCGTCACACCATTTCAAGGGTCTATACAGTCACTAACTTCTCGTACGG
       S  S  V  V  K  F  P  D  M  S  V  I  E  E  H  A

1489  AATTGGTCTGTATCCCGAGAAGCAGGATTTAGCTATTCCCACGCAGGA  1536
      ---------+---------+---------+---------+---------+--
      TTAACCAGACATAGGGCTCTTCGTCCTAAATCGATAAGGGTGCGTCCT
       N  W  S  V  S  R  E  A  G  F  S  Y  S  H  A  G
```

FIG. 16I

```
     CTGAGTAACAGACTAGCTAGAGACAATGAATTAAGGGAAAATGACAAA
     ---------+---------+---------+---------+--------    1584
     GACTCATTGTCTGATCGATCTCTGTTACTTAATTCCCTTTTACTGTTT
1537 L  S  N  R  L  A  R  D  N  E  L  R  E  N  D  K

GAACAGCTCAAAGCAATTTCTACACGAGATCCTCTCTGAAATCACT
     ---------+---------+---------+---------+------      1632
     CTTGTCGAGTTTCGTTAAAGATGTGCTCTAGGAGAGACTTTAGTGA
1585 E  Q  L  K  A  I  S  T  R  D  P  L  S  E  I  T

GAGCAGGAGAAAGATTTCTATGGAGTCACAGACACTATTGTGTAACT
     ---------+---------+---------+---------+-------     1680
     CTCGTCCTCTTTCTAAAGATACCTCAGTGTCTGTGATAACACATTGA
1633 E  Q  E  K  D  F  L  W  S  H  R  H  Y  C  V  T

ATCCCCGAAATTCTACCCAAATTGCTTCTGTTCTGTGTTAAATGGAATTCT
     ---------+---------+---------+---------+---------   1728
     TAGGGGCTTTAAGATGGGTTTAACGAAGACAGACAATTACCTTAAGA
1681 I  P  E  I  L  P  K  L  L  L  S  V  K  W  N  S
```

FIG. 16J

```
1729  AGAGATGAAGTAGCCCAGATGTATTGCTTGGTAAAAGATTGGCCTCCA  1776
      ----+----|----+----|----+----|----+----|----+----|
      TCTCTACTTCATCGGGTCTACATAACGAACCATTTTCTAACCGGAGGT
       R  D  E  V  A  Q  M  Y  C  L  V  K  D  W  P  P

1777  ATCAAACCTGAACAGGCTATGGAACTTCTGGACTGTAATTACCCAGAT  1824
      ----+----|----+----|----+----|----+----|----+----|
      TAGTTTGGACTTGTCCGATACCTTGAAGACCTGACATTAATGGGTCTA
       I  K  P  E  Q  A  M  E  L  L  D  C  N  Y  P  D

1825  CCTATGGTTCGAGGTTTTTGCTGTTCGGTGCTTGGAAAATATTTAACA  1872
      ----+----|----+----|----+----|----+----|----+----|
      GGATACCAAGCTCCAAAACGACAAGCCACGAACCTTTTATAAATTGT
       P  M  V  R  G  F  A  V  R  C  L  E  K  Y  L  T

1873  GATGACAAACTTTCTCAGTATTTAATTCAGCTAGTACAGGTCCTAAAA  1920
      ----+----|----+----|----+----|----+----|----+----|
      CTACTGTTTGAAAGAGTCATAAATTAAGTCGATCATGTCCAGGATTTT
       D  D  K  L  S  Q  Y  L  I  Q  L  V  Q  V  L  K
```

FIG. 16K

```
         TATGAACAATATTTGGATAACTTGCTTGTGAGATTTTTACTGAAGAAA        1968
         ----+----|----+----|----+----|----+----|----+----|
         ATACTTGTTATAAACCTATTGAACGAACACTCTAAAAATGACTTCTTT
          Y  E  Q  Y  L  D  N  L  L  V  R  F  L  L  K  K

GCATTGACTAATCAAAGGATTGGGCACTTTTTCTTTTGGCATTTAAAA        2016
         ----+----|----+----|----+----|----+----|----+----|
         CGTAACTGATTAGTTTCCTAACCCGTGAAAAGAAAACCGTAAATTTT
          A  L  T  N  Q  R  I  G  H  F  F  F  W  H  L  K

TCTGAGATGCACAATAAAACAGTTAGCCAGAGGTTTGGCCTGCTTTTG        2064
         ----+----|----+----|----+----|----+----|----+----|
         AGACTCTACGTGTTATTTTGTCAATCGGTCTCCAAACCGGACGAAAAC
          S  E  M  H  N  K  T  V  S  Q  R  F  G  L  L  L

GAGTCCTATTGTCGTGCATGTGGGATGTATTTGAAGCACCTGAATAGG        2112
         ----+----|----+----|----+----|----+----|----+----|
         CTCAGGATAACAGCACGTACACCCTACATAAACTTCGTGGACTTATCC
          E  S  Y  C  R  A  C  G  M  Y  L  K  H  L  N  R
1921
1969
2017
2065
```

FIG. 16L

```
2113  CAAGTCGAGGCAATGGAAAAGCTCATTAACTTAACTGACATTCTCAAA  2160
      ------+---------+---------+---------+---------+
      GTTCAGCTCCGTTACCTTTTCGAGTAATTGACTGTAAGAGTTT
       Q  V  E  A  M  E  K  L  I  N  L  T  D  I  L  K

2161  CAGGAGAGGAAGGATGAAAACACAAAAGGTACAGATGAAGTTTTAGTT  2208
      ------+---------+---------+---------+---------+
      GTCCTCTCCTTCCTACTTTGTGTTTTCCATGTCTACTTCAAAATCAA
       Q  E  R  K  D  E  T  Q  K  V  Q  M  K  F  L  V

2209  GAGCAAATGAGGCGACCAGATTTCATGGATGCCCTACAGGGCTTGCTG  2256
      ------+---------+---------+---------+---------+
      CTCGTTTACTCCGCTGGTCTAAAGTACCTACGGGATGTCCCGAACGAC
       E  Q  M  R  R  P  D  F  M  D  A  L  Q  G  L  L

2257  TCTCCTCTAAACCCTGCTCATCAACTAGGAAACCTCAGGCTTAAAGAG  2304
      ------+---------+---------+---------+---------+
      AGAGGAGATTTGGGACGAGTTGATCCTTTGGAGTCCGAATTCTC
       S  P  L  N  P  A  H  Q  L  G  N  L  R  L  K  E
```

FIG. 16M

```
2305  TGTCGAATTATGTCTTCTCTGCAAAAGGCCACTGTGGTTGAATTGGGAG   2352
      ---------+---------+---------+---------+---------+
      ACAGCTTAATACAGAAGAGACGTTTTCCGGTGACACCAACTTAACCCTC
       C  R  I  M  S  S  A  K  R  P  L  W  N  W  E

2353  AACCCAGACATCATGTCAGAGTTACTGTTTCAGAACAATGAGATCATC   2400
      ---------+---------+---------+---------+---------+
      TTGGGTCTGTAGTACAGTCTCAATGACAAAGTCTTGTTACTCTAGTAG
       N  P  D  I  M  S  E  L  L  F  Q  N  N  E  I  I

2401  TTTAAAAATGGGGATGATTTACGGCAAGATATGCTAACACTTCAAATT   2448
      ---------+---------+---------+---------+---------+
      AAATTTTTACCCCTACTAAATGCCGTTCTATACGATTGTGAAGTTTAA
       F  K  N  G  D  D  L  R  Q  D  M  L  T  L  Q  I

2449  ATTCGTATTATTATGGAAAATATCTGGCAAATCAAGGTCTTGATCTTCGA   2496
      ---------+---------+---------+---------+---------+
      TAAGCATAATAACCTTTTATAGACCGTTTAGTTCCAGAACTAGAAGCT
       I  R  I  M  E  N  I  W  Q  N  Q  G  L  D  L  R
```

FIG. 16N

```
2497  ATGTTACCTTATGGTTGTGTCTGTCAATCGGTGTGACTGTGTGGGACTTATT
      ----+----+----+----+----+----+----+----+----+----+    2544
      TACAATGGAATACCAACAGACAGTTAGCCACACTGACACACCCTGAATAA
       M   L   P   Y   G   C   L   S   I   G   D   C   V   G   L   I

2545  GAGGTGGTGCGAAATTCTCACACTATTATGCAAATTCAGTGCAAAGGC
      ----+----+----+----+----+----+----+----+----+----+    2592
      CTCCACCACGCTTTAAGAGTGTGATAATACGTTTAAGTCACGTTTCCG
       E   V   V   R   N   S   H   T   I   M   Q   I   Q   C   K   G

2593  GGCTTGAAAGGTGCACTGCAGTTCAACAGCCACACTACATCAGTGG
      ----+----+----+----+----+----+----+----+----+----+    2640
      CCGAACTTTCCACGTGACGTCAAGTTGTCGGTGTGATGTAGTCACC
       G   L   K   G   A   L   Q   F   N   S   H   T   L   H   Q   W

2641  CTCAAAGAAGACAAGAACAAAGGAGAAATATATGATGCAGCCATTGACCTG
      ----+----+----+----+----+----+----+----+----+----+    2688
      GAGTTTCTGTTCTTGTTTCCTCTTTATATACTACGTCGGTAACTGGAC
       L   K   D   K   N   K   G   E   I   Y   D   A   A   I   D   L
```

FIG. 16O

```
2689  TTTACACGTTCATGTGCTGGATACTGTGTAGCTACCTTTCATTTTGGGA
      ----+---------+---------+---------+---------+----  2736
      AAATGTGCAAGTACACGACCTATGACACATCGATGGAAGTAAAACCCT
       F  T  R  S  C  A  G  Y  C  V  A  T  F  I  L  G

2737  ATTGGAGATCGTCACAATAGTAACATCATGGTGAAAGACGATGGACAA
      ----+---------+---------+---------+---------+----  2784
      TAACCTCTAGCAGTGTTATCATTGTAGTACCACTTTCTGCTACCTGTT
       I  G  D  R  H  N  S  N  I  M  V  K  D  D  G  Q

2785  CTGTTCATATAGATTTTGGACACTTTTTGGATCACAAGAAGAAAAAA
      ----+---------+---------+---------+---------+----  2832
      GACAAGTATATCTAAAACCTGTGAAAACCTAGTGTTCTTCTTCTTTTT
       L  F  H  I  D  F  G  H  F  L  D  H  K  K  K  K

2833  TTTGGTTATAAACGAGAACGTGTGCCATTTGTTTTTGACACAGGATTTC
      ----+---------+---------+---------+---------+----  2880
      AAACCAATATTTGCTCTTGCACACGGTAAACAAAACTGTGTCCTAAAG
       F  G  Y  K  R  E  R  V  P  F  V  L  T  Q  D  F
```

FIG. 16P

```
2881  TTAATAGTGATTAGTAAGGAGCCCAAGAATGCACAAAGACAAGAGAA
      ----+----+----+----+----+----+----+----+----+----  2928
      AATTATCACTAATCATTCCTCGGGTTCTTACGTGTTTCTGTTCTCTT
       L  I  V  I  S  K  G  A  Q  E  C  T  K  T  R  E

2929  TTTGAGAGGTTTCAGGAGATGTGTTACAAGGCTTATCTAGCTATTCGA
      ----+----+----+----+----+----+----+----+----+----  2976
      AAACTCTCCAAAGTCCTCTACACAATGTTCCGAATAGATCGATAAGCT
       F  E  R  F  Q  E  M  C  Y  K  A  Y  L  A  I  R

2977  CAGCATGCCAATCTCTTCATAAATCTTTTCTCAATGATGCTTGGCTCT
      ----+----+----+----+----+----+----+----+----+----  3024
      GTCGTACGGTTAGAGAAGTATTTAGAAAAGAGTTACTACGAACCGAGA
       Q  H  A  N  L  F  I  N  L  F  S  M  M  L  G  S

3025  GGAATGCCAGAACTACAATCTTTTGATGTTAGACATTGCATACATTCGAAAG
      ----+----+----+----+----+----+----+----+----+----  3072
      CCTTACGGTCTCTTGATGTTAGAAAACTACTGTAACGTATGTAAGCTTTC
       G  M  P  E  L  Q  S  F  D  D  I  A  Y  I  R  K
```

FIG. 16Q

```
3073  ACCCTAGCCCTTAGATAAAACTGAGCAAGAGGCTTTGGAGTATTTCATG
      ---------+---------+---------+---------+--------  3120
      TGGGATCGGAATCTATTTTGACTCGTTCTCCGAAACCTCATAAAGTAC
       T  L  A  L  D  K  T  E  Q  E  A  L  E  Y  F  M

3121  AAACAAAATGAATGATGCACATCATGGTGGCTGGACAACAAAAATGGAT
      ---------+---------+---------+---------+--------  3168
      TTTGTTTTACTTACTACGTGTAGTACCACCGACCTGTTGTTTTTACCTA
       K  Q  M  N  D  A  H  H  G  G  W  T  T  K  M  D

3169  TGGATCTTCCACACAATTAAACAGCATTGAACTGAAAGATAACT
      ---------+---------+---------+---------+--------  3216
      ACCTAGAAGGTGTGTTAATTTGTCGTAACTTGACTTTCTATTGA
       W  I  F  H  T  I  K  Q  H  A  L  N  *

3217  GAGAAAATGAAAGCTCACTCTGGATTCCACACTGCCACTGTTAATAACT
      ---------+---------+---------+---------+--------  3264
      CTCTTTTACTTTCGAGTGAGACCTAAGGTGTGACGGTGACAATTATTGA
```

FIG. 16R

```
      CTCAGCAGGCAAAGACCGATTGCATAGGAATTGCACAATCCATGAACA
3265  ---+----+----+----+----+----+----+----+---- 3312
      GAGTCGTCCGTTTCTGGCTAACGTATCCTTAACGTGTTAGGTACTTGT

GCATTAGATTTACAGCAAGAACAGAAATAAAATACTATATAATTTAAA
3313  ---+----+----+----+----+----+----+----+---- 3360
      CGTAATCTAAATGTCGTTCTTGTCTTTATTTTATGATATATTAAATTT

TAATGTAAAACGCAAACAGGGTTTGATAGCACTTAAACTAGTTCATTTC
3361  ---+----+----+----+----+----+----+----+---- 3408
      ATTACATTTGCGTTTGTCCCAAACTATCGTGAATTTGATCAAGTAAAG

AAAA
3409  ---+---  3412
      TTTT
```

FIG. 17A

```
hum110    1  ATGCCTCCAAGACCATCATCAGGTGAACTGTGGGGCATCCACTTGATGCC   50
             ||||||||||||||||||||||||||||||||||||||||||||||||||
bov110    1  ATGCCTCCAAGACCATCATCAGGTGAACTGTGGGGCATCCACTTGATGCC   50

51  CCCAAGAATCCTAGTGGAATGTTTACTACCAAATGGAATGATAGTGACTT  100
             ||||||||||||||||| ||||||||||||||||| ||||||||||||||
         51  CCCAAGAATCCTAGTAGAATGTTTACTACCAAATGGATGATAGTGACTT  100

101  TAGAATGCCTCCGTGAGGCTACACATTAGTAACTATAAAGCATGAACTATTT  150
             |||||||||||||||||||||||| ||| |||||||||||||||||||||
        101  TAGAATGCCTCCGTGAGGCTACGTTAATAACTATAAAGCATGAACTATTT  150

151  AAAGAAGCAAGAAAAATACCCTCTCCATCAACTTCTTCAAGATGAATCTTC  200
             ||||||||||||| ||||||||||||||||||||||||||||||||||||
        151  AAAGAAGCAAGAAAAATACCCTCTCCATCAACTTCTTCAAGATGAATCTTC  200
```

FIG. 17B

```
201 TTACATTTTCGTAAGTGTTACCCAAGAGAAGCAGAGAAAGGGAAGAATTTTTG 250
    ||||||||||||||||||||||||||||||||||||||||||||||||||||
201 TTACATTTTCGTAAGTGTTACCCAAGAGAAGCAGAGAAAGGGAAGAATTTTTG 250

251 ATGAAACAAGACGACTTTGTGATCTTCGGCTTTTCAACCATTTTTAAAA 300
    ||||||||||||||||||||||||||||||||||||||| ||||||||
251 ATGAAACAAGACGACTTTGTGACCTTTGTGACCTTCGGCCTTTTCAACCCTTTTTAAAA 300

301 GTAATTGAACCAGTAGGCAACCGTGAAGAAAAGATCCTCAATCGAGAAAT 350
    ||||||||||||||||||||||||||||||||||||||||||||||||
301 GTAATTGAACCAGTAGGCAACCGTGAAGAAAAGATCCTCAATCGAGAAAT 350

351 TGGTTTTGCTATCGGCATGCCAGTGTGCGAATTTGATATGGTTAAAGATC 400
    |||||||||||||||||||||||||||| ||| |||||||||||||||
351 TGGTTTTGCTATCGGCATGCCAGTGTGAATTCGATGTGAATTCGATATGGTTAAAGATC 400

401 CTGAAGTACAGGACTTCCGAAGAAATATTCTTAATGTTTGTAAAGAAGCT 450
    | |||||||||||||||||||||||||||| |||||||||||||||||
401 CAGAAGTACAGGACTTCCGAAGAAATATTCTCAATGTTTGTAAAGAAGCT 450
```

FIG. 17C

```
451  GTGGATCTTAGGGATCTTAATTCACCTCATAGTAGAGCAATGTATGTCTA  500
     |||||||||||||||||||||||||||||||| || |||||||||| ||
451  GTGGATCTTAGGGATCTTAATTCACCTCATAGTAGAGCAATGTATGTTTA  500

501  TCCGCCACATGTAGAATCTTCACCAGAGCTGCCAAAGCACACATATATAATA  550
     ||| ||  ||||||||||||||||| |||||||||||||||||||||||
501  TCCTCCAAATGTAGAATCTTCACCAGAACTGCCAAAGCACACATATATAATA  550

551  AATTGGATAGAGGCCAAATAATAGTGGTGATTTGGGTAATAGTTTCTCCA  600
     ||||||||||  ||| |||||||||||||||||||||||||||||||||
551  AATTGGATAAAGGGCCAAATAATAGTGGTGATTTGGGTAATAGTTTCTCCA  600

601  AATAATGACAAGCAGAAGTATACTCTGAAAATCAACCATGACTGTGTGCC  650
     |||||||||||||||||||||||||||||||||||||||||||||||||
601  AATAATGACAACAGAAGTATACTCTGAAAATCAACCATGACTGTGTGCC  650

651  AGAACAAGTAATTGCTGAAGCAATCAGGAAAAACTAGAAGTATGTTGC  700
     ||||||||||||||||||||||||||| |||||| ||||||||||||||
651  AGAACAAGTAATTGCTGAAGCAATCAGGAAAAAACTCGAAGTATGTTGC  700
```

FIG. 17D

```
701  TATCATCTGAACAATTAAAACTCTGTGTTTTAGAATATCAGGGCAAGTAC  750
     ||||||||||||||| ||||||||||||||||||||||||||||||||||
701  TATCATCTGAACAACTAAAACTCTGTGTTTTAGAATATCAGGGCAAGTAT  750

751  ATTTAAAAGTGTGTGGATGTGATGAATACTTCCTAGAAAAATATCCTCT  800
     |||||||||||||||||||||| |||||||||||||||||||||||||||
751  ATTTAAAAGTGTGTGGATGTGATGAATACTTCCTAGAAAAATATCCTCT  800

801  GAGTCAGTATAAGTATATAAGAAGCTGTATAATGCTTGGGAGGATGCCCA  850
     |||||||||||||||||||||||||||||||||||||||||||||||||
801  GAGTCAGTATAAGTATATAAGAAGCTGTATAATGCTTGGGAGGATGCCCA  850

851  ATTTGAAGATGATGGCTAAAGAAAGCCTTTATTCTCAACTGCCAATGGAC  900
     |||||  ||| ||||||||||||||||||||||||||||||||||||||
851  ATTTGATGATGCTGATGGCTAAAGAAAGCCCTCTATTCTCAACTGCCAATGGAC  900

901  TGTTTTACAATGCCATCTCTTATTCCAGACGCCATTTCCACACCATA  950
     ||||| |||||||||||  ||||||||||||  |||||||||  ||| |||
901  TGTTTTACAATGCCATCATATATTCCAGACGCCATTCCACAGCTACGCCATA  950
```

FIG. 17E

```
 951 TATGAATGGAGAAACATCTACAAAATCCCTTTGGGTTATAAATAGAGCAC 1000
     ||||||||||||||||||||||||||||||||||||||||| |||  |||
 951 TATGAATGGAGAAACATCTACAAAATCCCTTTGGGTTATAAATAGTGCAC 1000

1001 TCAGAATAAAAATTCTTTGTGCAACCTACGTGAATCTAAATATTCGAGAC 1050
     ||||||||||||||||||||||||||||| ||||||||| ||||||||||
1001 TCAGAATAAAAATTCTTTGTGCAACCTATGTGAATGTAAATATTCGAGAC 1050

1051 ATTGACAAGATTTATGTTCGAACAGTCTACCATGGAGGAGAACCCTT    1100
     ||||||||||||||||||||||||| |||||||||||||||||||||
1051 ATTGACAAGATTTATGTTCGAACAGGTATCTACCATGGAGGAGAACCCTT 1100

1101 ATGTGACAATGTGAACACTCAAAGAGTACCTTGTTCCAATCCCAGGTGGA 1150
     |||| ||||||||||||||||||||||||||||||||||||||||||||
1101 ATGTGATAATGTGAACACTCAAAGAGTACCTTGTTCCAATCCCAGGTGGA 1150

1151 ATGAATGGCTGAATTATGATATATACATTCCTGATCTTCCTCGTGCTGCT 1200
     |||||||||||||||| ||||||||||||||||||||||||||||||||
1151 ATGAATGGCTGAATTACGATATATACATTCCTGATCTTCCTCGTGCTGCT 1200
```

FIG. 17F

```
1201  CGACTTTGCCTTTCCATTTGCTCTGTTAAAGGCCGAAAGGGTGCTAAAGA  1250
      ||||||||||||||||||||||||||||||||||||||||||||||||||
1201  CGACTTTGCCTTTCCATTTGTTCTGTTAAAGGCCGAAAGGGTGCTAAAGA  1250

1251  GGAACACTGTCCATTGGCCATGGGGAAATATAAACTTGTTTGATTACACAG  1300
      ||||||||||||||||||||| |||||||||||||||||||||||||||
1251  GGAACACTGTCCATTGGCCTGGGGAAATATAAACTTGTTTGATTACACAG  1300

1301  ACACTCTAGTATCTGGAAAATGGCTTTGAATCTTTGGCCAGTACCTCAT  1350
      | ||||||||||||||||||| ||||||||||||||||||||||||||
1301  ATACTCTAGTATCTGGAAAATCGGCTTTGAATCTTTGGCCAGTACCTCAT  1350

1351  GGATTAGAAGAGATTTGCTGAACCCTATTGGTGTTACTGGATCAAATCCAAA  1400
      ||| ||||||||||||||||||||||||||||||||||||||||||||
1351  GGACTAGAAGAGATTTGCTGAACCCTATTGGTGTTACTGGATCAAATCCAAA  1400

1401  TAAAGAAAACTCCATGCTTAGAGTTGGACTGGTTCAGCAGTGTGG  1450
      ||||||||||||||||| ||||| ||||||||||||||||||||
1401  TAAAGAAAACTCCATGTTTAGAGTTGGAGTTTGACTGGTTCAGCAGTGTGG  1450
```

FIG. 17G

```
1451  TAAAGTTCCCAGATATGTCAGTGATTGAAGAGCATGCCAATTGGTCTGTA  1500
      |||||  ||||||||||||||||||||||  ||||||||||||||||||
1451  TAAAGTTTCCAGATATGTCAGTGATTGAAGAGCATGCCAATTGGTCTGTA  1500

1501  TCCCGAGAAGCAGGATTTAGCTATTCCCACGCAGGACTGAGTAACAGACT  1550
      ||| || ||||||||| |||| ||||||||||||||||||||||||||
1501  TCCCGTGAAGCAGGATTTAGTTATTCCCATGCAGGACTGAGTAACAGACT  1550

1551  AGCTAGAGACAATGAATTAAGGGAAAATGACAAAGAACAGCTCAAAGCAA  1600
      ||||||||| ||||||||||| ||||||||  |||||||||||| ||||
1551  AGCTAGAGAGAATGAATTAAGAGAAAATGATAAAGAACAGCTCCGAGCAA  1600

1601  TTTCTACACGAGATCCCTCTCTGAAATCACTGAGCAGGAGAAAGATTTT  1650
      ||| |||||||||||||| || |||||||||||||||||||||||||||
1601  TTTGTACACGAGATCCCTCTATCTGAAATCACTGAGCAAGAGAAAGATTTT 1650

1651  CTATGGAGTCACAGACACTATTGTGTAACTATCCCCGAAATTCTACCCAA  1700
      ||  |||||||||||||||||||| |||||||||||||||||||||||
1651  CTGTGGAGCCACAGACACTATTGTGTAACTATCCCCGAAATTCTACCCAA  1700
```

FIG. 17H

```
1701 ATTGCTTCTGTCTGTTAAATGGAATTCTAGAGATGAAGTAGCCCAGATGT 1750
     ||||||||||||||||||||||||||||||||||| ||||||| |||||
1701 ATTGCTTCTGTCTGTTAAATGGAACTCTAGAGATGAAGTAGCTCAGATGT 1750

1751 ATTGCTTGGTAAAAGATTGGCCTCCAATCAAACCTGAACAGGCTATGGAA 1800
     |||||||||||||||||||| ||||||||||| ||||||||||||||| 
1751 ACTGCTTGGTAAAAGATTGGCCTCCAATCAAGCCTGAACAGGCTATGGAG 1800

1801 CTTCTGGACTGTAATTACCCAGATCCTATGGTTCGAGGTTTTGCTGTTCG 1850
     ||||||||||| ||||||||||||||||||||||||||||||||||||||
1801 CTTCTGGACTGCAATTACCCAGATCCTATGGTTCGAGGTTTTGCTGTTCG 1850

1851 GTGCTTGGAAAAATATTTAACAGATGACAAACTTTCTCAGTATTTAATTC 1900
     |||||||||| ||||||||||||||||||||||||||||||| |||||||
1851 GTGCTTAGAAAAATATTTAACAGATGACAAACTTTCTCAGTACCTAATTC 1900

1901 AGCTAGTACAGGTCCTAAAATGAACAATATTTGGATAACTTGCTTGTG 1950
     |||||||||||| |||||| ||||||||||||||||||||| |||||||
1901 AGCTAGTACAGTACTAAAATGAACAGTATTTGGATAACCTGCTTGTG 1950
```

FIG. 171

```
1951  AGATTTTACTGAAGAAAGCATTGACTAATCAAAGGATTGGGCACTTTTT  2000
      ||||||||||| || ||||  ||||  ||||||||||| || |||||||
1951  AGATTTTACTCAAAAAAGCGTTAACTAATCAAAAGGATCGGTCACTTTTT  2000

2001  CTTTGGCATTTAAAATCTGAGATGCACAATAAAACAGTTAGCCAGAGGT  2050
      |||||||||||||||||||||||||||||||||||||||| |||||||
2001  CTTTTGGCATTTAAAATCTGAGATGCACAATAAAACAGTTAGTCAGAGGT  2050

2051  TTGGCCTGCTTTTGGAGTCCTATTGTCGTGCATGTGGGATGTATTTGAAG  2100
      ||||| |||||||||||||||||||| |||||||||||||||| |||||
2051  TTGGCCTGCTTTTGGAGTCCTATTGCCGTGCATGTGGGATGTATCTGAAG  2100

2101  CACCTGAATAGGCAAGTCGAGGCAATGGAAAAGCTCATTAACTTAACTGA  2150
      ||||| || ||||||||| |||||||||||||||||||||||| ||||||
2101  CACCTTAATAGGCAAGTTGAGGCTATGGAAAAGCTCATTAACTTGACTGA  2150

2151  CATTCTCAAACAGGAGAGGAAGGATGAAACACAAAAGGTACAGATGAAGT  2200
      ||||||||||||| ||||| ||||||||||||||||||||||||||||||
2151  CATTCTCAAACAAGAGAGAAGAAGGATGAAACACAAAAGGTACAGATGAAGT  2200
```

FIG. 17J

```
2201  TTTTAGTTGAGCAAATGAGGGCGACCAGATTTCATGGATGCCCTACAGGGC  2250
      ||||| |||||||||||| ||  |||||||||||||||||||| ||||||
2201  TTTTAGTTGAGCAAATGCGGGCGACCAGATTTCATGGATGCTCCCAGGGC  2250

2251  TTGCTGTCTCCTCTAAACCCTGCTCATCAACTAGGAAACCTCAGGCTTAA  2300
      || || |||||||||||||||||||||||| |||| ||| |||||||| 
2251  TTTCTGTCTCCTCTAAACCCTGCTCATCAGCTAGGAAATCTCAGGCTTGA  2300

2301  AGAGTGTCGAATTATGTCTTCTGCAAAAAGGCCACTGTGGTTGAATTGGG  2350
      |||||||||||||||||||| ||||||||||||||||||||||||||||
2301  AGAGTGTCGAATTATGTCTTCTGCAAAAAGGCCACTGTGGTTGAATTGGG  2350

2351  AGAACCCAGACATCATGTCAGAGTTACTGTGTTTCAGAACAATGAGATCATC  2400
      ||||||||||||||||||| |||||||| ||||  ||||||||||||||||
2351  AGAACCCAGACATCATGTCAGAATTACTCTTTCAGAACAATGAGATCATC  2400

2401  TTTAAAAATGGGGATGATTTACGGCAAGATATGCTAACACTTCAAATTAT  2450
      ||||||||||||||||||||||||||||||||||||||||  ||||||||
2401  TTTAAAAATGGGGATGATTTACGGCAAGATATGCTAACCCTTCAGATTAT  2450
```

FIG. 17K

```
2451 TCGTATTATGGAAAAATATCTGGCAAAATCAAGGTCTCTTGATCTTCGAATGT 2500
     ||| ||||||||||||||||| |||||||||||||||| |||||||||||||
2451 TCGCATTATGGAAAAATATCTGGCAAAATCAAGGTCTCTTGATCTTCGAATGT 2500

2501 TACCTTATGGTTGTCTGTGTCAATCGGTGACTGTGTGGGACTTATTGAGGTG 2550
     |||||||||| ||| ||||||| |||||||||||||||||||| ||||||||
2501 TACCTTATGGATGTCTGTCAATCGGTGACTGTGTGGGACTTATGGAGGTG 2550

2551 GTGCGAAATTCTCACACTATTATGCAAATTCAGTGCAAAGGCGGCTTGAA 2600
     || |||||||||||||| ||| ||||||||||||| ||| |||| ||||||
2551 GTGAGAAATTCTCACACTATAATGCAGATTCAGTGTAAAGGAGGCCTGAA 2600

2601 AGGTGCACTGCAGTTCAACAGCCACACACTACATCAGTGGCTCAAAGACA 2650
     ||||||||||||||||| ||||||| |||||||| ||||||||||||||||
2601 AGGTGCACTGCAGTTTAACAGCCACACACTCCATCAGTGGCTCAAAGACA 2650

2651 AGAACAAAGGAGAAATATATGATGCAGCCATTGACCTGTTTACACGTTCA 2700
     ||||||||| |||||| ||||||||||||||| || |||||||||| |||
2651 AGAACAAGGGGGAAAATATATGATGCGGCCATCGATTTGTTTACACGATCA 2700
```

FIG. 17L

```
2701  TGTGCTGGATACTGTGTGTAGCTACCTTCATTTTGGGAATTGGAGATCGTCA  2750
      |||||||||| |||| |||| ||   ||||||||||||||||||||||||||
2701  TGTGCTGGATATTGTGTGTTGCCACCTTCATTTTGGGAATTGGAGATCGTCA  2750

2751  CAATAGTAACACATCATGGTGAAAGAGACGATGGACAACTGTTTCATATAGATT  2800
      ||||||||| |||  |||| ||||   ||| ||||||||||||||||||||||
2751  CAATAGTAATATCATGGTTAAAGATGATGGACAACTGTTTCATATAGATT  2800

2801  TTGGACACTTTTTGGATCACAAGAAGAAAAAAATTGGTTATAAACGAGAA  2850
      ||||| ||||||||||||||||||||||||||||||||||||||||||||
2801  TTGGACACTTTTTGGATCACAAGAAGAAAAAAATTGGTTATAAACGAGAG  2850

2851  CGTGTGCCATTTGTTTTTGACACAGGATTCTTAATAGTGATTAGTAAAGG  2900
      | ||||||| ||||||||||||| |||| | |||||||||||||||||||
2851  CGCGTGCCGTTTGTTTTTGACACAAGATTTCTTAATAGTGATTAGTAAAGG  2900

2901  AGCCCAAGAATGCACAAAGACAAGAGAATTTGAGAGGTTTCAGGAGATGT  2950
      |||| |||||||||||||||||||||||||||||||||||||||||||||
2901  AGCCCAAGAATGCACAAAGACAAGAGAATTTGAGAGGTTTCAGGAGATGT  2950
```

FIG. 17M

```
2951 GTTACAAGGCTTATCTAGCTATTCGACAGCATGCCAATCTCTTCATAAAT 3000
     |||||||||||||||||||||||||| |||||||||||||||||||||||
2951 GTTACAAGGCTTATCTAGCTATTCGGCAGCATGCCAATCTCTTCATAAAT 3000

3001 CTTTTCTCAATGATGCTTGGCTCTGGAATGCCAGAACTACAATCTTTTGA 3050
     |||||||||||||||||||||||||||||||||||| |||||||||||||
3001 CTTTTCTCAATGATGCTTGGCTCTGGAATGCCAGAACTGCAATCTTTTGA 3050

3051 TGACATTGCATACATTCGAAAGACCCTAGCCTTTAGATAAAACTGAGCAAG 3100
     ||| ||| |||||||||||||||||||||||||||||||||||||||||
3051 TGATATTGCATACATTCGAAAGACCCTAGCCTTTAGATAAAACTGAGCAAG 3100

3101 AGGCTTTGGAGTATTTCATGAAACAAATGATGCACATCATGGTGGC 3150
     |||||||||||||||||||||||||||||| ||||||||| ||||||||
3101 AGGCTTTGGAGTATTTCATGAAACAAATGATGCACACCATGGTGGC 3150

3151 TGGACAACAAAAATGGATTGGATCTTCCACACAATTAAACAGCATGCATT 3200
     |||||||||||||||||||||||||||||||||||||||| |||||| ||
3151 TGGACAACAAAAATGGATTGGATCTTCCACACAATTAAGCAGCATGCTTT 3200

3201 GAACTGAAAGATAACTGAGAAAATGAAAGCTCACTCTGA
     |||||||
3201 GAACTGA..........................................
```

FIG. 18A

```
         10         20         30         40         50         60
h MPPRPSSGELWGIHLMPPRILVECLLPNGMIVTLECLREATLVTIKHELFKEARKYPLHQ
  ||||||||||||||||||||||||||||||||||||:|||:|||||||||||||||||
b MPPRPSSGELWGIHLMPPRILVECLLPNGMIVTLECLREATLITIKHELFKEARKYPLHQ
         10         20         30         40         50         60

70         80         90        100        110        120
h LLQDESSYIFVSVTQEAEREEFFDETRRLCDLRLFQPFLKVIEPVGNREEKILNREIGFA
  ||||||||||||||||||||||||||||||||||||||||||||||||||||||||||
b LLQDESSYIFVSVTQEAEREEFFDETRRLCDLRLFQPFLKVIEPVGNREEKILNREIGFA
         70         80         90        100        110        120

130        140        150        160        170        180
h IGMPVCEFDMVKDPEVQDFRRNILNVCKEAVDLRDLNSPHSRAMYVYPPHVESSPELPKH
  ||||||||||||||||||||||||||||||||||||||||||||||:||||||||||||
b IGMPVCEFDMVKDPEVQDFRRNILNVCKEAVDLRDLNSPHSRAMYVYPPNVESSPELPKH
        130        140        150        160        170        180
```

FIG. 18B

```
            190        200        210        220        230        240
h  IYNKLDRGQIIVVIWVIVSPNNDKQKYTLKINHDCVPEQVIAEAIRKKTRSMLLSSEQLK
   ||||||| :|||||||||||||||||||||||||||||||||||||||||||||||||
b  IYNKLDKGQIIVVIWVIVSPNNDKQKYTLKINHDCVPEQVIAEAIRKKTRSMLLSSEQLK
            190        200        210        220        230        240

250        260        270        280        290        300
h  LCVLEYQGKYILKVCGCDEYFLEKYPLSQYKYIRSCIMLGRMPNLKMMAKESLYSQLPMD
   |||||||||||||||| ||||||||||||||||||||||||||| ||||||||||||||
b  LCVLEYQGKYILKVCGCDEYFLEKYPLSQYKYIRSCIMLGRMPNLMLMAKESLYSQLPMD
            250        260        270        280        290        300

310        320        330        340        350        360
h  CFTMPSYSRRISTATPYMNGETSTKSLWINRALRIKILCATYVNLNIRDIDKIYVRTGI
   ||||||||||||||||||||||||||||||| ||||||||| :||||||||||||||||
b  CFTMPSYSRRISTATPYMNGETSTKSLWINSALRIKILCATYVNVNIRDIDKIYVRTGI
            310        320        330        340        350        360
```

FIG. 18C

```
              370         380         390         400         410         420
     h  YHGGEPLCDNVNTQRVPCSNPRWNEWLNYDIYIPDLPRAARLCLSICSVKGRKGAKEEHC
            |||||||||||||||||||||||||||||||||||||||||||||||||||||
     b  YHGGEPLCDNVNTQRVPCSNPRWNEWLNYDIYIPDLPRAARLCLSICSVKGRKGAKEEHC
              370         380         390         400         410         420

430         440         450         460         470         480
     h  PLAWGNINLFDYTDTLVSGKMALNLWPVPHGLEDLLNPIGVTGSNPNKETPCLELEFDWF
            |||||||||||||||||||||||||||||||||||||||||||||||||||||
     b  PLAWGNINLFDYTDTLVSGKMALNLWPVPHGLEDLLNPIGVTGSNPNKETPCLELEFDWF
              430         440         450         460         470         480

490         500         510         520         530         540
     h  SSVVKFPDMSVIEEHANWSVSREAGFSYSHAGLSNRLARDNELRENDKEQLKAISTRDPL
            ||||||||||||||||||||||||||||||||||||||||||||||||:||:|||||
     b  SSVVKFPDMSVIEEHANWSVSREAGFSYSHAGLSNRLARDNELRENDKEQLRAICTRDPL
              490         500         510         520         530         540
```

FIG. 18D

```
             550        560        570        580        590        600
h  SEITEQEKDFLWSHRHYCVTIPEILPKLLLSVKWNSRDEVAQMYCLVKDWPPIKPEQAME
   ||||||||||||||||||||||||||||||||||||||||||||||||||||||||||||
b  SEITEQEKDFLWSHRHYCVTIPEILPKLLLSVKWNSRDEVAQMYCLVKDWPPIKPEQAME
             550        560        570        580        590        600

610        620        630        640        650        660
h  LLDCNYPDPMVRGFAVRCLEKYLTDDKLSQYLIQLVQVLKYEQYLDNLLVRFLLKKALTN
   ||||||||||||||||||||||||||||||||||||||||||||||||||||||||||||
b  LLDCNYPDPMVRGFAVRCLEKYLTDDKLSQYLIQLVQVLKYEQYLDNLLVRFLLKKALTN
             610        620        630        640        650        660

670        680        690        700        710        720
h  QRIGHFFFWHLKSEMHNKTVSQRFGLLLESYCRACGMYLKHLNRQVEAMEKLINLTDILK
   ||||||||||||||||||||||||||||||||||||||||||||||||||||||||||||
b  QRIGHFFFWHLKSEMHNKTVSQRFGLLLESYCRACGMYLKHLNRQVEAMEKLINLTDILK
             670        680        690        700        710        720
```

FIG. 18E

```
              730        740        750        760        770        780
h  QERKDETQKVQMKFLVEQMRRPDFMDALQGLLSPLNPAHQLGNLRLKECRIMSSAKRPLW
   ||:||||||||||||||||||||||||||||||||||||||||||||:|||||||||||
b  QEKKDETQKVQMKFLVEQMRRPDFMDALQGFLSPLNPAHQLGNLRLEECRIMSSAKRPLW
              730        740        750        760        770        780

790        800        810        820        830        840
h  LNWENPDIMSELLFQNNEIIFKNGDDLRQDMLTLQIIRIMENIWQNQGLDLRMLPYGCLS
   ||||||||||||||||||||||||||||||||||||||||||||||||||||||||||||
b  LNWENPDIMSELLFQNNEIIFKNGDDLRQDMLTLQIIRIMENIWQNQGLDLRMLPYGCLS
              790        800        810        820        830        840

850        860        870        880        890        900
h  IGDCVGLIEVVRNSHTIMQIQCKGGLKGALQFNSHTLHQWLKDKNKGEIYDAAIDLFTRS
   ||||||||||||||||||||||||||||||||||||||||||||||||||||||||||||
b  IGDCVGLIEVVRNSHTIMQIQCKGGLKGALQFNSHTLHQWLKDKNKGEIYDAAIDLFTRS
              850        860        870        880        890        900
```

FIG. 18F

```
            910        920        930        940        950        960
h  CAGYCVATFILGIGDRHNSNIMVKDDGQLFHIDFGHFLDHKKKFGYKRERVPFVLTQDF
   ||||||||||||||||||||||||||||||||||||||||||||||||||||||||||
b  CAGYCVATFILGIGDRHNSNIMVKDDGQLFHIDFGHFLDHKKKFGYKRERVPFVLTQDF
            910        920        930        940        950        960

970        980        990       1000       1010       1020
h  LIVISKGAQECTKTREFERFQEMCYKAYLAIRQHANLFINLFSMMLGSGMPELQSFDDIA
   ||||||||||||||||||||||||||||||||||||||||||||||||||||||||||
b  LIVISKGAQECTKTREFERFQEMCYKAYLAIRQHANLFINLFSMMLGSGMPELQSFDDIA
            970        980        990       1000       1010       1020

1030       1040       1050       1060       1070       1080
h  YIRKTLALDKTEQEALEYFMKQMNDAHHGGWTTKMDWIFHTIKQHALNXKITEKMKAHSG
   |||||||||||||||||||||||||||||||||||||||||||||||||||
b  YIRKTLALDKTEQEALEYFMKQMNDAHHGGWTTKMDWIFHTIKQHALNX
           1030       1040       1050       1060
```

FIG. 19A

```
  1  MPPRPSSGEL WGIHLMPPRI LVECLLPNGM IVTLECLREA TLVTIKHELF
 51  KEARKYPLHQ LLQDESSYIF VSVTQEAERE EFFDETRRLC DLRLFQPFLK
101  VIEPVGNREE KILNREIGFA IGMPVCEFDM VKDPEVQDFR RNILNVCKEA
151  VDLRDLNSPH SRAMYVYPPH VESSPELPKH IYNKLDRGQI IVVIWVIVSP
201  NNDKQKYTLK INHDCVPEQV IAEAIRKKTR SMLLSSEQLK LCVLEYQGKY
251  ILKVCGCDEY FLEKYPLSQY KYIRSCIMLG RMPNLKMMAK ESLYSQLPMD
301  CFTMPSYSRR ISTATPYMNG ETSTKSLWVI NRALRIKILC ATYVNLNIRD
351  IDKIYVRTGI YHGGEPLCDN VNTQRVPCSN PRWNEWLNYD IYIPDLPRAA
401  RLCLSICSVK GRKGAKEEHC PLAWGNINLF DYTDTLVSGK MALNLWPVPH
451  GLEDLLNPIG VTGSNPNKET PCLELEFDWF SSVVKFPDMS VIEEHANWSV
```

FIG. 19B

```
501   SREAGFSYSH AGLSNRLARD NELRENDKEQ LKAISTRDPL SEITEQEKDF
551   LWSHRHYCVT IPEILPKLLL SVKWNSRDEV AQMYCLVKDW PPIKPEQAME
601   LLDCNYPDPM VRGFAVRCLE KYLTDDKLSQ YLIQLVQVLK YEQYLDNLLV
651   RFLLKKALTN QRIGHFFFWH LKSEMHNKTV SQRFGLLLES YCRACGMYLK
701   HLNRQVEAME KLINLTDILK QERKDETQKV QMKFLVEQMR RPDFMDALQG
751   LLSPLNPAHQ LGNLRLKECR IMSSAKRPLW LNWENPDIMS ELLFQNNEII
801   FKNGDDLRQD MLTLQIIRIM ENIWQNQGLD LRMLPYGCLS IGDCVGLIEV
851   VRNSHTIMQI QCKGGLKGAL QFNSHTLHQW LKDKNKGEIY DAAIDLFTRS
901   CAGYCVATFI LGIGDRHNSN IMVKDDGQLF HIDFGHFLDH KKKKFGYKRE
951   RVPFVLTQDF LIVISKGAQE CTKTREFERF QEMCYKAYLA IRQHANLFIN
1001  LFSMMLGSGM PELQSFDDIA YIRKTLALDK TEQEALEYFM KQMNDAHHGG
1051  WTTKMDWIFH TIKQHALN*
```

FIG. 20

```
  1  GGAGACGACTTGGACAGAGGATCAACTTATTCTTCAAATCATTTCACTC
     GlyAspAspLeuArgGlnAspGlnLeuIleLeuGlnIleIleSerLeu

49  ATGGACAAGCTGTTACGGGAAAGAAAATCTGGACTTGAAATTGACACCT
     MetAspLysLeuArgLysGluAsnLeuAspLeuLysLeuThrPro

97  TATAAGGTGTTAGCCACCAGTACAAAAACATGGCTTCATGCAGtTTATC
     TyrLysValLeuAlaThrSerThrLysHisGlyPheMetGlnPheIle

145  CAGTCAGTtCCTGTGGCTGAAGTTCTTGATACAGAGGAAGCATTCAG
     GlnSerValProValAlaGluValLeuAspThrGluGlySerIleGln

193  AACTTTTTAGAAAATATGCACCAAGTGAGAATGGGCCAAATGGGATT
     AsnPhePheArgLysTyrAlaProSerGluAsnGlyProAsnGlyIle

241  AGTGCTGAGGTCATGGACACTtACGTTAAAAGCTGTGCTGGATATTGC
     SerAlaGluValMetAspThrTyrValLysSerCysAlaGlyTyrCys

289  GTGATCACCTATATACTTGGAGTTGGAGACAGGCACCTGGATAACCTT
     ValIleThrTyrIleLeuGlyValGlyAspArgHisLeuAspAsnLeu

337  TTGCTAACCAAAACAGGCAAACTCTTCCACATCGATTTCGGCCAC
     LeuLeuThrLysThrGlyLysLeuPheHisIleAspPheGlyHis
```

FIG. 21

```
  1  GGGGATGACTTACGGCAGGACATGCTAACGCTGCAGATGATTCGCATC
     GlyAspAspLeuArgGlnAspMetLeuThrLeuGlnMetIleArgIle

49  ATGAGCAAGATCTGGGTCCAGGAGGGCTGGACACATGCGCATGGTCATC
     MetSerLysIleTrpValGlnGluGlyLeuAspMetArgMetValIle

97  TTCCGCTGCTTCTCCACCGGCCGGGGCAGAGGGATGGTGGAGATGATC
     PheArgCysPheSerThrGlyArgGlyArgGlyMetValGluMetIle

145  CCTAATGCTGAGACCCTGCTAAGATCCAGGTGGAGCATGGGGTGACc
     ProAsnAlaGluThrLeuArgLysIleGlnValGluHisGlyValThr

193  GGCTCGTTCAAGGACCGGCCCCTGGCAGACCGGCTGCAGAAACACAAC
     GlySerPheLysAspArgProLeuAlaAspArgLeuGlnLysHisAsn

241  CCTGGGGAGGACGAGTATGAGAAGGCTGTGGAGAACTTTATCTACTCC
     ProGlyGluAspGluTyrGluLysAlaValGluAsnPheIleTyrSer

289  TGCGCTGCTGCTGCTGGCCACTACGTCTTGGGCATCTGTGACga
     CysAlaGlyCysCysValAlaThrTyrValLeuGlyIleCysAspArg

337  CATAATGACAACATCATGCTGAAGACCACTGGTCACATGTTCCACATC
     HisAsnAspAsnIleMetLeuLysThrThrGlyHisMetPheHisIle

385  GACTTCGGC
     AspPheGly
```

FIG. 22

```
           1                                                    50
vps34      GDDLRQDqLvvQIIslMnellknEnvDLkLtPYkiLaTGpqeGaIEfIpN
PITR-c     GDDLRQDqLiLQIIslMdkllrkEnLDLkLtPYkvLaTstkhGFmqfIqs
hump110    GDDLRQDmLtLQIIriMeniwqnggLDLrMlPYgcLsiGdcvGLIEvVrN
PITR-f     GDDLRQDmLtLQmIriMskiwvqEgLDMrMviFrcFsTGrgrGMVEmIpN
Consensus  GDDLRQD-L-LQII--M-----E-LDL---PY--L-TG---G-IE-I-N 51                                                  100
vps34      dtlasilskyhGIlGy........LklhypdeNatlgVqgwvlDnFVkSCA
PITR-c     vpvaevldtegsIqnf........FrkYapseNgpngIsaevmDtYVkSCA
hump110    shtimqiqckgGlkGalqfnshtLhqWlkdkNkge.IydaaiDlFtrSCA
PITR-f     aetlrkiqvehGVtGs..fkdrpLadrlqkhNpgedeyekavEnFIySCA
Consensus  -------GI-G----------------N-----I------D-FV-SCA 101                                        133
vps34      GYCViTYILGVGDRHlDNlLvtpdGhFFHaDEG
PITR-c     GYCViTYILGVGDRHlDNlLltktGkLFHIDEG
hump110    GYCVaTFILGIGDRHnsNiMvkddGqLFHIDEG
PITR-f     GCCVaTYVLGIcDRHnDNiMlkttGhMFHIDEG
Consensus  GYCV-TYILG-GDRH-DN------G-LFHIDEG
```

POLYPEPTIDES HAVING KINASE ACTIVITY, THEIR PREPARATION AND USE

RELATED APPLICATIONS

This application is a divisional of Ser. No. 08/780,872, filed Jan. 9, 1997, now U.S. Pat. No. 5,846,824, which is a divisional of Ser. No. 08/162,081, filed Feb. 7, 1994, now U.S. Pat. No. 5,824,492,which is a national filing under 35USC § 371 of PCT/GB93/00761, filed Apr. 13, 1993.

This invention relates to new polypeptides which exhibit kinase activity. More specifically, the invention is concerned with polypeptides which show phosphoinositide (hereinafter "PI") 3-kinase activity, particularly molecules involved in pathways responsible for cellular growth and differentiation.

Major advances have taken place in our knowledge of the structure and function of the signal transducing molecules and second messenger systems coupled to cell surface receptors. Thus, a subset of polypeptide growth factor receptors belong to the family of protein-tyrosine kinases (hereinafter "PTK" and activation of these receptors following ligand binding involves autophosphorylation of the receptor as well as phosphorylation of a number of intracellular substrate proteins (reviewed in Ullrich, A et al., 1990). The importance of receptor autophosphorylation had been unclear until recently, when evidence from several laboratories has suggested that this event may mediate the formation of complexes between receptor proteins and putative growth regulatory proteins such as phospholipase PI3-kinase (Coughlin, S R et al, 1989). GTPase-activating protein (GAP) (Kaplan et al, 1990), the serine/theonine kinase Raf (Morrison et al, 1989), and members of the src-family of protein-tyrosine kinases (Kypta, R M et al., 1990) (reviewed in Cantley, L C et al., 1991).

The association of PI kinase activity with activated receptors is of particular interest since increased turnover of PI and its phosphorylated derivatives has been implicated in the action of hormones, growth factors and transformation of cells by DNA and RNA viruses (reviewed in Whitman, M et al., 1988; Cantley et al., 1991). Several species of PI kinase are known to exist, but up to now none of these enzymes have been characterised by cloning and expression and the demonstration of PI kinase activity. Fibroblasts contain at least two PI kinase activities which are distinguishable on the basis of their detergent sensitivity and kinetic properties (Whitman, M et al., 1987). These two activities were classified as Type I (inhibited by non-ionic detergents) and Type II (stimulated by non-ionic detergents and inhibited by adenosine). A third distinct species (Type III) has been identified in bovine brain but remains poorly characterised (Enderman, G et al., 1987). One species of PI kinase activity in particular has become of major interest in the search for second messenger systems linked to protein-tyrosine kinases because this activity was shown to co-immunoprecipitate with activated platelet-derived growth factor (PDGF) receptors (Kaplan, D R et al., 1987; Coughlin, S R et al., 1989) and with the polyoma middle T antigen/pp60$^{c-src}$ (mT:pp60$^{c-src}$) complex (Whitman, M et al., 1985). This activity has been shown to be due to a Type I PI kinase which produces novel inositol lipids phosphorylated at the D-3 position of the inositol ring (Whitman, M et al., 1988). More recently this enzyme has also been shown to associate with the CSF-1 receptor (Varticovski, L et al., 1989) kit (Lev et al, 1991), the epidermal growth factor (EGF) receptor (Bjorge et al, 1990), the PDGF a-receptor (Yu et al, 1991), the insulin receptor (Ruderman et al, 1990), the hepatocyte growth factor receptor, Met (Graziani et al, 1991), and with activated non-receptor protein-tyrosine kinases (Fukui & Hanafusa, 1989; Chan et al, 1990; Varticovski et al, 1991).

PI3 kinase activity has been closely linked to the presence of 81/85 kD proteins in these immunoprecipitates which can be phosphorylated on tyrosine residues by the associated protein-tyrosine kinase both in vitro and in vivo (Kaplan, D R et al., 1987; Courtneidge, S A et al., 1987; Cohen et al, 1990). Recently a 650 fold purification of PI3-kinase from bovine brain was described which, among other proteins present in the purest preparation, contained an 85 kD protein which was shown to be an in vitro substrate for the PDGF and EGF receptors (Morgan, S J et al., 1990). Using sequence information from tryptic peptides derived from this protein, two homologous bovine p85 proteins, denoted p85α and p85β (Otsu, M et al., 1991) have recently been cloned. Two other groups have independently cloned murine and human p85α homologues using different strategies (Escobedo, J A et al., 1991b; Skolnik, E Y et al., 1991). Both of these p85 proteins can be demonstrated to bind directly to phosphorylated PDGF receptor in vitro (Otsu, M et al., 1991; Escobedo, J A et al., 1991b). These proteins may function as the receptor binding subunits of the PI3-kinase since neither of them can be shown to encode intrinsic PI3-kinase activity when expressed in a variety of cell systems (Otsu, M et al., 1991; Escobedo, J A et al., 1991b). However, immunoprecipitation of $^{125}$I-labelled bovine brain PI3-kinase with antibodies raised against p85 proteins precipitates an 85 kD protein together with a second protein of molecular weight 110 kD (Otsu, M et al., 1991).

PI3-kinase is one of a growing number of potential signalling proteins which associate with protein-tyrosine kinases activated either by ligand stimulation or as a consequence of cell transformation. A common feature of all these proteins (apart from Raf), is that they contain one or more SH2 domains (src homology) (Koch, C A et al., 1991). Both p85α and p85β proteins contain two SH2 domains. Experiments from a number of laboratories have suggested that these domains may function by binding to peptide sequences usually phosphorylated on tyrosine residues, and thus mediate the complex formation which follows activation of protein-tyrosine kinases (Anderson et al, 1990; Meyer & Hanafusa, 1990; Moran et al, 1990; Matsuda et al, 1991; Meyer et al, 1991; reviewed in Koch, C A et al., 1991). In support of this, several studies suggest that tyrosine phosphorylation of the PDGF receptor or polyoma mT is essential for its association with proteins such as the PI3-kinase (Kazlauskas, A et al., 1989; Talmage, D A et al., 1989) GAP (Kaplan et al, 1990; Kazlauskas, A et al., 1990) and PLCγ (Anderson et al, 1990; Margolis et al, 1990). The precise tyrosine residue required for binding of the PI3-kinase activity (and an 85 kD phosphoprotein) to the human PDGF receptor has been mapped to tyrosine 751 which lies within the kinase insert region of the protein-tyrosine kinase domain (Kazlauskas & Cooper, 1989, 1990; Kazlauskas et al, 1991). The binding sites for other proteins to this receptor (eg., PLCγ, GAP and src-family kinases) have yet to be mapped, but these proteins may associate via other phosphorylated tyrosine residues.

This invention has been facilitated by the finding that certain synthesized peptides from the human PDGF β-receptor, namely peptides derived from the sequence around tyrosine 751 of the PDGF receptor, can be used to bind and isolate bovine brain PI3-kinase, making it possible to purify further partially purified bovine brain PI3-kinase (as described by Morgan et al, 1990) to apparent homogeneity and to obtain reasonably pure p110 protein. As will be described hereinafter, the PI3-kinase requires a phosphopeptide column containing a YXXM motif for its isolation by such a technique, the tyrosine being phosphorylated. Only if a column of this type is used are both the 85 kD and 110 kD proteins secured whereas 85 kD subunit binds to all phosphopeptide affinity columns tested and only fails to bind to non-phosphorylated peptides. Moreover, the relatively small size of the phosphopeptides used for such columns gives good specificity and a high density of affinity groups per unit volume of column.

This purification has allowed amino acid sequence information to be provided, and cDNA cloning to be performed. Such cloning has revealed some interesting facts. Thus, p110 is a 1068 amino acid protein having an unexpectedly high (compared to SDS-PAGE FIGS.) calculated molecular weight of about 124 kD (124247). The protein is related to Vps34p, a Saccharomyces cerevisiae protein involved in the sorting of proteins to the vacuole. Surprisingly, p110 when expressed in COS-1 cells was inactive and activity was only seen when complexed with p85. However, when expressed in insect cells, p110 could be shown to possess intrinsic kinase activity. The novel p110 polypeptide can be associated with p85α into an active p85α/p110 complex which binds the activated colony stimulating factor-1 receptor. The invention is also based upon these discoveries and unpredictable findings.

Thus, in one aspect the present invention provides an isolated polypeptide of calculated molecular weight approximately 124 kD which possesses PI3-kinase activity when produced by recombinant production in insect cells, or a polypeptide derivable therefrom which has PI3-kinase activity and binds, when associated with a p85 mammalian PI3 kinase subunit, to a phosphopeptide which includes the YXXM motif, the tyrosine being phosphorylated. Such polypeptides are preferably those capable of association with p85 subunits of mammalian PI3-kinases to produce active p85/p110 complexes. Preferably, the polypeptides have either the amino acid sequence of FIG. 9 hereof or exhibit significant sequence homology therewith. Preferred are polypeptides having at least amino acids 272 to 1068 of the seqeunce of FIG. 9 hereof.

As used herein, the term "PI3-kinase activity" means phosphoinositide-3 kinase activity.

The invention embraces polypeptides as defined and exhibiting sequence homology with any chosen mammalian species of PI3-kinase. A human sequence is given in FIG. 16 hereof. Amino acids 37(tyr)-834 (stop codon) (see FIG. 16) are >99% conserved with the bovine p110 cDNA sequence and correspond to amino acids 272–1069 (stop codon) of the sequence of FIG. 9. Upstream of amino acid 37 (human sequence) there is no sequence similarity between the p110 cDNA sequences from the two species.

The invention includes antibodies, monoclonal or otherwise, against the polypeptides of the invention.

In another aspect the invention includes a DNA sequence comprising either: (a) a sequence set out in FIG. 9 hereof; (b) any one of the subsequences A to N of FIG. 9 hereof; (c) the sequence represented by bases 816 to 3204 of FIG. 9 hereof; (d) a sequence set out in FIG. 16 hereof; or (e) a DNA sequence hybridizable to (a), (b), (c) or (d); which sequence (a), (b), (c), (d) or (e) encodes a polypeptide which has PI3-kinase activity if expressed in insect cells or can complex with a p85 mammalian PI3-kinase subunit to produce such activity. Subsequences A to N, referred to above, are themselves part of the present invention.

Hybridization conditions which may be used to find active sequences include, but are not limited to, 1 M NaCl/10× Denhardt's solution/50 mM Tri-HCl (pH 7.4)/ 10 mM EDTA/0.1% SDS/100 μg/ml denatured herring sperm DNA (Sigma) at 65° C. for 16 h, with the following washing conditions, i.e. 2×SSC/0.1% SDS, 42° C.→0.5×SSC/0.1% SDS, 50° C.→0.1×SSC/0.1% SDS, 65° C.→0.1×SSC/0.1% SDS, 68° C.

The invention further provides a DNA construct comprising a DNA sequence as defined above under the control of a control sequence and in proper reading frame in an expression vector.

The control sequence may include a regulatable promoter (e.g. Trp). Selected host cells which have been genetically altered to permit expression of the encoded polypeptide by the incorporation of such a construct are another aspect of the invention, and the invention also includes both a method of making such a polypeptide by cultivating such host cells and, of course, the resulting polypeptides.

In general, new polypeptides of the invention can be used to provide PI3-kinase activity, either directly or after complexing with a mammalian p85 subunit. Enzymatically active complexes involving the above-defined polypeptides are part of the invention.

The invention envisages a method of prophylaxis or therapy which involves the encouragement or discouragement of cell proliferation by the action of an agonist or antagonist, respectively, for the PI3-kinase activity of a polypeptide of the invention or complex including the same, wherein said cell proliferation is mediated through a cell surface receptor interactive with said activity. The present invention opens up for the first time, by providing pure sequenced active protein, the opportunity to screen (using standard techniques) for such agonists or antagonists.

Another aspect of the invention is a pharmaceutical or veterinary formulation comprising an agonist or antagonist as defined above formulated for pharmaceutical or veterinary use, respectively, optionally together with an acceptable diluent, carrier or excipient and/or in unit dosage form. Conventional pharmaceutical or veterinary practice may be employed to provide suitable formulations or compositions.

Thus, the formulations of this invention can be applied to parenteral administration, for example, intravenous, subcutaneous, intramuscular, intraorbital, ophthalmic, intraventricular, intracranial, intracapsular, intraspinal, intracisternal, intraperiotoneal, topical, intranasal, aerosol, scarification, and also oral, buccal, rectal or vaginal administration.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain as excipients sterile water or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the present factors. Other potentially useful parenteral delievery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, lactose or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The concentration of PI3-kinase agonist or antagonist in the formulations of the invention will vary depending upon a number of issues, including the dosage to be administered, and the route of administration.

In general terms, such agonists or antagonists may be provided in an aqueous physiological buffer solution containing about 0.1 to 10% w/v compound for parenteral administration. General dose ranges are from about 1 µg/kg to about 1 g/kg of body weight per day; a preferred dose range is from about 0.01 mg/kg to 100 mg/kg of body weight per day. The preferred dosage to be administered is likely to depend upon the type and extent of progression of the condition being addressed, the overall health of the patient, the make up of the formulation, and the route of administration.

The invention also includes the use of a polypeptide of the invention, or active complex containing the same, or an agonist or antagonist thereof in affecting the level of stimulation of platelets or neutrophils or in regulating blood glucose levels (the action of insulin may be mediated by PI3-kinase activity), and such use when employed for prophylactic or therapeutic purposes is envisaged.

The polypeptides of the invention (or complexes containing them) have a particular utility in the in vitro enzymatic production of 3-phosphorylated phosphoinositides eg PI(3)P, PI(3,4)P2, PI(3,4,5)P3). Such materials are of considerable biochemical interest, and are often very difficult to synthesize by conventional chemical techniques. This invention provides, for the first time, appreciable amounts of purified and reliable enzymatic activity for such in vitro synthesis.

In general, the first step in the purification and cloning upon which the invention is based involved partial purification of PI3-kinase from bovine brain as previously described (Morgan et al, 1990) and then further purification by affinity chromatography on an immobilised 17 amino acid phosphotyrosine peptide whose sequence is based on that surrounding tyrosine 751 of the human PDGF-β receptor. Following this final purification, p110 and p85 were eluted from the resin with SDS-containing buffers. The p85/p110 mixture was either digested directly with lysylendopeptidase, or p110 was further purified by SDS-agarose gel electrophoresis (see below) and digested following elution from the gel. Peptides were separated by reverse phase HPLC and sequenced using a modified Applied Biosystems 477A sequencer. Amino acid sequence analysis of 14 peptides (A to N, FIG. 9) generated 235 residues which could be assigned with certainty (see FIG. 9, attached).

It is important to note that the successful production of sequence information herein was dependent upon a novel SDS-agarose gel electrophoresis technique. Although, SDS-PAGE is widely used for high resolution protein separations, and is a method which resolves components primarily by their differences in molecular weight, as the polyacrylamide matrix is not readily disrupted, protein recovery following SDS-PAGE generally requires techniques involving electroelution from gel slices, electroblotting, or passive diffusion. Elution of proteins from polyacrylamide gels that have been previously stained using sensitive reagents (such as Coomassie Blue) is slow and recoveries are frequently low. Furthermore, these methods may concentrate impurities present in the polyacrylamide matrix and in the relatively large buffer volumes required for elution. Preparative SDS-PAGE systems using continuous flow collection have also been developed, but these frequently exhibit decreased resolution and low recoveries.

The novel method employed herein uses SDS-agarose gel electrophoresis (SDS-AGE) and allows a combination of the high resolving capacity of slab gel electrophoresis and the detection of proteins using sensitive stains with a rapid recovery technique that isolates proteins in high yield and in small volumes. The recovered protein is highly purified and in a form that can be either readily precipitated or digested directly in SDS containing buffers. Peptides produced by this method can be fractionated by HPLC and then analysed by automated amino acid sequencing. The recovery of long hydrophobic peptides is particularly efficient using these digestion conditions. The following protocol guides the skilled reader.

PROTOCOL

Materials

All chemicals should be of analytical or purer grades. Guanidinium hydrochloride was Aristar grade (BDH, UK). FMC Prosieve was purchased from Flowgen (UK) and ultrapure agarose was from BRL (USA). Other electrophoresis reagents were from Biorad (UK, Electrophoresis grade). Standard molecular weight proteins were from Bio-Rad (UK) and Amersham International (UK). Sequencing grade trypsin (porcine, EC 3.4.21.4) was from Boehringer Mannheim (UK) and lysylendopeptidase (Achromobacter lyticus, EC 3.4.21.50) was from Wako Chemicals GmbH (Germany). Glass capillaries were those supplied by Applied Biosystems Inc (USA) for use on the 430A HPEC system, but were frosted by abrasion with an aqueous carborundum suspension (C150 grade) and a steel rod. Frosted slab gel plates were obtained from Hoefer (UK).

Slab SDS-AGE

Slab Prosieve resolving gels of 0.75 or 1.5 mm thickness were poured essentially as described by the manufacturer using pairs of 16×18 cm glass plates, one of which was frosted in order to prevent the gel from slipping out of the electrophoresis assembly. It is important to ensure that the gel plates be thoroughly warmed to 60° C. prior to pouring the resolving gel. The inability to warm the gel plates prior to pouring an agarose stacking gel, the insertion of the comb into a rapidly cooling gel, and the removal of the comb from the fragile agarose stacking gel initially caused severe problems. In order to remove these difficulties a 5%T, 2.6%C polyacrylamide stacking gel was used in place of agarose in later preparations.

Samples were denatured at 100° C. in sample buffer (190 mM Tris/HCl, pH 6.8, 6% (w/v) SDS, 30% (v/v) glycerol, 10 mM DTT, 0.01% (w/v) bromophenol blue) and gels were run using Laemmli cathode buffer (0.192 M glycine, 0.025 M Tris, 0.1% (w/v) SDS) with a modified anode buffer (1M Tris/HCl, pH 8.3) at 200 v (approximately 50 mA for 1.5 mm and 25 mA for 0.75 mm gels) for about 4 h using a SE400 gel apparatus (Hoefer, USA). Gels were stained using either Coomassie Blue G-250 (Bio-Rad, UK) with rapid destaining or 4M ammonium acetate solution. In the latter case proteins were identified within a few minutes by optical contrast using incident light reflection observed against a dark background. Protein bands were immediately excised and gel slices stored at −20° C.

HPEC Electroelution

Gel slices were thawed and washed twice in 1 ml of 62.5 mM Tris/HCl, pH 6.8 for 5 min each at 20° C. Slices containing Coomassie Blue were prewashed with 1 ml of 50% (v/v) methanol, 5% (v/v) acetic acid for 5 min at 20° C.

The volume of the gel slice was estimated, then 10% SDS and 20% DTT were added to final concentrations of 2% and 0.2% (w/v) respectively. The gel slice was melted and homogenized by immersion in boiling water for 5 min with occasional mixing. The sample volume was then measured and made up to the required amount (see Table 1 below) with prewarmed 62.5 mM Tris/HCl, pH 6.8. The diluted sample was heated for a further 5 min and loaded into a prewarmed glass HPEC capillary. It was important not to exceed 90% of the capillary volume at this stage. The capillary was incubated at 4° C. for at least 10 min to allow the sample gel to solidify, before the slow addition of 0.8% agarose, 1 M Tris/HCl, pH 8.8 to overfill the capillary. After a further 10 min at 4° C., the ends of the gel were trimmed flush, sealed with Zytex discs, and applied to an Applied Biosystems 230A HPEC system. Electroelution was performed using an elution buffer pressure of 2.5 psi (generating a flow rate of approximately 1 µl/min), an upper reservoir buffer pressure of 3.5 psi and a lower reservoir buffer pressure of 0.9 psi. These settings were changed from the manufacturer's recommendations in order to stop the gel from collapsing upwards during the run. The current settings were as described in the text and 3 min fractions were collected while monitoring the eluate at 280 nm. The fraction collector rack was cooled to 4° C. and the gel compartment was cooled to 10° C.

TABLE 1

HPEC Elution Gel Parameters

| Capillary size (mm) | | Gel volume (µl)[a] | | | |
| --- | --- | --- | --- | --- | --- |
| Length | i.d.[a] | Total | Sample | Focussing | Current (mA) |
| 50 | 2.5 | 245 | 220 | 25 | 1.0–1.5 |
| 50 | 3.5 | 480 | 432 | 48 | 1.5 |
| 100 | 2.5 | 491 | 441 | 49 | 2.0–2.5 |
| 100 | 3.5 | 960 | 864 | 96 | 2.5 |

[a]These values are underestimated due to the variable increase in the internal diameter of the capillaries caused by the frosting procedure.

Preparation of Proteins for sequence Analysis

Fractions were assayed for protein content and purity either by monitoring radioactivity or by SDS-PAGE and silver staining. Samples required for trypsin or lysylendopeptidase digestion and subsequence sequence analysis were separated from Coomassie Blue by sequential precipitation on ice using 10% (w/v) TCA and then 20% TCA with centrifugation for 10 min at 4° C. Pellets were washed with 1 ml of acetone at –20° C. overnight and then washed again briefly in order to remove trace contamination by TCA and SDS before air drying and the addition of the required digestion buffer. Tryptic digestions were performed in 0.1 M Tris/HCl, pH 8.0 at 37° C. and lyslendopeptidase digestions in 20 mM Tris/HCl, pH 8.8 containing 0.1% (w/v) SDS at 30° C. Solid guanidinium hydrochloride was added to tryptic digests (6M final concentration) and incubated for 1 h at 37° C. Products were applied directly to HPLC columns using a Hewlett-Packard 1090M system and the effluent was monitored with a 79880A diode array detector. Trypsin digests were fractionated using an Applied Biosystems RP-300 column (2.1×100 mm) while lysylendopeptidase products required an Applied Biosystems AX-300 (2.1×30 mm) and an OD-300 column (2.1×100 mm) connected in series essentially as described by Kawasaki and Suzuki (1990).

The following Examples are given to illustrate the present invention without limiting the same. The Examples refer to the accompanying drawings. In the accompanying drawings:

Figures 1C, 1D:
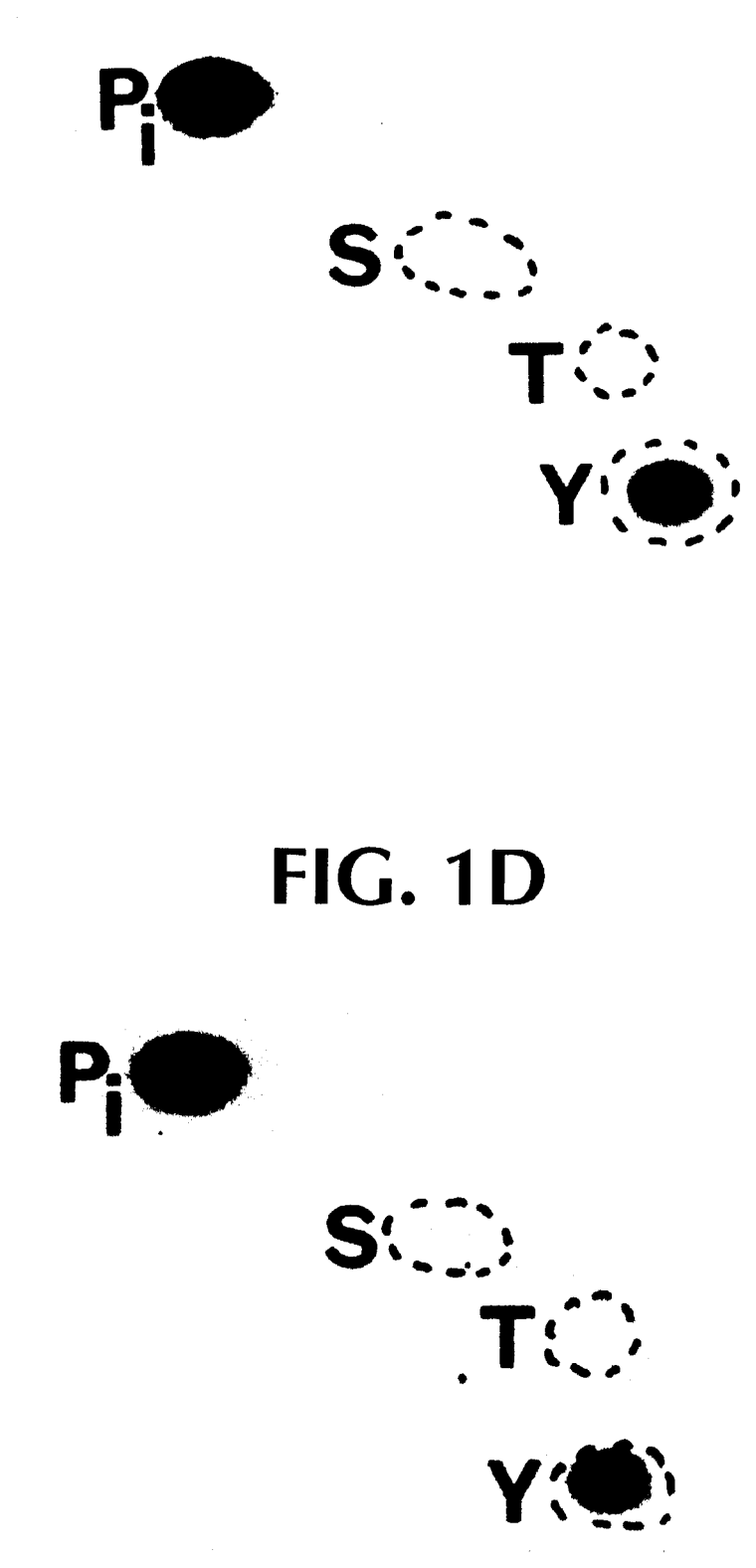

FIGS. 1 to 9 are concerned with Example 1, sections A and B.

FIGS. 1A–1D. Phosphorylation and purification of Y751 phosphopeptide.

Panel A. HPLC profile for separation of the phosphorylated from the non-phosphorylated Y751 peptide on a $C_{18}$ reverse phase column. The trace shows the spectra monitored at 214 nm during the course of the elution. The peaks corresponding to the phosphorylated and non-phosphorylated peptide are indicated by arrows. The small peaks observed are derived from the A431 membranes.

Panel B. Spectral analysis of the purified phosphorylated and non-phosphorylated Y751 peptides between 240 and 300 nm as measured by the diode-array detector. The absorption maximum for the peptide is observed to shift to a lower wavelength following tyrosine phosphorylation.

Panel C and D. Phosphoamino acid analysis of Y751 peptide phosphorylated by either purified EGF receptor (left panel) or A431 cell membranes (right panel). Following the phosphorylation reaction the phosphopeptide was purified by reverse phase HPLC. The peptide was subjected to acid hydrolysis and the phosphoamino acids separated by two-dimensional thin layer electrophoresis. Internal standards were stained with ninhydrin and the $^{32}$P-labelled phosphoamino acids were detected by autoradiography. The positions of inorganic phosphate ($P_i$), and phosphoserine (S), phosphothreonine (T) and phosphotyrosine (Y) standards are indicated.

Figure 2B:
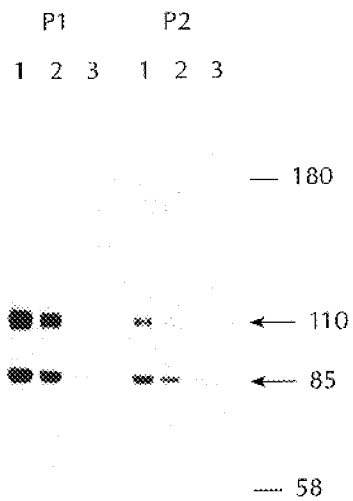

FIGS. 2A–2B. Purification of PI 3-kinase complex on the Y751 phosphopeptide affinity column.

Panel A. Peak 1 (P1) and peak 2 (P2) of PI 3-kinase fractions from the second MonoQ step were analysed on a 7.5% SDS-PAGE gel. Proteins in these two peak fractions were visualised by silver staining. The migration positions of molecular weight markers are indicated.

Panel B. Affinity purification of peak 1 (P1) and peak 2 (P2) PI 3-kinase using the Y751 phosphopeptide column. Silver stain of a 7.5% SDS-PAGE gel showing PI 3-kinase associated proteins from MonoQ P1 and P2 which bound to, and were eluted from, the Y751 phosphopeptide column with 0.1% SDS-containing phosphate buffer at 80° C. Lanes 1, 2 and 3 for both the P1 and P2 material indicates the proteins eluted by successive 50 µl elutions.

Figure 3:
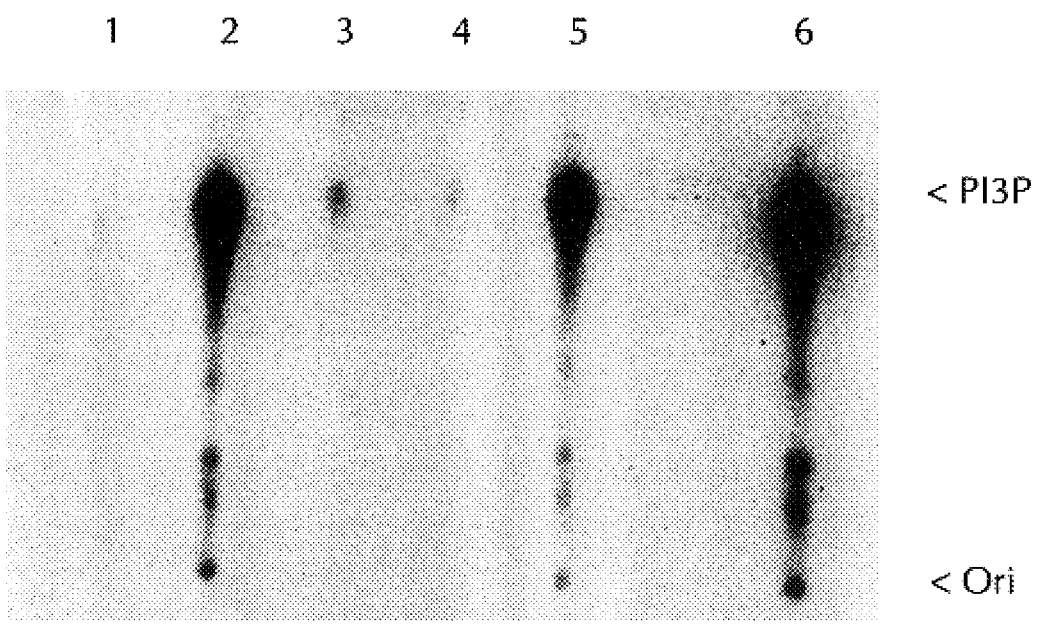
Figure 4C:
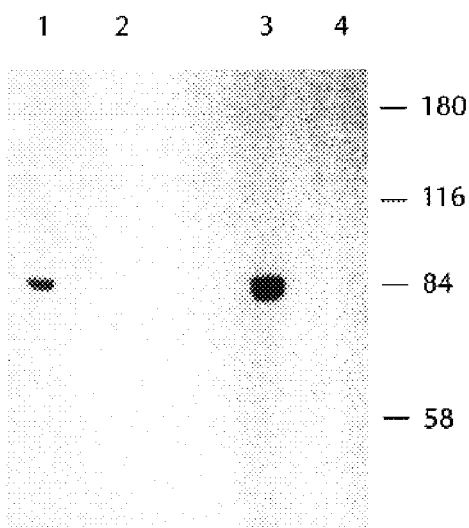
Figure 4D:
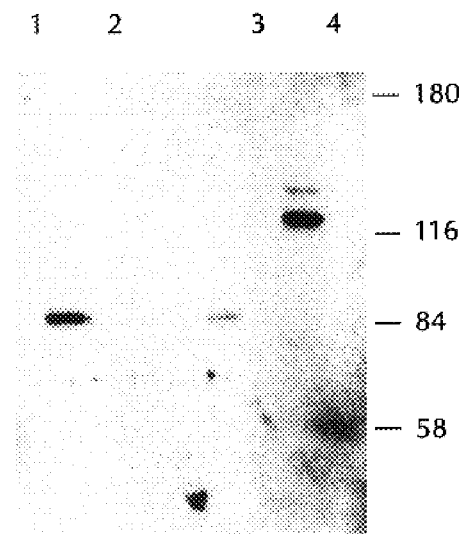

FIG. 3. Characterisation of the binding of PI 3-kinase activity to Y751 derived peptide columns.

One microgram of partially purified peak 1 bovine brain PI 3-kinase was applied to 10 µl of the Y751 derived peptide resins in 100 µl of binding buffer. Bound proteins were assayed for PI 3-kinase activity. Lane 1, PI 3-kinase activity bound to non-phosphorylated Y751 column. Lane 2, PI 3-kinase activity bound to phosphorylated Y751 column. Lane 3, PI 3-kinase activity removed from supernatant of column in lane 2 by fresh phosphorylated Y751 column. Lane 4, PI 3-kinase activity remaining associated with the column from lane 2 following removal of the bound material using 0.1% SDS at 80° C. Lane 5, PI 3-kinase activity bound to recycled phosphorylated Y751 column as used in lane 2 following addition of a fresh aliquot of bovine brain PI 3-kinase in binding buffer. Lane 6, Equivalent amount of peak 1 soluble bovine brain PI 3-kinase activity as applied to columns in lane 2 or lane 5.

FIGS. 4A–4D. Identify of p85 species in peak 1 and 2 of bovine brain PI 3-kinase preparation.

Protein samples were separated on 7.5% SDS-PAGE gels and transferred to nitrocellulose. The blots were then probed with antisera raised against the COOH-terminal peptide sequences of p85α or p85β.

Panel A. Western blot probed with anti-p85α COOH-terminal antisera.

Lane 1, peak 1 bovine brain PI 3-kinase; lane 2, peak 2 bovine brain PI 3-kinase; lane 3, Cos-1 cell lysate from pMT2 vector alone transfected cells; lane 4, Cos-1 cell lysate from pMT2p85α transfected cells; lane 5, Cos-1 cell lysate from pMT2p85β transfected cells; lane 6 Sf9 cell lysate containing p85α; lane 7, Sf9 cell lysate containing p85β Panel B. Western blot probed with anti-p85β COOH-terminal antisera.

Lanes are as described for panel A.

Panel C. Competition of peptides with antibodies in Western blots. Samples in lanes 1 and 2 were probed with p85α specific antiserum while samples in lanes 3 and 4 were probed with the p85β specific antiserum. Lanes 1 and 2. Sf9 cell lysate containing baculovirus expressed p85α. Lanes 3 and 4, Sf9 cell lysate containing baculovirus expressed p85β. In the odd numbered lanes the nitrocellulose was probed with specific antiserum alone. In the even numbered lanes the antiserum was competed with 100 μg/ml of p85α (lane 2) and p85β (lane 4) specific C-terminal peptides respectively.

Panel D. Anti p85β western blot of bound and soluble PI 3-kinase material after chromatography using the Y751 phosphopeptide column.

Peak 1 (P1) and peak 2 (P2) of bovine brain PI 3-kinase were immobilised on the Y751 phosphopeptide column. Material which did not bind was collected and then the resin was washed extensively. Bound proteins were eluted from the column with SDS-PAGE sample buffer. Bound and unbound proteins were separated by SDS-PAGE on a 7.5% gel and then transferred to nitrocellulose. The filter was then probed with anti-p85α COOH-terminal antisera and visualised with $^{125}$I Protein A-Sepharose. Lane 1, P1 bound material; Lane 2, peak 1 material which did not bind to column; Lane 3, peak 2 bound material; Lane 4, peak 2 material which did not bind to column.

Figure 5A:
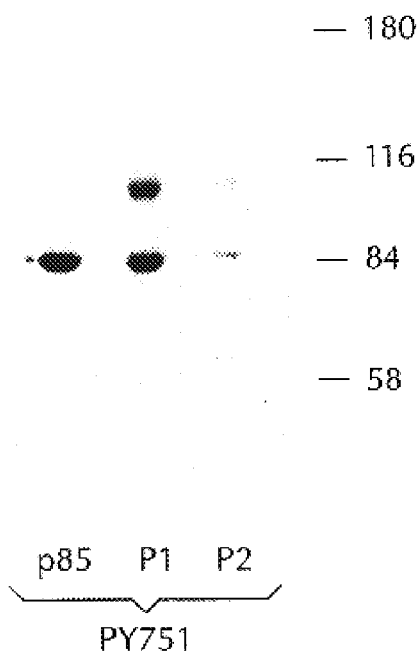
Figure 5B:
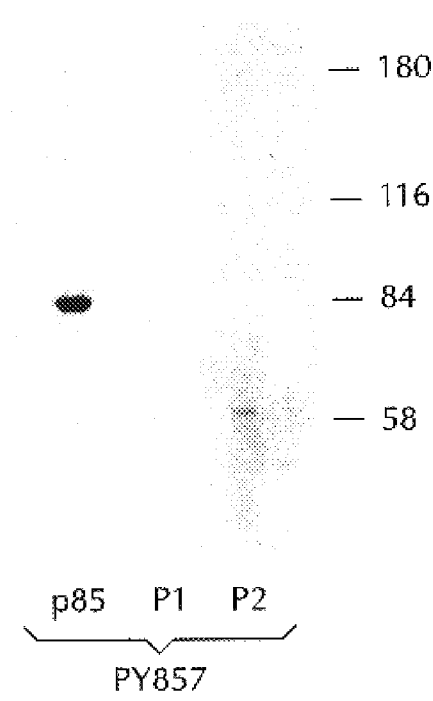

FIGS. 5A–5B. Specificity of binding of PI 3-kinase complex to Y751 peptide column:-comparison with Y857 phosphopeptides.

Sf9 cell lysates containing p85α proteins or one microgram of partially purified bovine brain PI 3-kinase (P1 and P2 MonoQ) was allowed to bind to the columns for 4 h at 4° C. as described. The columns were then washed repeatedly with binding buffer, bound proteins were eluted with SDS-containing buffers and then analysed by electrophoresis on 7.5% SDS-PAGE gels. Bound proteins were visualised by silver staining. Panel A. Proteins bound to Y751 phosphopeptide column. Panel B. Proteins bound to Y857 phosphopeptide column. The migration position of molecular weight markers are indicated.

Figure 6A:
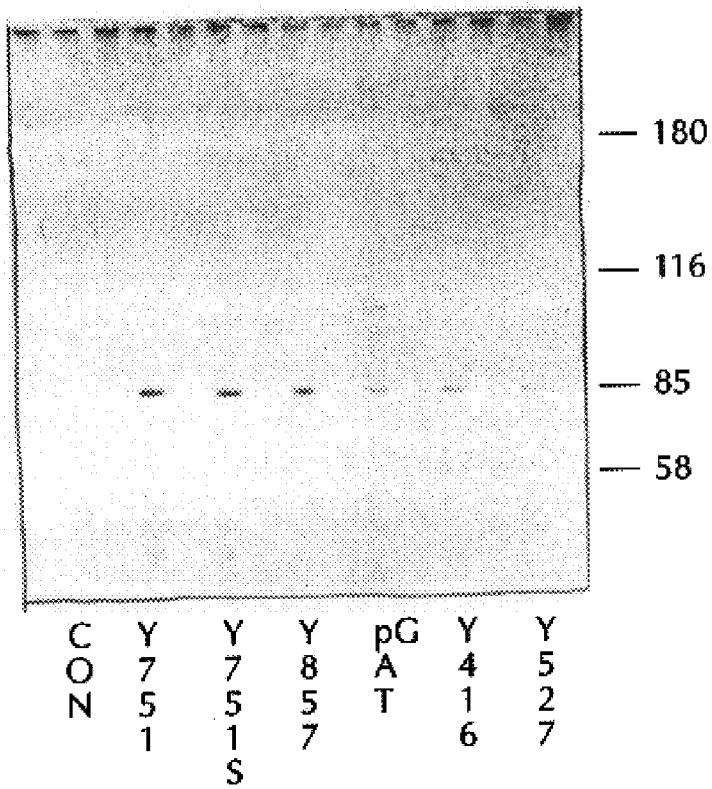
Figure 6B:
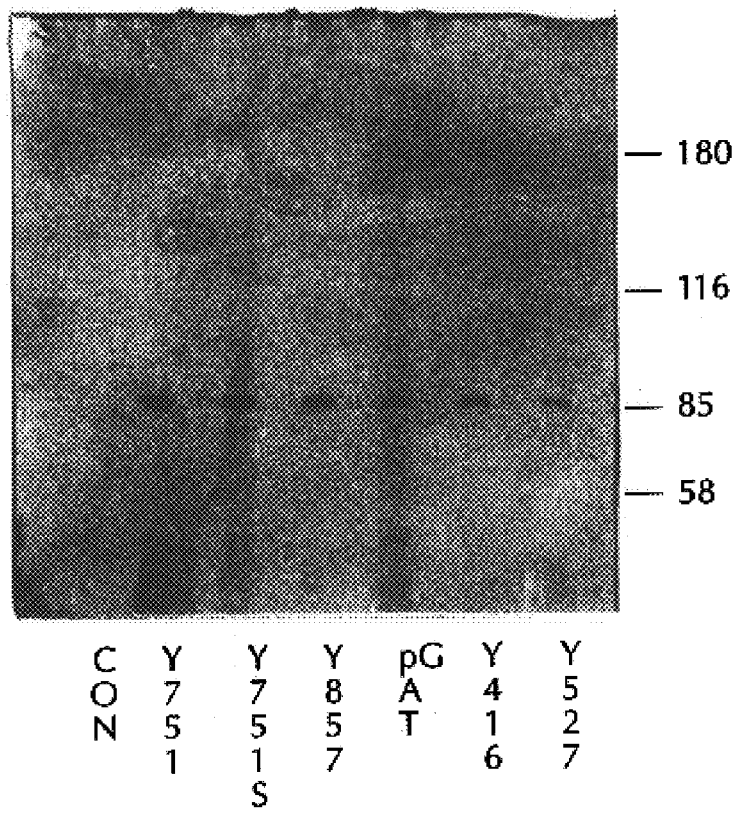

FIGS. 6A–6B. Binding of recombinant baculovirus expressed p85 proteins to a panel of phosphopeptide columns.

P85 proteins in SF9 cell lysates were tested for their ability to bind to the various peptide column. After extensive washing, bound proteins were eluted from the columns, separated on 7.5% SDS-PAGE gels and the visualised by staining with Coomassie Blue. Panel A. Bound p85α. Panel B. Bound p85β. CON, 17 amino acid non-phosphorylated Y751 column; Y751, 17 amino acid phosphopeptide from the kinase insert region of the PDGF β-receptor; Y751.S, 11 amino acid version of Y751 phosphopeptide; Y857, 17 amino acid phosphopeptide derived from the sequence around the second major tyrosine phosphorylation site in the PDGF β-receptor; pGAT, poly Glu:Ala:Tyr phosphopeptide; Y416 and Y527, 13 and 16 amino acid phosphopeptides derived respectively from the two major tyrosine phosphorylation sites of pp60$^{c-src}$.

Figure 7A:
Figure 7B:
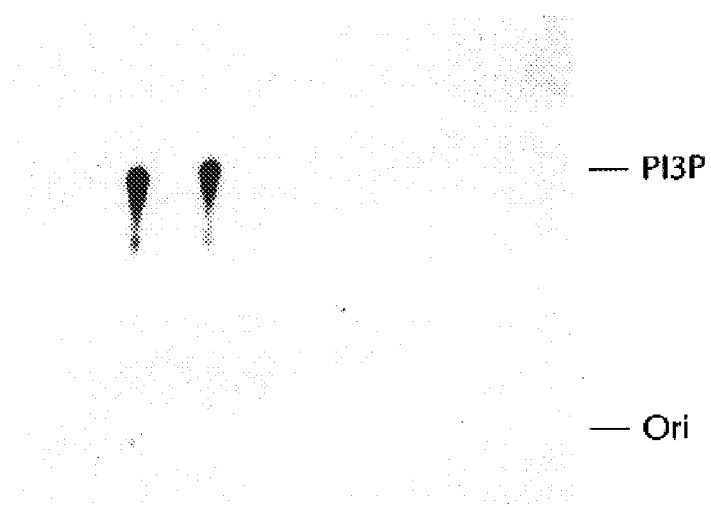

FIGS. 7A and 7B. The p85/100 complex and PI 3-kinase activity show specificity in the range of phosphopeptides to which they will bind.

One microgram of partially purified bovine brain PI 3-kinase (P1 MonoQ) was allowed to bind to peptide affinity columns for 4 h at 4° C. as described. The columns were then washed repeatedly with binding buffer. Bound proteins were then either eluted with SDS-containing buffers and then analysed by electrophoresis on 7.5% SDS-PAGE gels or assayed for PI 3-kinase activity bound to the column.

Panel A. Bound proteins were visualised by silver staining. The migration of molecular weight markers is indicated.

Panel B. PI 3-kinase activity bound to various phosphopeptide columns. The $^{32}$P-labelled lipid products were separated by TLC and the visualised by autoradiography. PI3P indicates the migration position of a PI3P standard. Ori indicates the origin of the TLC plate.

Figures 8A, 8B:
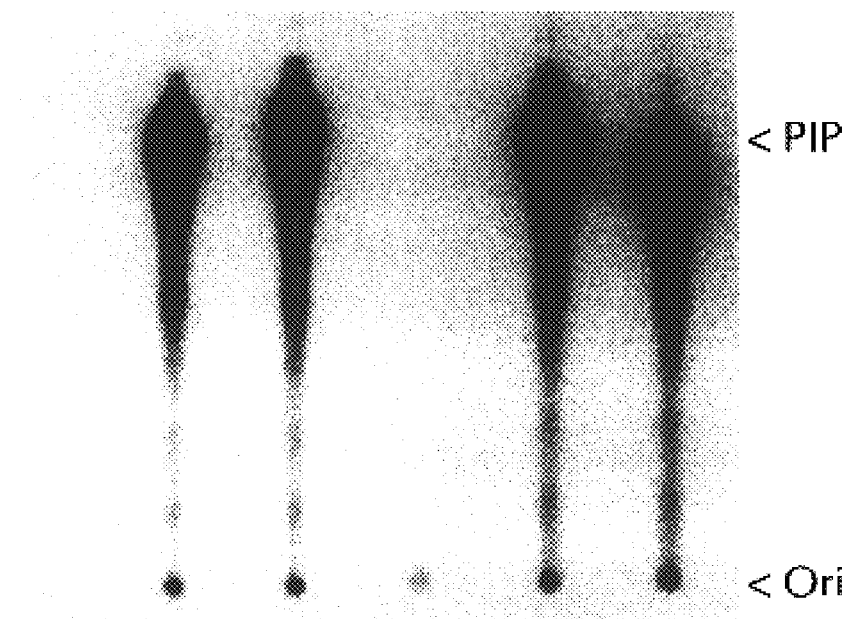

FIGS. 8A and 8B. Binding of PI 3-kinase activity of phosphopeptides containing the YXXM motif.

Panel A. One microgram of partially purified peak 1 bovine brain PI 3-kinase was bound to 10 μl of the indicated peptide columns. Following extensive washing the columns were assayed for bound PI 3-kinase activity. Lane 1, PI 3-kinase activity bound to non-phosphorylated Y751 column; Lane 2, PI 3-kinase activity bound to phosphorylated Y751 column; Lane 3, PI 3-kinase activity bound to phosphorylated Y751.S column; Lane 4 PI 3-kinase activity bound to phosphorylated Y857 column; Lane 5, PI 3-kinase activity bound to phosphorylated Y740 column;

Lane 6, PI 3-kinase activity bound to phosphorylated Met Y1313 column. PIP indicates the migration position of a PI4P standard. Ori indicates the origin of the TLC plate.

Panel B. Comparison of identified PI 3-kinase binding sites in the peptides tested. The proposed consensus sequence for binding is also shown for comparison (Cantley et al., 1991).

FIGS. 9 to 15 are concerned with Example 1, sections C and D, and FIGS. 16 to 25 relate to Example 2.

FIGS. 9A–9H. Nucleotide Sequence and Deduced Amino Acid sequence of p110.

The nucleotide sequence of the coding region and the deduced amino acid sequence in one letter code are shown. Peptide sequences (lettered from A–N) obtained by protein sequencing are highlighted.

Figure 9I:
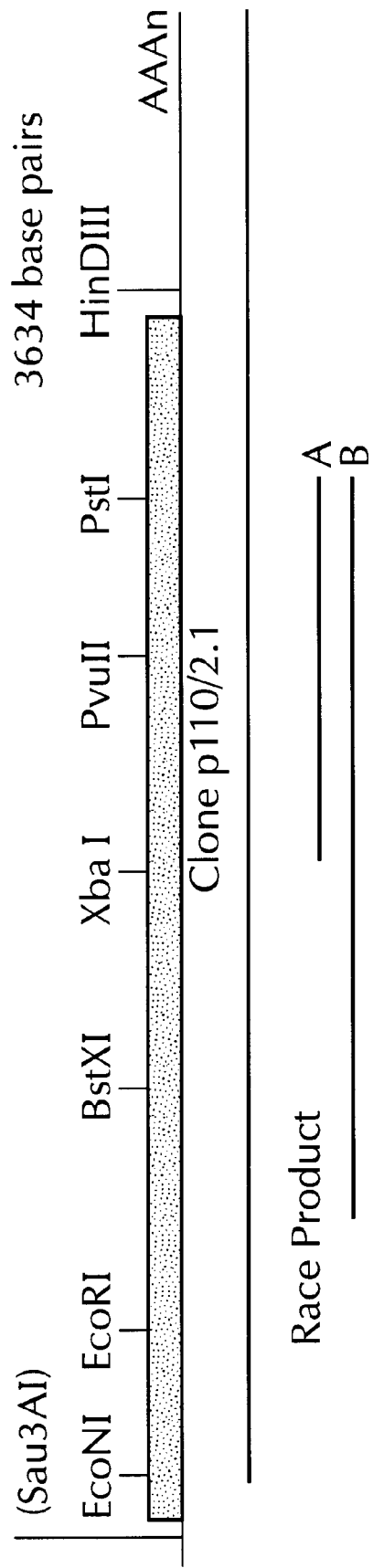
Figure 10A:
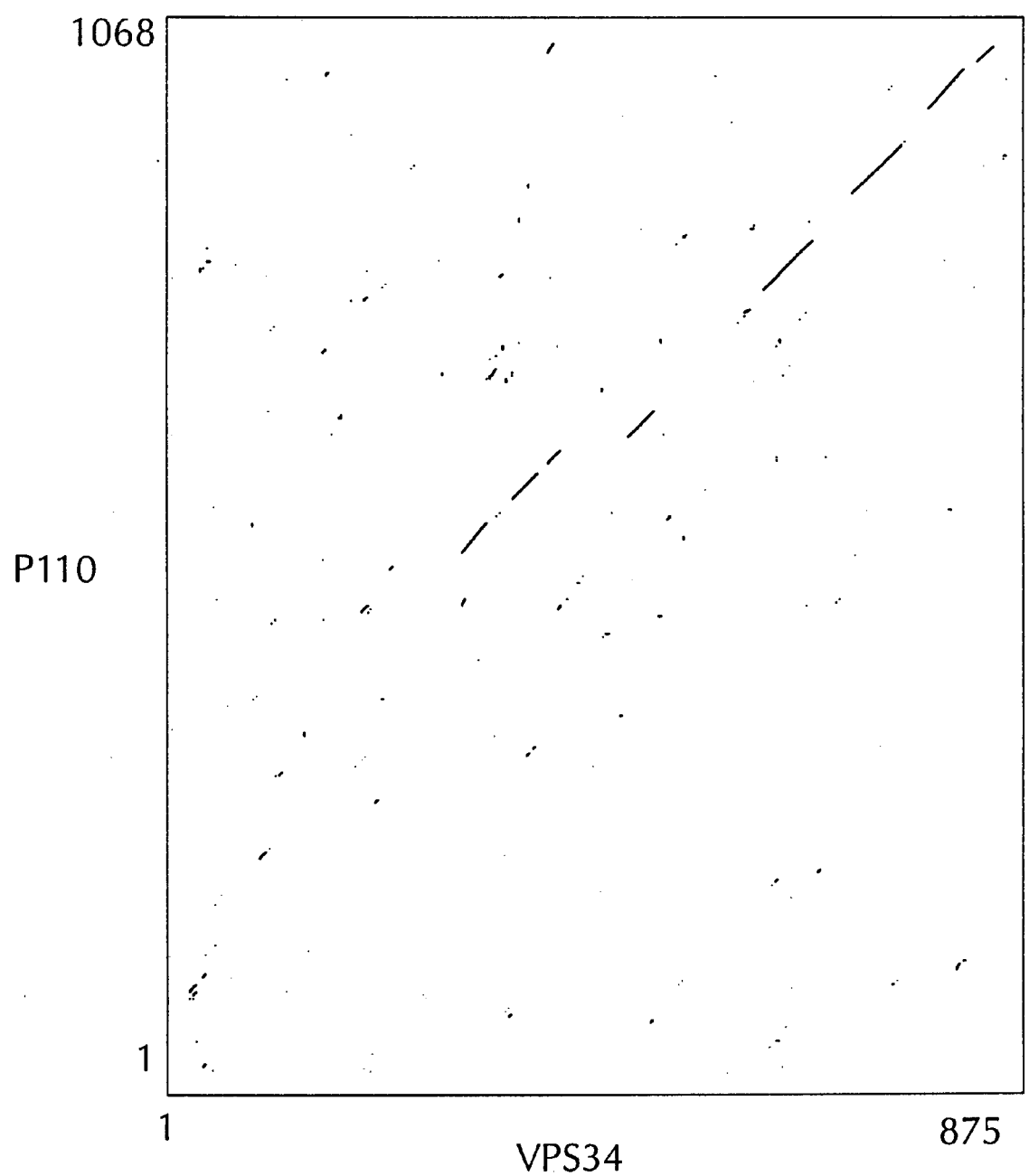

FIG. 9I Schematic representation of the p110 CDNA. The bold line indicates coding sequence. (p2.1): extent of clone p2.1, (Race Product): region amplified by RACE PCR, (a):

probe used in Southern blot analysis, (b): probe used in northern blot analysis, (S): Sau3AI site changed to BamHI site for expression in Sf9 cells.

FIGS. 10A–10D. Comparison of p110 and Vps34p Protein Sequences (A) Dot plot comparison of Vps34p (875 amino acids: horizontal axis) and p110 (1068 amino acids: vertical axis) using the Compare program (UWGCG package; Devereux et al., 1984).

(B–D) The optimal alignment of p110 (upper sequence) and Vps34p (lower sequence) over the region of homology, using the Gap program (UWGCG package: Devereux et al., 1984). Identical residues are indicated by (I), conserved residues are indicated by (:). Residues proposed to be involved in ATP binding are marked with (*).

Figure 11A:
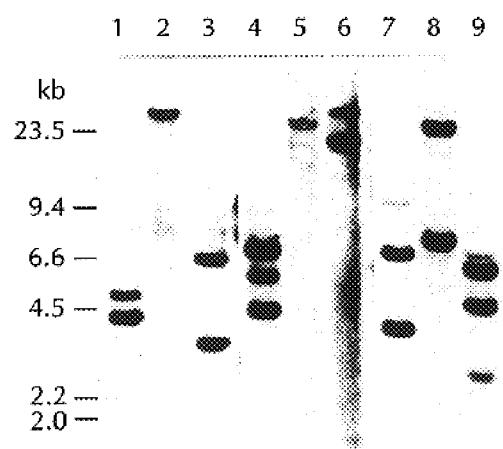
Figure 11B:
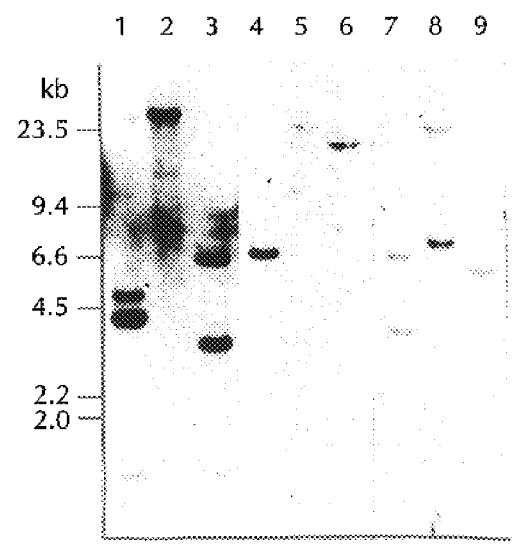

FIGS. 11A and 11B. Genomic Southern Analysis of p110

High molecular weight DNAs (3 μg) of bovine (lanes 1, 2, 3), human (lanes 4, 5, 6) and rat (lanes 7, 8, 9) origin were digested with EcoRI (lanes 1, 4, 7), BamHI (lanes 2, 5, 8) of Hindlll (lanes 3, 6, 9), fractionated through a 0.5% agarose gel and transferred to a nitrocellulose membrane as described in Example 1. The filter was probed with a $^{32}$P-labelled XbaI-PstI fragment (probe a in FIG. 9, lower panel). The filter was washed in 0.5×SSC, 0.1% SDS at 50° C. and exposed overnight (Panel A). The filter was then washed in 0.1×SSC, 0.1% SDS at 68° C. and exposed for seven days (Panel B). The marker track shows the positions of lambda Hindlll markers.

Figure 12A:
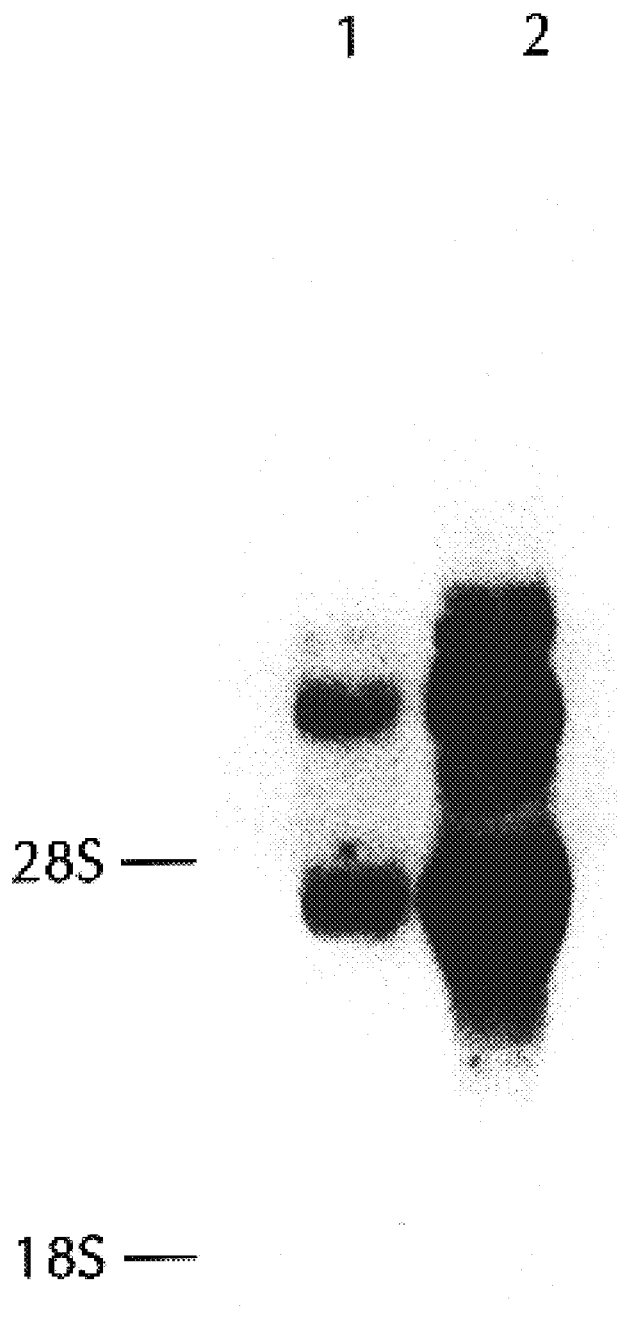
Figure 12B:
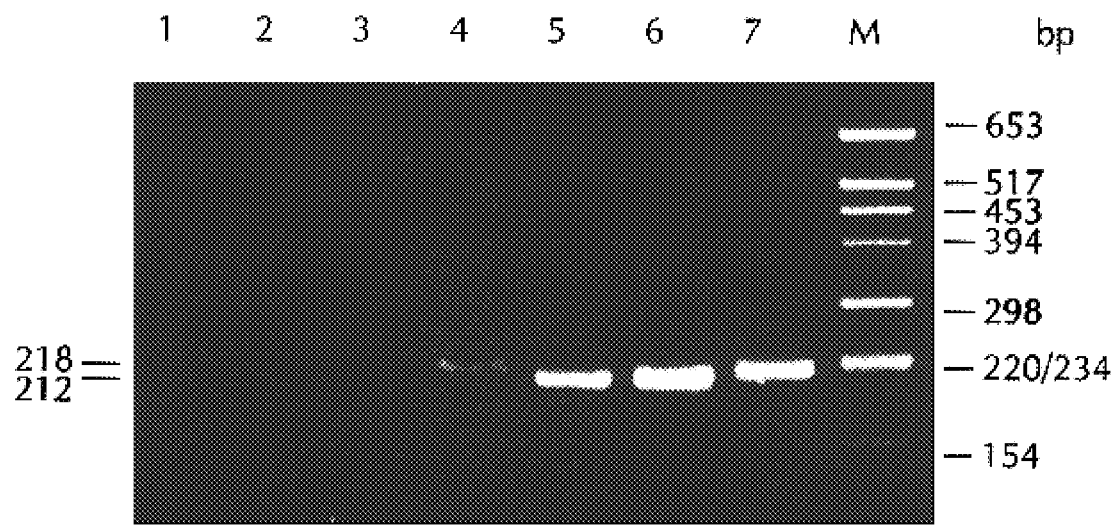
Figure 12C:
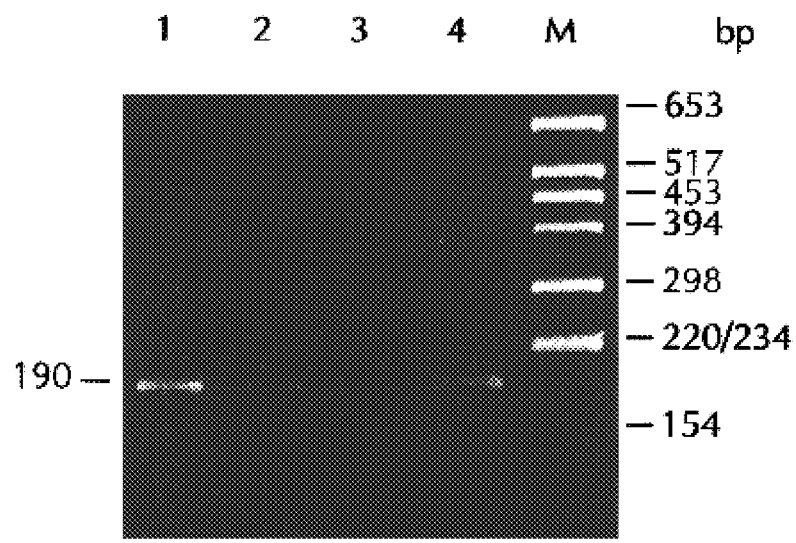

FIGS. 12A–12C. Analysis of Tissue Distribution of p110 Message (A) Northern Blot Analysis of p110 5 μg of poly(A) $^+$RNA isolated from total bovine brain (lane 1) or the SGBAF-1 cell line (lane 2) were fractionated on a 0.9% agarose gel and immobilised on membranes as described in Example 1. The filter was probed with a $^{32}$P labelled antisense RNA probe (probe b in FIG. 9, lower panel). After washing in 0.1×SSC, 0.1% SDS at 60° C., the filter was treated with 1 μg ml$^{-1}$ RNAase A and autoradiographed overnight.

(B) PCR Analysis to Detect p110 Transcripts Poly(A)$^+$ RNA was isolated from various sources and PCR performed as described in Example 1. Bands of 218 bp and 212 bp indicate the specific amplification of human and bovine transcripts, respectively. Lane 1; Human T-cell blasts, lane 2; Human peripheral blood acute lymphocytic leukaemia cells, lane 3; A431 cells (Human), lane 4; COS-1 cells (Simian), lane 5; bovine brain, lane 6; SGBAF-1 cells (Bovine), lane 7; ZNR cells (Porcine).

(C) PCR Analysis to Detect p85α Transcripts Poly (A)$^+$ RNA was isolated from various sources and PCR performed. Specific amplification of p85α message gives a bind of 190 bp. Lanes are the same as indicated for (B).

Figure 13A:
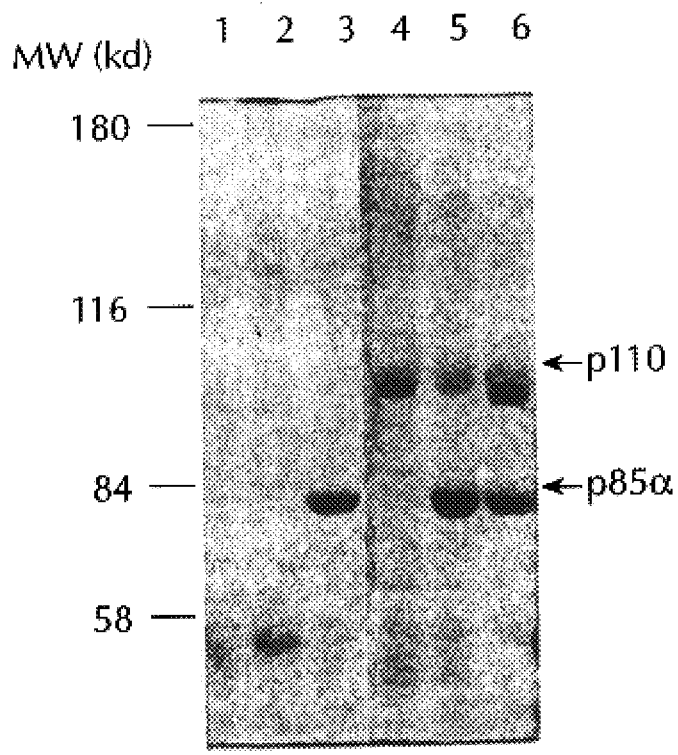
Figure 13B:
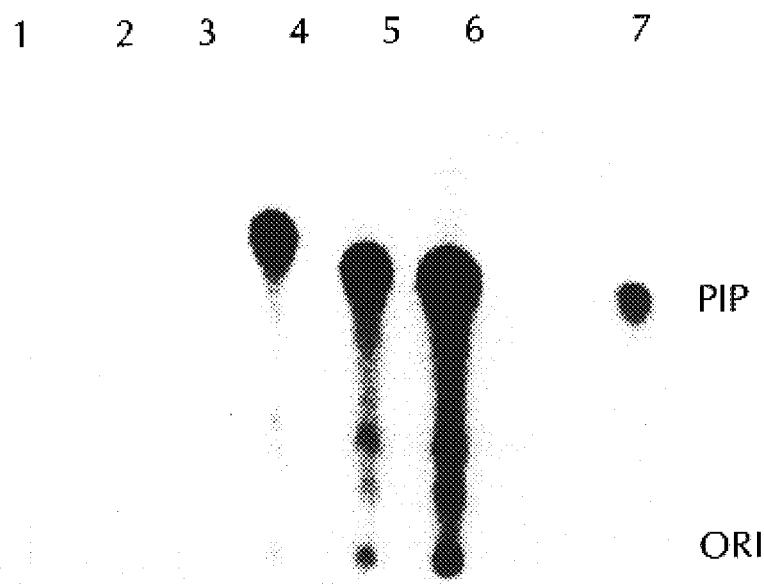

FIGS. 13A and 13B. Expression of p85α and p110 in Sf9 Cells Using Baculovirus Vectors (A) Sf9 cells were infected with a wild type baculovirus (lanes 1 and 2) or with baculoviruses expressing p85α (lane 3), p110 (lane 4) or p85α and p110 (lanes 5 and 6). Immunoprecipitates were prepared with either anti-p85α (lanes 1, 3, and 5) or anti-p110 antisera (lanes 2, 4 and 6), samples fractionated on a 7.5% SDS-PAGE gel and visualised by staining with Coomassie blue.

(B) PI3-kinase assays were performed on Immmunoprecipitates of p85α and p110 expressed in Sf9 cells. lanes 1–6 the same as Panel (A); lane 7: pI3-kinase activity from 1 μl of the partially purified bovine brain PI3-kinase preparation.

Figure 14A:
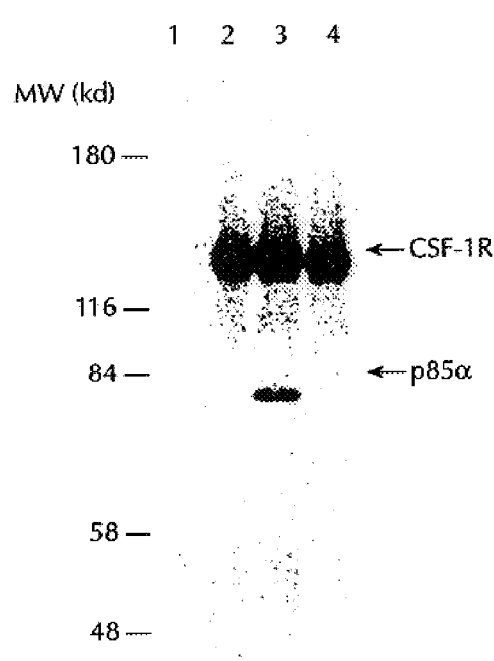
Figure 14B:
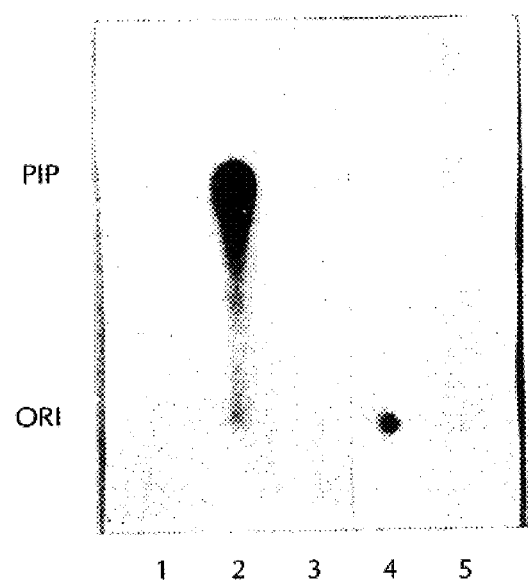

FIGS. 14A and 14B. In Vitro Association of PI3-Kinase Activity with the CSF-1 Receptor An in vitro PI3-kinase assay was performed on anti-CSF-1 receptor immunocomplexes prepared from Sf9 cells infected with a baculovirus expressing the CSF-1 receptor and treated as follows; lane 1: anti-CSF-1 receptor immunoprecipitates, untreated; lane 2; anti-CSF receptor immunoprecipitate, pre-treated with ATP and incubated with a p85α/p110 containing Sf9 cell lysate; lane 3: anti-CSF-1 receptor immunoprecipitate, treated in the absence of ATP and incubated with a p85α/p110 containing Sf9 cell lysate; lane 4: anti-CSF-1 receptor immunoprecipitate, pre-treated with ATP and incubated with a p85α containing Sf9 cell lysate; lane 5; anti-CSF-1 receptor immunoprecipitate, pre-treated with ATP and incubated with a p110 containing Sf9 cell lysate.

FIGS. 15A–15D. Expression of p85α and p110 in COS-1 Cells

COS-1 cells were transfected with 5 μg of the respective DNAs and harvested 48 h later. Transfected cells were labelled with 100 μCi ml$^{-1}$ of $^{35}$S-methionine for the last 4 h of this period. Immunoprecipitations were performed with either an p85α polyclonal antiserum or a p110 C-terminal peptide antiserum. After washing, the pellet was divided in two and half was then analyses on a 10% SDS-PAGE gel while the other half was subjected to PI3-kinase assay.

(A) $^{35}$S-labelled proteins immunoprecipitated with anti-p85α antiserum.

(B) PI3-kinase activity immunoprecipitated with anti-p85α antiserum.

(C) $^{35}$S-labelled proteins immunoprecipitated with 110 C-terminal peptide antiserum.

(D) PI3-kinase activity immunoprecipitated with 110 C-terminal peptide antiserum.

Lanes contain results from COS-1 cells transfected with the following DNAs; lane 1: vector DNA, lane 2: pMT2-p85α, lane 3: pSG5-p110, lane 4: pMT2-p85α and pSG5-110, lane 5 in panels B and D show the PI3-kinase activity immunoprecipitated with the two antisera from 1 μl of the partially purified bovine brain PI3-kinase preparation. The exposure times for panels A and C, and B and D are identical.

FIGS. 16A–16R. CDNA for human p110

The FIG. shows the sequence of human p110 CDNA, together with the corresponding amino acid sequence.

FIGS. 17A–17M. A comparison of the human p110 sequence and bovine p110 sequence at the DNA level.

FIGS. 18A–18F. A comparison of the human p110 sequence and bovine p110 sequence at the protein level.

FIGS. 19A and 19B. The protein sequence of human p110.

FIG. 20. The sequence of a CDNA related to p110, PITR-c.

FIG. 21. The sequence of a cDNA related to p110, PITR-f.

FIG. 22. The alignment of human p110, PITR-c, PITR-f and the yeast PI3-kinase VPS34.

Figure 23A:
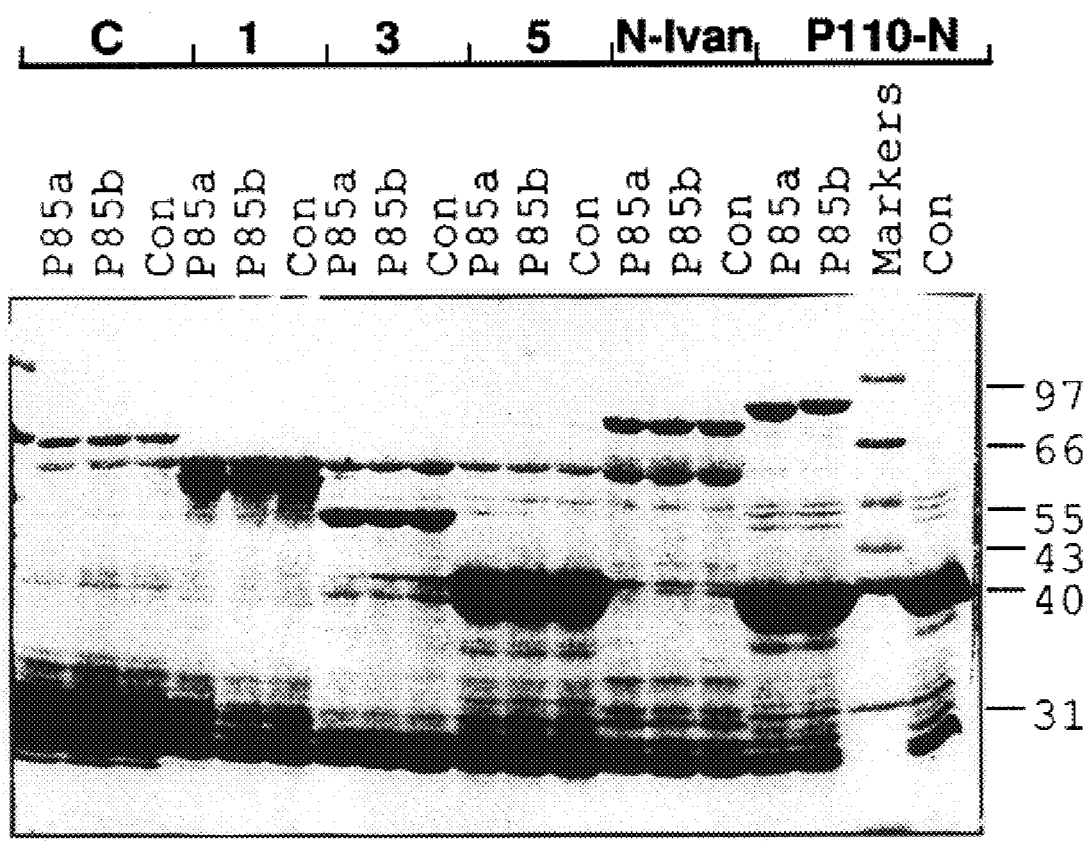

FIG. 23A. SDS PAGE analysis of proteins able to bind to various domains of human p110.

Figure 23B:
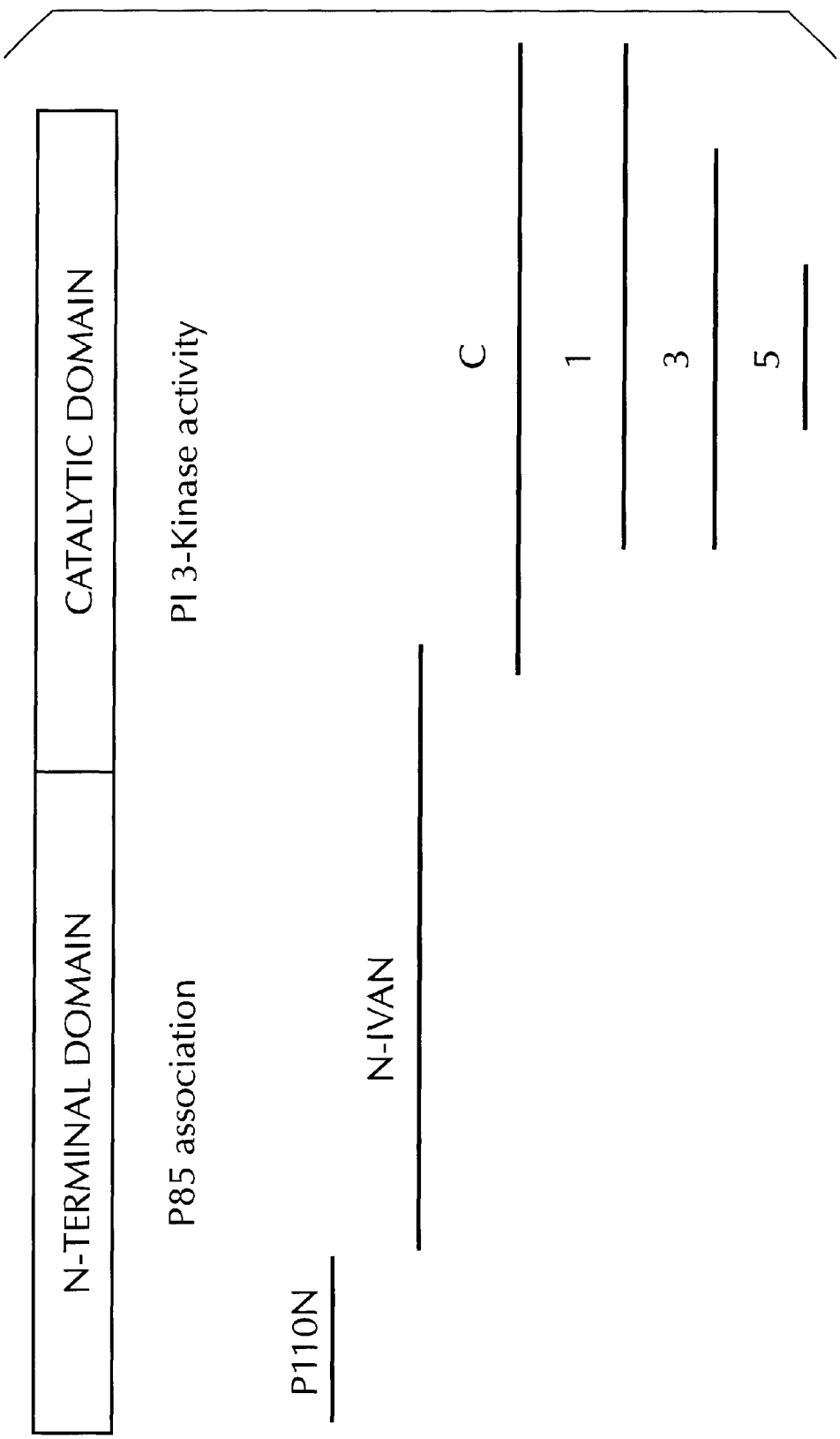

FIG. 23B. Schematic representation of the domains of p110 analysed for their ability to bind p85.

Figure 24:
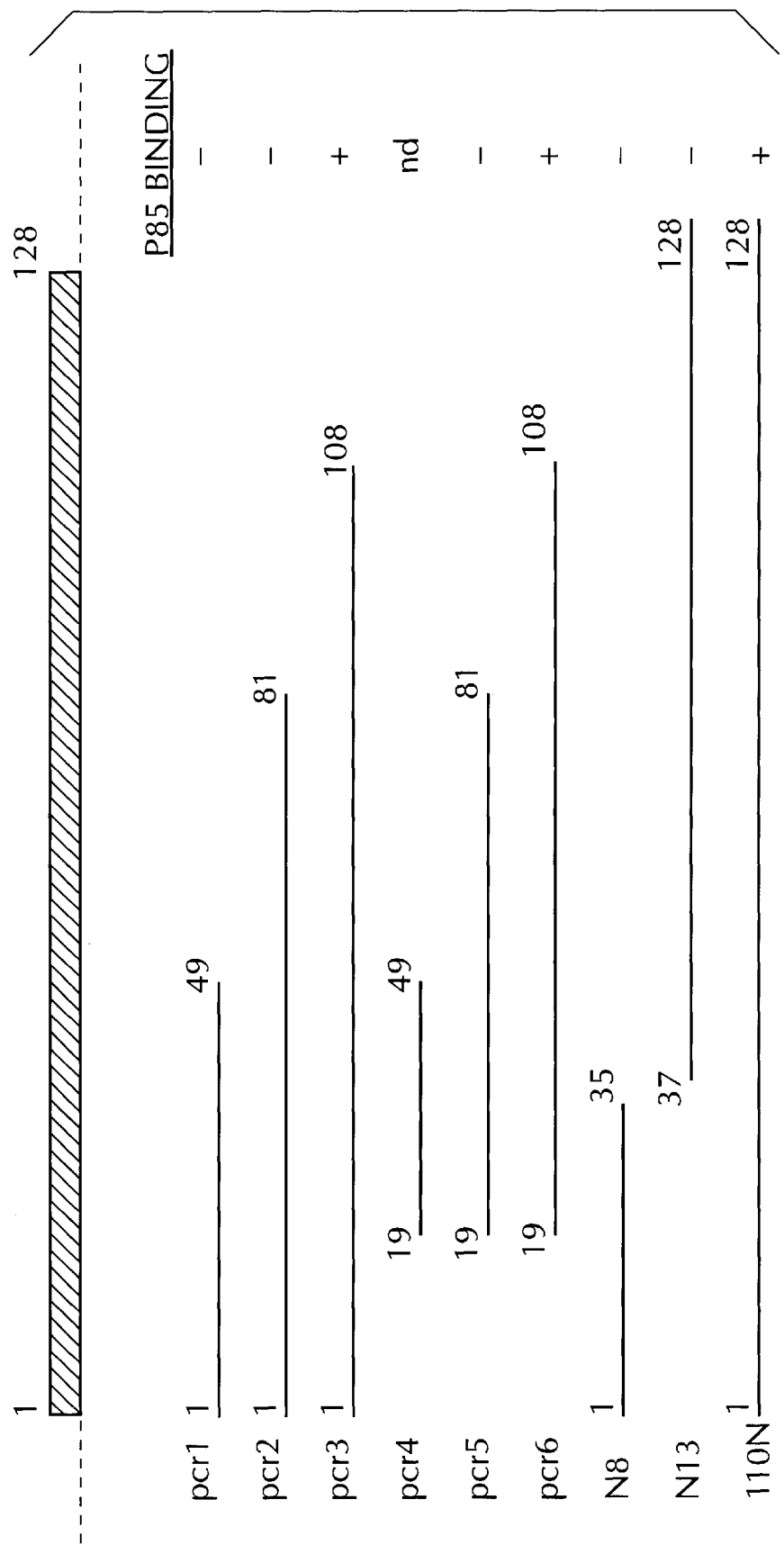

FIG. 24. Various deletion mutants and PCR fragments of p110 fragment p110-N.

Figure 25A:
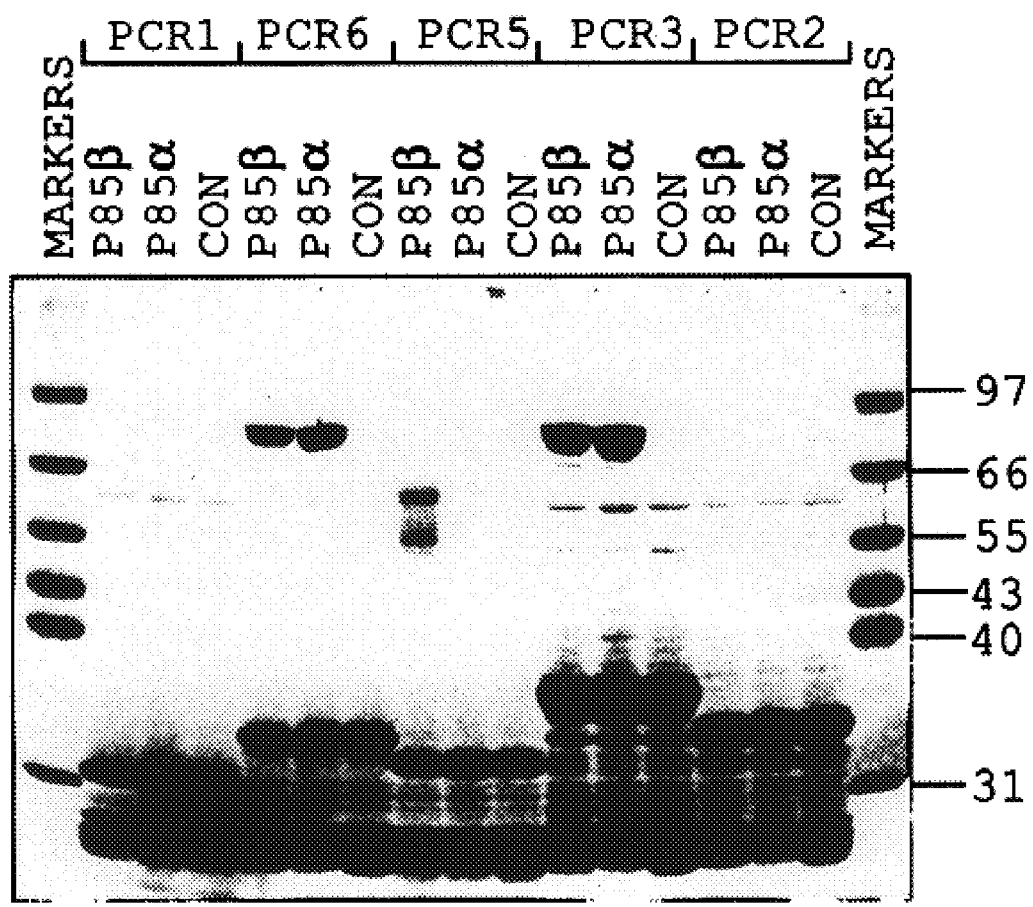
Figure 25B:
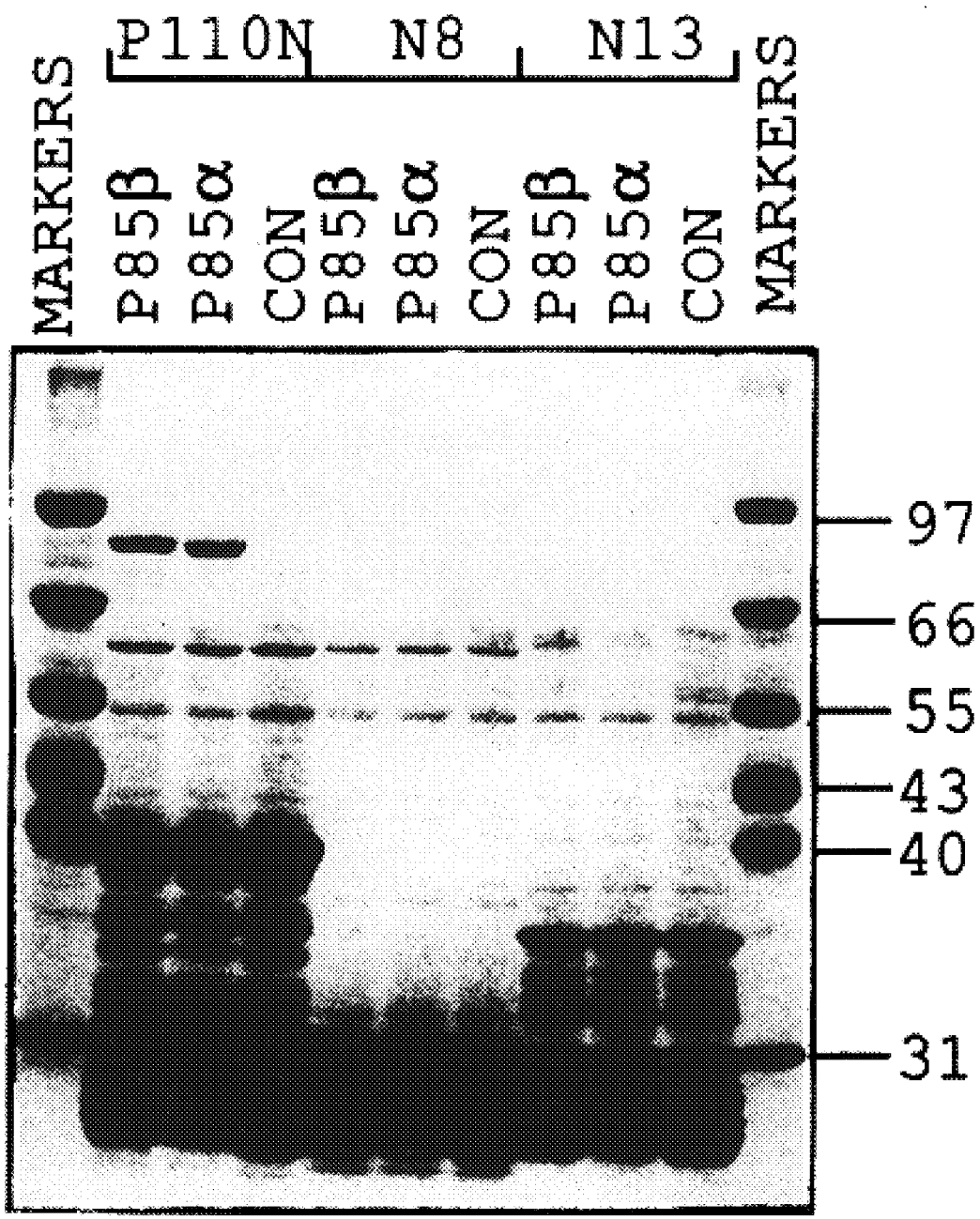

FIGS. 25A and 25B. The ability of the various deletion mutants and PCR fragments of p110-N to bind the p85 subunits.

EXAMPLE 1

PROTEIN PURIFICATION

A. Methods and Materials

Cells

A431 cells were maintained in Dulbecco's modified Eagle's medium containing 10% foetal calf serum. Maintenance of insect cell culture and infection of Spodoptera frugiperda (Sf9) cells were carried out as described in Summers and Smith (1987).

Preparation of A431 Membranes

This preparation was modified from that described by Thom et al (1977). Harvesting solution (0.05 M boric acid (pH 7.2), 0.15 M NaCl), extraction solution (0.02 M boric acid (pH 10.2), 0.2 mM EDTA) and borate solution 0.5 M Boric acid (pH 10.2) were all prepared fresh. Cells were washed once with ice-cold harvesting solution and then scraped into fresh harvesting solution. Cells were pelleted by low speed centrifugation at 200 g, and then resuspended by pipetting in 2 pellet volumes of harvesting solution. This was added slowly, with stirring, to 100 pellet volumes of extraction solution. After 10 min, 8 pellet volumes of borate solution was added and stirring continued for a further 5 min. This solution was filtered through nylon gauze (Av. mesh size 900 µm), and spun at 500 g for 10 min at 2° C. to pellet any nuclei/whole cells. Finally, the supernatant was centrifuged at 12,000 g in a ultracentrifuge SW28 rotor at 4° C. for 30 min. The membrane pellet was resuspended in a minimum volume of 50 mM Hepes (pH 7.5) and stored at −70° C.

Synthesis of Peptides

Peptides described in Table 2 below were synthesized on an Applied Biosystems 430A peptide synthesizer using FMOC chemistry and an appropriate amino acid addition program according to ABI's recommendations. Peptides were then purified by preparative reverse-phase HPLC. Composition of the peptides was checked by analytical HPLC, amino acid analysis and protein sequencing on an 477A automated pulse-liquid sequencer.

TABLE 2

| Peptide | Sequence |
|---------|----------|
| Y740 | G E S D G G Y M D M S K |
| Y751 | D M S K D E S V D Y V P M L D M K |
| Y751.S | C D E S V D Y V P M L |
| Y857 | A R D I M R D S N Y I S K G S T F |
| Y1313 | E F C P D P L Y E V M L K |
| Y527 | R R F T S T E P Q Y Q P G E N L |
| Y416[a] | R R L I E D N E Y T A R G |

[a]This peptide was purchased from Sigma Chemical Co Ltd rather than synthesized.

Phosphorylation of Peptides

Peptides were lyophilised to dryness to remove any contaminating chemicals remaining from synthesis/purification and then dissolved in HPLC grade water at a concentration of ~4 mg/ml.

For small scale phosphorylation: 20 µg of peptide, 10 µl 5×kinase buffer (250 mM Hepes (pH 7.4), 750 mM NaCl, 0.1% Triton X-100, 10 nM $MnCl_2$, 60 mM MgCl2, 50% glycerol, 500 mM sodium orthovanadate), 5 µl A431 membrane preparation and ATP/[γ-$^{32}$P]ATP (relative amounts depends on aim of phosphorylation). Water was added to adjust the volume to 50 µl.

For preparative phosphorylation, 2–3 mg of peptide was dissolved in 1.5 ml of water and added to 450 µl 5×kinase buffer. The pH was adjusted to 7.0. 250 µl of 0.1 M ATP and 500 µl of A431 plasma membranes (~2 mg/ml) was added and then the reaction was allowed to proceed for 18 h at room temperature with continual mixing.

Isolation of Phosphorylated Peptides by Reverse Phase HPLC

One milliliter of buffer A (Buffer A: 0.08% trifluoracetic acid, 1% acetonitrile in water; Buffer B: 0.08% trifluoracetic acid, 90% acetonitrile) was added to the kinase reaction and mixed. This solution was then spun for 20 min at 10,000 g to pellet the membranes. The supernatant containing the phosphopeptide was then loaded onto a Sep-Pak column ($C_{18}$) equilibrated with buffer A. The column was washed with 20 ml buffer A to elute ATP and then the peptide was eluted with 3×1 ml of 40% buffer B. The OD of the fractions was monitored at 268 nm and fractions containing peptide were pooled and then lyophilised to dryness (note that the phosphorylated Y751 peptide has essentially no absorption at 280 nm). The phosphopeptide was then separated from non-phosphorylated peptide using a 1090 HPLC system. For preparative separation a $C_{18}$ column (Aquapore OD-300, 250×7 mm) equilibrated with 100% buffer A (214 nm (sen. 50 mV)/280 nm (sen. 200 mV) was used with a 2 ml/min flow rate. The peptide was dissolved in 200 µl HPLC grate water and then loaded via a 500 µl loop. The column was then washed for 10 min with 100% buffer A before eluting the peptide and phosphopeptide with a 30 min linear gradient 0 to 45% buffer B followed by 5 min linear gradient to 100% buffer B. Peak fractions were collected manually. The pool fractions were diluted with water, lyophilised and then stored at −20° C.

Phosphoamino Acid Analysis of Phosphorylated Peptides

Peptides phosphorylated in the presence of [γ-$^{32}$P]ATP using either purified EGF receptor or A431 cell membranes were purified by $C_{18}$ Sep-Pak column and HPLC as described above. This material was then hydrolysed at 110° C. for 1 h in 1 ml of 6 M HCl. One millilitre of HPLC grade water was added and the sample was centrifuged at 10,000 g for 10 min to removed debris. The remaining supernatant was frozen and lyophilised to dryness. The pellet was resuspended in 2 ml of water, frozen and then lyophilised once more. This material was analysed by two dimensional thin-layer electrophoresis (essentially as described by Cooper et al, 1983).

Coupling of Peptides to Actigel Resin

Peptides were coupled to the matrix essentially as described by the manufacturers. Briefly, 500 µl (packed volume) of Actigel-ALD Superflow resin (Sterogene, Calif., USA) was washed five times with 100 mM phosphate buffer (pH 7.8) (coupling buffer). Phosphorylated or non-phosphorylated peptide (1 mg) was dissolved in 200 µl of coupling buffer and added to the resin. $NaCNBH_3$ (coupling solution) was added to a final concentration of 100 mM and this was then mixed at 4° C. for 6 h. The resin was washed with 10 column volumes of 500 mM NaCl and then incubated with 100 mM Tris-HCl (pH 8.0) for 1 h in the presence of coupling solution to block any unreacted sites on the resin. The resin was washed with 500 mM NaCl and finally with coupling buffer plus 500 µM vanadate and 0.02% $NaN_3$ and then stored at 4° C. Phosphopeptides bound to the Actigel matrix were stable for several months under these conditions.

Binding of Proteins to the Phosphopeptide Columns

Proteins were diluted in binding buffer (50 mM phosphate buffer (pH 7.2), 150 mM NaCl, 0.02% Triton X-100, 2 mM EDTA and 200 µM sodium orthovanadate), mixed with the appropriate peptide affinity resin and then allowed to bind for 2 h at 4° C. with rotation. The column material was washed repeatedly (>6×) with 50 column volumes of the same buffer and then with various elution buffers containing NaCl, urea or detergents. Bound proteins were either assayed for PI3-kinase activity or were removed from the column by boiling in SDS-PAGE sample buffer and then analysed by SDS-PAGE.

PI3-kinase Assay

PI3-kinase assays were carried out essentially as described in Whitman et al, (1987) in 50 μl containing 50 mM Tris-HCl (pH 7.5), 50 mM NaCl, 1 mM DTT, 0.5 mM EDTA, 5 mM MgCl$_2$, 100 μM ATP (plus 0.5 μCi [γ-$^{32}$P] ATP/assay), 1 mM PI plus soluble or column immobilised bovine brain PI3-kinase. Incubation was for 5 min at room temperature. The reaction was terminated by the addition of 100 μl of 0.1N HCl and 200 μl chloroform:methanol (1:1). The mixture was vortexed and then centrifuged to separate the phases. The upper phase was discarded and the lower organic phase washed with 80 μl of methanol: 1N HCl (1:1). After centrifugation the upper phase was again discarded and the lower phase evaporated to dryness. Reaction products were spotted on thin layer Silica gel 60 plates (pretreated with 1% oxalic acid, 1 mM EDTA in water-:methanol (6:4)) and developed in chloroform:methanol:4 N ammonia (9:7:4).

Preparation of C-terminal Specific Antisera for p85α and p85α

C-terminal peptide antisera were prepared against the bovine C-terminal sequences determined by cDNA cloning (Otsu et al, 1991). The peptides TLAYPVYAQQRR for p86α and TLAHPVRAPGPGPPAAR for p85α were synthesized by FMOC chemistry and purified by HPLC. The peptides were coupled using gluteraldehyde to KLH and then injected into the lymph nodes of rabbits using methods described in Kypta et al, (1988). Positive antisera as determined by enzyme-linked immunoassay were affinity purified on specific peptide-Actigel affinity columns.

B. Procedure and Results of Purification

Preparation of Y751 Phosphopeptide Column

A 17 amino acid peptide which contains Y751 of the human PDGF-β receptor was chosen for synthesis in an attempt to inlcude all necessary sequence determinants following a survey of the known binding sites for the PI3-kinase (see Table 2 above; reviewed in Cantley et al, 1991). In addition to the peptide context of Y751 of the PDGF β-receptor, the sequences around Y315 of polyoma middle T (Talmage et al, 1989) and Y721 of the human CSF-1 receptor (Shurtleff et al, 1990) were also considered. Using the phosphorylation protocol described above, greater than 50% phosphorylation of the Y751 peptide was achieved using either purified human EGF receptor or A431 membranes as a source of protein-tyrosine kinase. The phosphorylated Y751 peptide could be clearly identified during reverse phase HPLC analysis, where it eluted approximately one minute earlier than the nonphosphorylated peptide, since it produced a strong 214 nm absorbance, but little or no 280 nm signal (FIG. 1, panel A). Analysis of the absorption properties showed that phosphorylation of the Y751 peptide let to a shift in the absorption maximum from 280 to 267 nm (FIG. 1, panel B). For large scale phosphorylations A431 membranes were the preferred source of protein-tyrosine kinase activity since they could be more easily generated. However, as the Y751 peptide contains two serines, as well as a single tyrosine residue, it was thought important to demonstrate that peptide was phosphorylated exclusively at the tyrosine residue. This was established by two separate methodologies; analysis of HPLC purified phosphopeptide by phosphoamino acid analysis or by protein microsequencing. Phosphoamino acid analysis of the Y751 peptide, phosphorylated by either purified EGF receptor or A431 membranes, demonstrated that phosphorylation of the Y751 peptide was occuring exclusively at the tyrosine residue (FIG. 1, panel C). Sequence analysis of the phosphorylated and non-phosphorylated peptides also confirmed that both these peptides were 17 amino acids in length and that their sequences were identical except at cycle 10 where as expected no phenylthiohydantoin-Tyr derivative was observed for the phosphorylated peptide due to its modification.

Extended Purification of Bovine Brain PI3-kinase Using a Y751 Phosphopeptide Affinity Column A 650-fold purification of PI3-kinase from bovine brain has recently been described (Morgan et al, 1990), and this same method was used except that the gradient for the second Mono Q column was extended to give two distinct peaks containing PI3-kinase activity (FIG. 2, panel A). Both of these peaks (referred to hereafter as peak 1 (P1) and peak 2 (P2)) contained no PI kinase activity other than PI3-kinase activity as determined by HPLC analysis of deacylated product lipids (data not shown). However, both of these fractions still contained greater than 20 peptides detectable after SDS-PAGE gel analysis by silver staining (see FIG. 2, panel A). The precise subunit composition of the active PI3-kinase complex was still a point of some contention, so an attempt was made to address this question by affinity purifying the PI3-kinase activity from these two Mono Q pools. The bovine brain PI3-kinase preparation was diluted 10-fold in binding buffer and allowed to bind batchwise to the Y751 phosphopeptide affinity resin for 4 h at 4° C. After washing the column extensively with binding buffer, those proteins which remained bound were eluted with SDS-containing buffers and examined by SDS-PAGE. Two major polypeptide species of approximate molecular weights 85 and 110 kD, which bound specifically to the phosphopeptide column, but not to an identical column prepared with unphosphorylated Y751 peptide, were identified in both Mono Q peaks and were observed to be quantitatively depleted from the bovine brain PI3-kinase preparation (FIG. 2, panel B). Assaying the bound material, the presence of these two proteins appeared to be sufficient to generate full PI3-kinase activity (FIG. 3, lane 2). With fresh preparations of bovine brain PI3-kinase this column routinely removed >90% of the PI3-kinase activity present in Mono Q peaks 1 or peak 2 (c.f., FIG. 3, lanes 2 and 3) following a single incubation. Neither the 85 and 110 kD proteins, nor PI3-kinase activity bound to a column with an equivalent concentration of non-phosphorylated Y751 peptide (FIG. 3, lane 1) or to a column prepared with phosphotyramine, a phosphotyrosine analogue (data not shown). It should also be noted that binding of the PI3-kinase complex to the phosphopeptide column did not result in any apparent increase in the total enzyme activity present (FIG. 3, c.f., lanes 2 and 6). In fact a slight decrease in activity was often observed, but this was judged to be due to the unstable nature of the highly purified enzyme which was found to be inhibited by traces of metal ions and reversibly inhibited by oxidation. It is estimated that this affinity purification step results in a 7–8,000-fold purification of PI3-kinase from bovine brain relative to the DEAE load (the overall purification achieved from tissue is in fact much greater).

Elution of p85, p110 and PI3-kinase Activity from the Phosphopeptide Column

Elution of the above PI3-kinase complex from the phosphopeptide column proved to be difficult to achieve due to the high affinity of the interaction. Kazlauskas and Cooper (1990) have previously noted that the binding of cellular p85 proteins to phosphorylated PDGF-receptor was stable to treatment with solutions containing ionic detergents, 2 M NaCl, 1 M urea or 0.2% SDS. The p85 subunits and PI3-kinase complex were also found to bind tightly to the Y751 phosphopeptide matrix, and were likewise not eluted under any of the above conditions. At 20° C. the 85 and 110 kD proteins remained bound in the presence of either 2 M NaCl plus 0.5% Triton X-100, 5 M NaCl, 6 M Urea, 50 mM phosphotyrosine or up to 1 mg/ml free Y751 phosphopeptide. Several alternative elution protocols were investigated without success. An elution medium supplied with the Actigel resin was able to remove both proteins but led to a complete loss of activity. Interestingly no suitable conditions could be established whereby the 110 kD, but not the 85 kD, subunit was released from the column suggesting that the interaction between the 110 and 85 kD subunits is of high affinity. Elution of bound proteins was routinely carried out by heating the resin to 80° C. for 3 min in the present of 5 mM phosphate buffer (pH 7.0), 0.1% SDS, 0.1 mM DTT, 10% glycerol. The phosphopeptide column could be simply regenerated following elution by extensive washing in binding buffer (FIG. 3, lanes 4 and 5) and could be successfully used at least ten times before any deterioration in binding was observed.

Analysis of the p85 and 110 kD Proteins Bound to the Phosphopeptide Column

The relationship of the 85 kD proteins observed to bind to the Y751 phosphopeptide column to the recently cloned p85α and p85β proteins was investigated using the polyclonal antisera generated against the predicted C-terminal 12 and 18 amino acids of p85α and p85β, respectively. Despite the high degree of overall sequence similarity between p85α and p85β, the amino acid sequence over this segment is significantly different and thus p85α or p85β specific antisera were expected to be produced. Furthermore the amino acid sequence corresponding to this peptide in p85α is completely conserved between human, bovine and murine cDNAs suggesting that antibodies generated against this sequence might be useful for studying the expression of different p85 proteins in species other than bovine (Escobedo et al, 1991b; Otsu et al, 1991; Skolnik et al, 1991). The corresponding region of p85β in species other than bovine is currently unknown. The p85 antisera generated against these peptides could specifically immunoprecipitate the appropriate species of expressed recombinant p85 from either COS-1 or Sf9 cells but were not very efficient at immunoprecipitating PI3-kinase activity from either cell lines or from the partially purified bovine brain PI3-kinase preparation. However, these antisera were found to work well in Western blots. The data presented in FIG. 4 shows that these two antisera specifically recognized expressed p85 proteins present in either COS cells or in Sf9 cells. Longer exposures also revealed the endogenous COS p85 protein(s), but no such proteins were detected in Sf9 cells with these antisera. No cross reactivity was observed even at high concentrations of the recombinant proteins suggesting that they are specific for p85α (FIG. 4, panel A) and p85β (FIG. 4, panel B) respectively. The ability of these antisera to interact with the appropriate p85 species was demonstrated to be completely blocked in the presence of the appropriate peptide used to raise the antisera (FIG. 4, panel C). The p85 species in the two peaks of bovine brain PI3-kinase activity which bound to the Y751 phosphopeptide column was found to react exclusively with the anti C-terminal antisera raised against the p85α specific sequence (FIG. 4, panel A). Following immobilisation of the bovine brain PI3-kinase material on the Y751 phosphopeptide column, all the p85α immunoreactive material was bound to the column with none detectable by either silver staining or Western blot analysis in the supernatant (FIG. 4, panel D).

For sequence analysis of the PI3-kinase complex, the 110 and 85 kD subunits were eluted from the column, following extensive stringent washing, by briefly boiling the resin in 5 mM phosphate buffer (pH 7.0), 0.1% SDS, 0.1 mM DTT, 10% glycerol. Preparation of both 85 and 110 kD proteins for digestion with lysylendopeptidase and subsequent sequence analysis were performed in accordance with the protocol given hereinbefore. Amino acid sequence analysis of a lysylendopeptidase C digest of the p85 protein bound to the Y751 phosphopeptide column confirmed that the p85 protein present in both peak 1 and peak 2 from the mono Q column were identical to the previously cloned p85α (Otsu et al, 1991). No peptides corresponding to p85β were found in either peak. Extensive sequencing of the 110 kD protein affinity purified from both mono Q peak 1 and peak 2 material enabled the isolation of a novel cDNA (see below).

Specificity of Binding of the Purified Bovine Brain PI3-kinase

In order to evaluate the specificity of the Y751 phosphopeptide column for purifying the PI3-kinase, other phosphopeptide columns were prepared using peptides based on the amino acid sequences which surround known protein-tyrosine kinase phosphorylation sites. Tyrosine 857 is the other major autophosphorylation site in the human PDGF β-receptor and has been shown to be required for the binding of GAP, but not for association with the PI3-kinase (Kazlauskas & Cooper, 1989, 1990; Kazlauskas et al, 1991). For a direct comparison with the Y751 peptide a 17 amino acid peptide centred around tyrosine residue 857 was synthesized (see Table 2 above). A comparison the proteins from baculovirus expressing p85α Sf9 cell lysate or from bovine brain PI3-kinase fractions from mono Q peak 1 (P1) and peak 2 (P2) binding to either the Y751 (panel A) or Y587 (panel B) phosphopeptide columns is shown in FIG. 5. Whereas the baculovirus expressed p85α is observed to bind both columns to a similar extent, the 85 and 110 kD proteins from both peaks of activity are seen only to bind to the Y751 phosphopeptide column. Similarly, PI3-kinase activity is only found associated with the Y751 phosphopeptide column (FIG. 7, panel B).

To determine whether this binding specificity could be extended several other peptides were synthesized based on known tyrosine autophosphorylation sites (see Table 2 above). A shorter, 11 amino acid version of the Y751 peptide, termed Y751S, was also synthesized in an attempt to further refine the minimal SH2 recognition domain required. Two other peptides containing the YXXM motif were prepared, one based on the seqeunce around tyrosine 740 of the PDGF-β receptor, a second residue within the PDGF receptor kinase insert which may play a role in PI3-kinase binding (Escobedo et al, 1991a), and the second based around tyrosine Y1313 of Met, the hepatocyte growth factor receptor. To introduce a totally random sequence the synthetic peptide poly Glu:Ala:Tyr (6:3:1) was also phosphorylated and coupled to the Actigel matrix. Finally the peptides surrounding the two major phosphorylation sites from pp60$^{c-src}$, Y416 and Y527, were purchased and synthesized respectively. All peptides efficiently phosphorylated specifically on tyrosine residues using the EGF receptor and then were purified by HPLC as described above for the Y751 phosphopeptide.

Baculovirus expressed bovine p85α and p85β were chosen to test these columns (Otsu et al, 1991). Binding analysis was carried out under identical conditions to those previously established for the Y751 phosphopeptide column. Somewhat unexpectedly the baculovirus expressed p85 subunits bound to all phosphopeptide columns tested (see FIG. 7, panels A and B). They did not however bind to identical columns containing non-phosphorylated peptides (FIG. 6, panels A and B, lane 1 and data not shown). However when partially purified bovine brain PI3-kinase was applied to these columns it was found to bind exclusively to the phosphopeptide columns containing a YXXM motif (see FIG. 7 and FIG. 8, panel A).

That the Y751S phosphopeptide column appears to be as efficient at binding the active PI3-kinase complex as the longer Y751 phosphopeptide column suggests that the consensus sequence recently proposed by Cantley et al, (1991) does indeed contain all the sequence data necessary for correct recognition by the PI3-kinase SH2 domain (FIG. 8, panel B).

CLONING OF p110
C. Experimental Procedures
Materials

Restriction enzymes and DNA modification enzymes were obtained from standard commercial sources and used according to the manufacturer's recommendations. Oligonucleotides were synthesized on an Applied Biosystems 380B DNA synthesizer and used directly in subsequent procedures.
Cells The SGBAF-1 cell line was established by transfection of bovine adrenal cortex zona faciculata cells with pSV3neo as previosly described for other cell types (Whitley et al, 1987). SGBAF-1 cells and COS-1 cells were maintained in Dulbecco's modified eagle medium (DMEM) containing a 10% foetal calf serum (FCS). Maintenance of Spodoptera frugiperda (Sf9) cells was carried out as described by Summers and Smith, 1987.
Protein Purification and Amino Acid Sequence Determination The purification of the p85α and p110 proteins by chromatography on a peptide affinity column corresponding to amino acids 742–758 of the kinase insert region of the human PDGF-β receptor has been described above. The method used for the final purification of p110 for amino acid sequence analysis was in accordance with the Protocol given hereinbefore. This procedure was carried out on three separate PI3-kinase preparations. A fourth preparation was eluted from the matrix as before and boiled for 5 min. After cooling, the sample was diluted with 25 mM Tris-HCl, pH 8.8 and digested directly with lysylendopeptidase for 72 h at 30° C. Peptides were separated as above. Peptide sequences were determined using a modified Applied Biosystems 477A automated pulse-liquid sequencer.
mRNA Isolation and CDNA Cloning Total RNA was isolated fromthe SGBAF-1 by the method of Chirgwin et al. (1979) and poly(A)⁺mRNA selected by chromatography on oligo-dT cellulose (Maniatis et al., 1982). An oligo-dT primed cDNA library of 5×106 primary recombinants was constructed in lambda Uni-Zap (Stratagene) from 5 µg of this mRNA using the Stratagene Uni-Zap CDNA cloning system. The construction of the total bovine brain cDNA library in lambda Uni-Zap has been described previously (Otsu et al, 1991).
Library screening and Hybridizations The unamplified SGBAF-1 cDNA library ($10^6$ recombinants) was plated on *E. coli* K12 PLK-F' (Stratagene) at a density of $10^5$ plaques per 15 cm dish and lifts taken in duplicate onto nitrocellulose membranes (Millipore). For screening, filters were prehybridized for at least 1 h at 42° C. in 6×SSPE, 0.5% SDS, 10×Denhardt's solution, 100 µg ml$^{-1}$ denatured sonicated herring sperm DNA (Sigma). Hybridization was carried out in the same solution containing 10 ng ml$^{-1}$ radiolabelled oligonucleotide. Oligonucleotides used were: Peptide N (MDWIFHT) 5'-AA(G/A)ATGGA(T/C)TGGAT(C/T/A)TT(T/C)CA(T/C)AC-3'); Peptide J ( D D G Q L F H I D F G H F ) 5'-GATGATGGCCA(G/A)CTGTT(T/C)CA(T/C)AT(T/A)GA(T/C)TTTGGCCA (T/C)TT. Oligonucleotides were labelled with $^{32}$P at the 5' end in a 20 µl reaction containing 100 ng oligonucleotide, 1×kinase buffer (Promega), 0.1 mM spermidine, 5 mM dithiothreitol, 100 µCi [γ-$^{32}$P]ATP (5000 Ci mmol$^{-1}$, Amersham) and 2 µl (20 U) T4 polynucleotide kinase (Amersham). Filters were washed in 6×SSC, 0.1% SDS at room temperature and then subjected to autoradiography using Kodak XAR film. Hybridizing clones were plaque-purified and rescued as plasmids according to the manufacturers instructions.
Characterization of CDNA Clones Sequencing was carried out by the chain termination method using the Sequenase system (United States Biochemicals). Clones for sequencing were obtained by directed cloning of restriction fragments into M13 mp18 and mp19 vectors (Yanisch-Perron et al., 1985) and by making a series of exonuclease III mediated deletions (Henikoff, 1984; Pharmacia Exonuclease III deletion kit). DNA sequences were analysed on a MicroVAX computer using the Wisconsin (UWGCG: Devereux et al., 1984) sequence analysis package.
RACE PCR RACE PCR was carried out essentially as published previously (Frohman et al., 1988; Harvey and Garlison, 1991). Briefly, first strand cDNA primed with random hexamers (Amersham) was synthesized from 1 µg of SGBAF-1 cell mRNA using the Stratagene first strand cDNA synthesis kit. First strand cDNA was isolated by isopropanol precipitation and tailed with oligo-dA using terminal deoxynucleotidyl transferase (BRL). PCR was performed using oligo 2224 (5'-AATTCACACACTGGCATGCCGAT) and adaptor-dT (5'-GACTCGAGTCGACATCGATTTTTTTTTTTTTTTTT) as primers using a Perkin Elmer/Cetus Tap polymerase PCR kit (conditions: 94° C. 1 min, 35° C. 1 min, 72° C. 2 min, 30 cycles). Products were fractionated on a 1.5% low melting point agarose gel and visualized by staining with ethidium bromide. The gel was sliced into 6 bands (size range 150–2000 bp) and DNA isolated from each gel slice. A further round of PCR was performed on this DNA using oligonucleotide 2280 (5'-TTTAAGCTTAGGCATTCTAAAGTCACTATCATCCC) and adaptor (5'-GACTCGAGTCGACATCGA) as primers (conditions: 94° C. 1 min, 56° C. 1 min, 72° C. 2 min, 35 cycles). Products were fractionated on an agarose gel and visualised by staining with ethidium bromide. A band 250 bp shorter than the size of the DNA in the gel slice used for the PCR was expected. An intensely staining band of 350 bp obtained from the −600 bp gel slice was excised, digested with Hindlll and Sall and ligated into Bluescript KS-digested with Hindlll and Xhol to give plasmid pBS/race. Two independent inserts were completely sequenced.
Southern Transfer Hybridizations High molecular weight DNAs were isolated from cell lines by standard techniques (Maniatis et al, 1982). DNAs were digested with restriction endonucleases, fractionated through 0.5% agarose gels and transferred to nitrocellulose (BA85, Schleicher and Schuell) as described in Maniatis et al (1982). Prehybridization was carried out in 1 M NaCl, 10×Denhardt's, solution, 50 mM Tris-HCl (pH 7.4), 10 mM EDTA, 0.1% SDS and 100 µg ml$^{-1}$ denatured sonicated herring sperm DNA at 65° C. Hybridization was carried out overnight in the same solution containing 20 ng ml$^{-1}$ radio-labelled probe fragment (0.88 kb XbaI-PstI fragment: Probe a, FIG. 9, lower panel) of specific activity >10$^8$ dpm µg$^{-1}$). Probe fragments were isolated from agarose gels be electroelution (Maniatis et al, 1982) and labelled by nick translation (Rigby et al, 1977) using [α-$^{32}$] dATP(>3000 Ci mmol-1, Amersham). Membranes were washed extensively in 0.1×SSC, 0.1% SDS at 68° C. or at 50° C. in 0.5×SSC, 0.1% SDS to detect related sequences, and subjected to autoradiography with Kodak XAR film.

Northern Transfer Hybridizations

Poly(A)$^+$RNA from total bovine brain or the SGBAF-1 cell line was modified with DMSO and glyoxal and fractionated on a 0.9% agarose gel run in 10 mM phosphate buffer (pH 7.5) (Maniatis et al, 1982). Nucleic acid was transferred to nylon membranes (Hybond-N, Amersham) and filters baked dry. Prehybridization was carried out at 60° C. in 50% formamide, 5×SSPE, 5×Denhardt's solution, 0.2% SDS, 200 µg ml$^{-1}$ denatured sonicated herring sperm DNA and 200 µg ml$^{-1}$ yeast RNA. Hybridization was carried out in the same solution containing 1×10$^7$ cpm ml$^{-1}$ antisense RNA probe. Probe was prepared by in vitro transcription of a 2 kb fragment (nucleotides 598–2608; Probe b, FIG. 9, lower panel) subcloned in pSPT19 (Boehringer), using SP6 RNA polymerase (Amersham) and [α$^{32}$-P] UTP (Amersham) according to the manufacturers conditions. Membranes were washed in 0.1×SSC, 0.1% SDS at 60° C. Filters were treated with 1 µg ml$^{-1}$ RNAase A (Sigma) in 2×SSC for 15 min at room temperature and the filter rinsed at 50° C. in 0.1×SSC. Filters were then subjected to autoradiography against Kodak XAR film at −70° C.

PCR Determination of p85α and p110 mRNA

For p85α 125 ng of poly (A)$^+$RNA was reverse transcribed with 2.5 units rTth DNA polymerase (Perkin-Elmer-Cetus) at 70° C. for 10 min in a 10 µl reaction containing 10 mM Tris-HCl (pH 8.3), 90 mM KCl, 1 mM MnCl, 0.5 mM dNPT mixture and 1.2 AM antisense primer (5'-CAGGCCTGGCTTCCTGT). For DNA polymerization the reaction volume was adjusted to 50 µl by adding a single mix giving the following final concentrations: 5% (v/v) glycerol, 10 mM Tris-HCl (pH 8.3), 100 mM KCl, 0.75 mM EGTA, 0.05% (v)v) Tween 20, 2 mM MgCl$_2$, 0.24 AM sense primer (5'-AACCAGGCTCAACTGTT). PCR was then performed under the following reaction conditions: 92° C. 1 min, 58° C. 1 min, 72° C. 1 min for 25 cycles on a Perkin Elmer-Cetus DNA thermal cycler.

Conditions for p110 were similar except concentration of the antisense primer (5'-TGCTGTAAATTCTAATGCTG) was increased to 4.8 µM during the reverse transcription step. DNA polymerisation conditions were the same except the final MgCl$_2$ concentration was increased to 2.5 mM and both primers (sense primer=5'-GTATTTCATGAAACAAATGA) were present at a final concentration of 0.96 µM. Taq DNA polymerase (Promega) was also added at 0.03 U µl$^{-1}$. PCR was performed as follows: 92° C. 30 sec, 54° C. 5 sec, 72° C. 30 sec for 35 cycles. 20 µl of each reaction was run on a 3% agarose gel (Maniatis et al, 1982) and visualised by staining with ethidium bromide.

Antibodies and Immunoprecipitations

For the preparation of the anti C-terminal p110 antiserum, peptide CKMDWIFHTIKQHALN was synthesized by FMOC chemistry and purified by HPLC. It was then coupled to KLH using glutaraldehyde, and injected into the lymph nodes of rabbits using methods described in Rypta, R M et al. (1990), Cell 62, 481–492. Positive antisera as determined by enzyme-linked immunoassay were affinity purified on specific peptide-Actigel affinity columns. Anti-p85a (Otsu et al, 1991) and anti CSF-1 receptor (Ashmun et al., 1989) antisera are previously documented. Immunoprecipitations were carried out as described in Otsu et al., 1991.

PI3-kinase Assay

The assay for PI3-kinase activity was carried out as described by Whitman et al. (1985).

Expression of p110 in Sf9 Cells

To clone the p110 coding region into the baculovirus transfer vector p36C (Page, 1989) a sau 3Al site (GGATCA) present 10 nucleotides upstream from the initiation codon (see FIG. 9) was changed to a BamHl (GGATCC site by PCR mediated mutagenesis. Briefly, a sense oligonucleotide substituting C for A at position 6 of the Sau3Al site was used in a PCR reaction with an antisense primer comprising nucleotides (102–124) of the p110 sequence (see FIG. 9) using Vent polymerase (New England Biolabs). Template DNA was random-primed first strand cDNA prepared from SGBAF-1 cell mRNA as described above; PCR conditions: 94° C. 1 min, 50° C. 1 min, 72° C. 2 min, 35 cycles. The PCR product was digested with BamHl-EcoNl and a 118 bp fragment isolated from a low melting point agarose geL. This BamHl-EcoNl fragment was cloned into p110/2.2 digested with BamHl (present in vector sequences) and EcoNl (nucleotide=108) giving plasmid p110/(BamHl). The BamHl-EcoNl fragment of p110/(BamHl) was sequenced and found to agree with that previously determined. A 3.4 kb BamHl-Kpnl (Kpnl site present in the vector) fragment was isolated from p110/(BamHl) and ligated into p36C baculovirus transfer vector (Page, 1989) previously digested with the same enzymes. Recombinant viruses were obtained as described in Summers and Smith (1987). Sf9 cells were infected at a multiplicity of infection of 10 with recombinant viruses in IPL-41 media supplemented with 10% FCS. Cells were harvested and lysed 2 days post-infection in EB lysis buffer (20 mM Tris-HCl (pH 7.4), 50 mM NaCl, 50 mM NaF, 1% NP40, 1 mM EDTA, 500 µM sodium orthovanadate, 2 mM PMSF, 100 Kallikrein inhibitor units of Aprotinin ml$^{-1}$) (Kazlauskas and Cooper, 1989) and lysates were analysed by immunoappreciation.

Association of p110 and p85α with CSF-1 Receptor

This assay was performed essentially as described by Kazlauskas and Cooper (1990). Sf9 cells were infected as already described and lysed 48 h post-infection in EB lysis buffer. CSF-1 receptor was immunoprecipitated from Sf9 cells and collected on Protein A-Sepharose beads. The immunocomplex was then subjected to extensive washing (3 times with EB lysis buffer, twice with kinase buffer; 50 mM HEPES (pH 7.4), 150 mM NaCl, 0.02% Triton X-100, 12 mM MgCl$_2$, 2 mM MnCl$_2$, 10% glycerol, 500 µM sodium orthovanadate) and the receptor phosphorylated for 15 min at 20° C. with ATP. The precipitates were then washed again to remove free ATP and incubated for 2 h at 4° C. with cell lysates prepared from Sf9 cells infected with viruses expressing (i) p85α, (ii) p110 or (iii) co-infected with viruses expressing p85α and p110. The immune complexes were washed and assayed for associated PI3-kinase activity.

Expression of p85α and p110 in COS-1 Cells

For transient expression of p85α in COS-1 cells the coding region for p85α was cloned into the adenovirus late promoter based expression vector pMT2 (Kaufman et al, 1989) as previously described (Otsu et al, 1991). For expression of the p110 CDNA plasmid pSG5–p110 was constructed as follows. The 3.4 kb BamHl-Hindlll fragment from cDNA p2.1 was ligated into pSG5 (Stratagene) cut with BamHl and Bglll, the Hindlll and Bglll overhangs of p2.1 and pSG5 respectively, being filled in with Klenow polymerase. This gave construct pSG5.2.

Plasmid pBS/race (above) was digested with EcoRl and Hindlll, the 350 bp band gel purified by electroelution (Maniatis et al, 1982) and further digested with Sau3Al and Bsml. This mixture was then added to the gel purified Bsml-BstMl fragment from p2.1 and ligated in a three fragment ligation to pSG5.2 digested with BamHl and BstXl. 5 µg of each DNA was transfected into 10 cm dishes of 80% confluent COS-1 cells using Lipofectin (BRL) under conditions suggested by the manufacturers. Lysates were analysed by immunoprecipitation with anti-p85α polyclonal antiserum or with anti-p110 C-terminal peptide antiserum. Immunocomplexes collected on Protein A-Sepharose beads were analysed either on 10% SDS-PAGE gels followed by autoradiography or subjected to in vitro PI3-kinase assays as described.

D. Results of Cloning cDNA Cloning and Deduced Amino Acid sequence of p110

Initially, an oligo(dT) primed bovine brain cDNA library (Otsu et al, 1991) was screened with oligonucleotide probes made against peptides J and N (see FIG. 9). No hybridizing clones were detected. Therefore, a new cDNA library of 5×10hu 6primary recombinants was constructed from mRNA isolated from a pSV3 neo transfected bovine adrenal cortex zona fasciculate cell line (SGBAF-1), which was known to contain PI3-kinase activity (Otsu et al, 1991). Screening of 1×10$^6$ primary recombinants from this library with the same oligonucleotides led to the detection of 66 clones positive with both probes. Twenty overlapping clones were characterized and found to possess inserts from 1–4 kb. The clone with the longest insert representing coding sequence (clone p110/2.1) was completely sequenced. This revealed a potential open reading frame (ORF) of 1053 amino acids with a predicted molecular weight of 123 kD. The ORF contained all the sequenced peptides, but was not preceded by in-frame stop codons. Since the predicted size of the p110 protein from SDS gels is 110 kD, it was possible that the protein could initiate from an internal methionine within this ORF.

Expression studies carried out in COS-1 cells using methionines 16, 30, 123 and 130 as potential start codons (initiation at Met 123 would give rise to a protein of 110 kD) did not lead to the syntheses of a protein corresponding to p110 or any augmentation of PI3-kinase activity in these cells. This suggested p110/2.1 is missing 5' coding sequence and that either p110 protein runs anomalously on SDS-PAGE gels or that it is synthesized as part of a larger precursor molecule. Characterization of the remaining 46 positive clones initially isolated, showed that all had inserts shorter than that in clone p110/2.1. To further extend the p110/2.1 cDNA in the 5' direction a RACE (rapid amplification of cDNA ends) polymerase chain reaction (PCR) (Frohman et al, 1988; Harvey and Garlison, 1991) was used. Two independent products which extended the known nucleotide sequence were characterized (see FIG. 9, lower panel). The nucleotide and deduced amino acid sequences for the coding region of the composite cDNA are presented in FIG. 9. The putative initiation codon is preceded by an in-frame stop codon and occurs in a Kozak consensus sequence (Kozak, 1987) for the initiation of translation (data not shown). The deduced amino acid sequence encodes a protein of 1068 amino acids with a calculated relative molecular mass of 124,247.

Analysis of the p110 Nucleotide and Deduced Amino Acid Sequences

The coding region of the cDNA for p110 is extremely A+T rich (G+C content=39.3%) which is reflected in the failure to use codons TCG (Serine) and GTC (Valine). When the p110 amino acid sequence was compared with sequences in the Swissprot and NBRF protein databases, significant homology was found to only one protein, Vps34p (FIG. 10). This is a rare 100 kD protein from Saccharomyces cerevisiae involved in the sorting of proteins into the yeast vacuole and in the vacuole morphogenesis during budding (Herman and Emr, 1990). A search of the p110 sequence for amino acids conserved in the active sites of kinases, reveals $G_{842}$, $K_{863}$, $D_{916}$, $N_{921}$, and the DFC; triplet at residues 933–935 (these residues are marked in FIG. 2B) which might be homologous to $G_{52}$, $K_{72}$, $D_{166}$, $N_{171}$ and the DFG triplet at residues 184–186 in cAMP-dependent protein kinase (Knighton et al, 1991a,b). Equivalent residues are present in Vps34p and are also marked in FIG. X. The glycine rich P-loop (Saraste et al., 1990), found in many kinases (Hanks et al., 1988), does not appear to be present in either p110 or Vps34p.

Genomic Southern Blot Analysis of p110 Genes

Given the occurrence of at least two forms of p85 (Otsu et al, 1991), Southern blot analysis was used to analyse the number of p110 related genes which occur in genomic DNA isolated from bovine, human and rat sources. The analysis clearly provides evidence for a second, closely related, gene in rat and human genomic DNA (e.g. compare FIG. 11A lanes 4 and 9 with FIG. 11B lanes 4 and 9). For bovine DNA there appear to be no hybridization signals removed by washing at higher stringency (compare FIG. 11A lanes 1, 2 and 3 with FIG. 11B lanes 1, 2 and 3). However, it is possible that a related gene exists in bovine DNA, but, either it does not cross-hybridize under the conditions used, or it is too similar in sequence to be detected by differential washing.

Expression of p110 Cells and Tissues

A northern blot analysis carried out on mRNA isolated from the SGBAF-1 cell line and total bovine brain is shown in FIG. 12A. Both mRNA samples contain major p110 specific transcripts of 4.8 kb and 9 kb, although there is substantially more p110 message present in mRNA isolated from SGBAF-1 cells (FIG. 12A, lane 2) than that isolated from total bovine brain (FIG. 12A, lane 1). A PCR based study was performed to examine the distribution and conservation of p110 mRNA in cell lines and tissue from several species. Amplification of a p110 specific fragment is seen for three human mRNAs (218 bp; FIG. 12B lanes 1, 2 and 3) and two bovine mRNAs (212 bp; FIG. 12B, lanes 5 and 6). Similar sized fragments are amplified from cell lines of simian and porcine origin (FIG. 12B, lanes 4 and 7, respectively), indicating the existence of a p110 homologue in these species. An additional band of 300 bp is amplified from bovine brain mRNA (FIG. 12B, lane 5) and its identity is currently being investigated. Since PI3-kinase activity may reside in a p85α/p110 complex (Carpenter et al, 1990; Otsu et al., 1991; Shibasaki et al., 1991), some of these cell lines were examined to see whether messages for p85α and p110 are co-expressed. Amplification of a p85α specific 190 bp fragment is seen for the three human omission (FIG. 12C, lanes 1, 2 and 3) cell lines and one simian (FIG. 12C, lane 4) cell line analysed. Thus, at least in these four cell lines, messages for p85α and p110 are co-expressed.

p110 cDNA Encodes a Protein of Apparent Molecular Weight 110 kD which Possesses PI3-kinase Activity To demonstrate that the p110 cDNA encodes the 110 kD subunit of PI3-kinase, it was expressed in the baculovirus expression system (Summers and Smith, 1987). Immunoprecipitation with an anti-p110 antiserum from Spodoptera frugiperda (Sf9) cells infected with the p36C-p110 virus revealed a novel protein of apparent molecular weight 110 kD (FIG. 13A, lane 4) which co-migrated with the p110 PI3-kinase subunit purified from bovine brain. No such protein was seen in anti-p110 immunoprecipitates prepared from cells infected with a control wild-type virus (FIG. 13A, lane 2). This baculovirus expressed p110 was used to examine whether p110, alone, possesses catalytic activity or whether a p85α/p110 complex is required. When assayed, p110-containing immunoprecipitates were found to possess significant levels of PI3-kinase activity (FIG. 13B, lane 4), the identity of the lipid product being confirmed as PI(3)P by HPLC analysis. No activity was detected in anti-p110 immunoprecipitates prepared from control infected cells (FIG. 13B, lane 2). These results clearly demonstrate that the p110 subunit of PI3-kinase is sufficient for catalytic activity.

p110 Expressed in Insect Cells Forms a Stable Complex with p85α

Since PI3-kinase purified from bovine brain is a complex of p85α and p110, the ability of p85α and p110 expressed in insect cells to reconstitute an active p85α/p110 complex was examined. Baculoviruses expressing either p85α (pAcC4–p85α; Otsu et al, 1991) or p110 (p36C–p110) were infected separately, or together, into Sf9 cells and expressed proteins analysed as described in experimental procedures. Immunoprecipitates of p85α alone (FIG. 13A, lane 3) were inactive in a PI3-kinase assay (FIG. 13B, lane 3) as previously demonstrated (Otsu et al, 1991). In double infection experiments, both p85α and p110 were detected in either anti-p85α (FIG. 13A, lane 5) or anti-p110 (FIG. 13A, lane 6) immunoprecipitates. As neither subunit-specific antiserum recognises the other subunit (see FIG. 15A, lane 3; FIG. 15C, lane 2), the simplest interpretation of this data is that, when expressed in Sf9 cells, p110 and p85α (FIG. 13B, lane 5) or the anti-p110 antisera (FIG. 13B, lane 6) were both active. Neither antiserum immunoprecipitated endogenous PI3-kinase activity from Sf9 cells infected with wild-type virus (FIG. 13B, lanes 1 and 2).

PI3-kinase Activity Expressed in Sf9 Cells Can Associate with the Activated CSF-1 Receptor PI3-kinase activity has been shown to associate with many activated PTK receptors, but particularly well studied have been those receptor PTKs possessing a kinase insert region, e.g., PDGF-β receptor (Coughlin, S R et al., (1989), Science 243, 1191–1193 and the CSF-1 receptor (Varticovski et al, 1989; Shurtleff et al, 1990). An in vitro association assay (Kazlauskas and Cooper, 1990) was used to study the association of PI3-kinase activity expressed in insect cells with the activated CSF-1 receptor. FIG. 14 shows that baculovirus expressed PI3-kinase activity can associate with the CSF-1 receptor, but only from an Sf9 cell lysate containing both p85α and p110 (FIG. 14, lane 2), and only when the receptor has been phosphorylated prior to incubation with Sf9 cell lysate (compare FIG. 14, lanes 2 (+ATP) and 3 (−ATP)). No PI3-kinase activity associates with CSF-1 receptors incubated with Sf9 cells lysates containing p85α alone (FIG. 14, lane 4) or p110 alone (FIG. 14, lane 5). No activity is found associated with the CSF-1 receptor immunoprecipitated from Sf9 cells (FIG. 14, lane 1). Thus, PI3-kinase subunits expressed in insect cells can be used to reconstitute an active p85α/p110 complex that binds to a phosphorylated PTK receptor.

Expression of PI3-kinase in COS-1 Cells

The results shown above were all obtained from expression studies carried out in insect cells. In order to study p110 and its interaction with p85α in a mammalian cell system, transient co-expression studies in COS-1 cells were performed. The p110 CDNA was cloned into the SV40 based expression vector, pSG5 (giving plasmid pSF5–p110) and transfected into COS-1 cells, either alone or together with a p85α expression construct, pMT2–p85α (Otsu et al., 1991). To enable proteins to be more easily visualised transfected COS-1 cells were metabolically labelled with $^{35}$S-methionine for 3–4 h prior to lysis. Radiolabelling at this time results in preferential labelling of proteins synthesized from transfected constructs. Cell lysates were immunoprecipitated with either anti-p85α (FIG. 15, panels A and B) or anti-p110 antisera (FIG. 15, panels C and D). Immunoprecipitated proteins were either visualised by autoradiography following fractionation on SDS-PAGE gels (FIG. 15, panels A and C) or subjected to an in vitro PI3-kinase assay (FIG. 15, panels B and D).

Figure 15A:
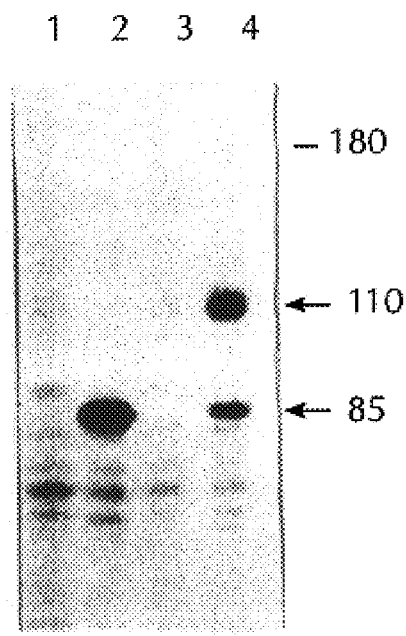
Figure 15B:
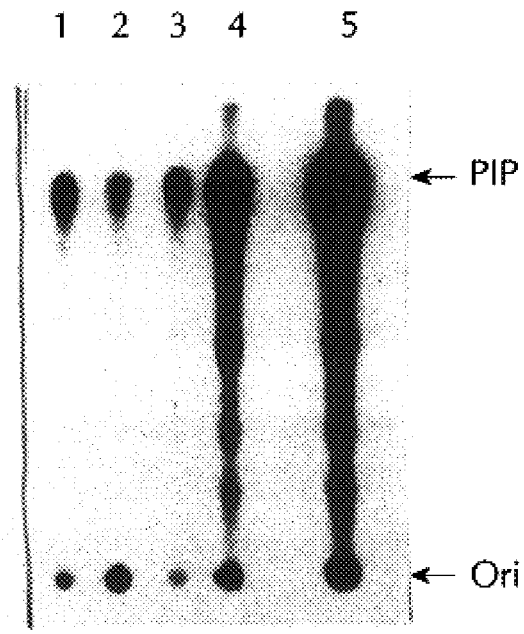
Figure 15C:
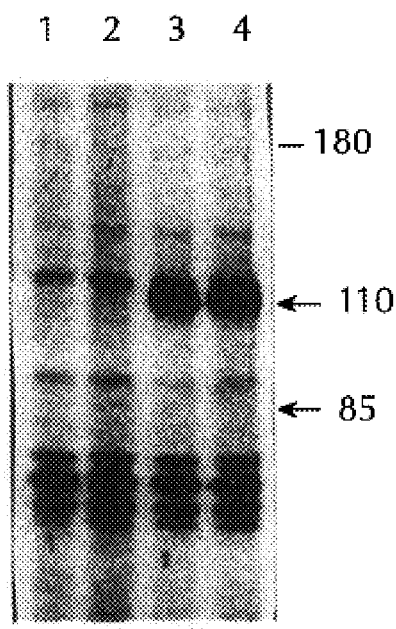

Transfection of pMT2–p85α resulted in a significant elevation of p85α over the background level due to endogenous simian p85α–compare FIG. 15A, lanes 2 and 4 with FIG. 15A, Lane 1. In p85α/p110 co-transfectants, the anti-p85α antiserum co-immunoprecipitates p85α and p110 (FIG. 15A, lane 4), demonstrating the existence of a p85α/p110 complex. When assays for PI3-kinase activity were performed on the anti-p85α immunoprecipitates, enhanced activity (10 fold over the background due to endogenous simian PI3-kinase) was only detected with immunoprecipitates which contained both p85α and p110 (compare FIG. 15B, lane 4 with FIG. 15B lanes 1, 2 and 3). These results demonstrate that in COS-1 cells, as in Sf9 cells, the p110 cDNA directs the synthesis of a protein of molecular weight 110 kD, which associates with p85α to give a p85α/p110 complex that possesses PI3-kinase activity.

Figure 15D:
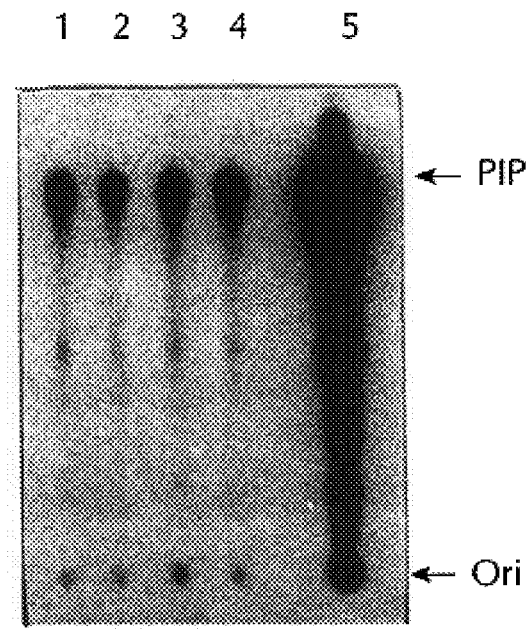

However, when proteins were immunoprecipitated from the same lysates with the anti-p110 antiserum and PI3-kinase assays performed, the results were surprising. As expected. the anti-p110 antiserum immunoprecipitated p110 from cells transfected with pSG5–p110 (FIG. 15C, lane 3). However, in addition, it would only immunoprecipitate free p110 from lysates prepared from cells co-transfected with p85α and p110 (FIG. 15C, lane 4) even though p85α/p110 complex was present in these lysates (FIG. 15A, lane 4). When assayed for PI3-kinase activity, no activity above that present in control immunoprecipitates (FIG. 15D, lanes 1 and 2), was present in p110 containing immunoprecipitates prepared from either p110-transfected (FIG. 15D, lane 3) or, p85α and p110 co-transfected, cells (FIG. 15D, lane 4). Thus, the anti-p110 antiserum is capable of immunoprecipitating p110 from cell lysates of both infected Sf9 cells (FIG. 13A, lane 4) and transfected COS-1 cells (FIG. 15C, lane 3), but only the immunoprecipitates prepared from Sf9 cell lysates possess elevated levels of PI3-kinase activity (compare FIG. 13B, lane 4 and FIG. 15D, lane 3). Also, the anti-p110 antiserum immunoprecipitates the p85α/p110 complex when expressed in Sf9 cells, but not when expressed in COS-1 cells.

As indicated above, analysis of the cloned p110 cDNA shows it to encode a protein of 1068 amino acids with a calculated molecular weight of 124 kD. The reason for the difference in size between the calculated (124 kD) and observed molecular weight value 110 kD is unclear, but it is known that many proteins migrate anomalously on SDS-PAGE gels. Expression of the protein encoded by this ORF in Sf9 cells, COS-1 cells, reticulocyte lysate and *E. coli* all result in the production of a protein of apparent molecular weight 110 kD.

The deduced amino acid sequence of p110 contains all the peptide sequences determined by protein sequence analysis.

Since the peptides were obtained from a lysylendopeptidase digestion, it is expected that they should all be preceded by an arginine residue. This is true in every case, except for peptide A which is preceded by an arginine residue (Arg 162). Nucleotide sequence data obtained from another cDNA clone covering this region confirms the presence of an arginine residue in this position. Thus, it seems likely that cleavage at this site by lysylendopeptidase results from a sequence polymorphism.

When a database search was performed on the p110 sequence no significant homology was detected with any proteins known to be involved in inositol lipid metabolism. However, as noted, p110 did show significant homology throughout its C-terminal half to the Saccharomyces cerevisiae protein Vps34p. The possibility that Vps34p is a yeast PI-kinase is currently being investigated. If p110 and Vps34p are homologous proteins then it is interesting to speculate that p110 might also be involved with protein targeting and/or vesicular transport. PI3-kinase activity has previously been implicated in vesicle mediated responses in higher eukaryotes. Hence, PI3-kinase activity is seen to increase following stimulation of platelets with thrombin (Kucera and Rittenhouse, 1990) and neutrophils with f-Met-Leu-Phe (Traynor-Kaplan et al, 1988). In both cases, ligand stimulation promotes the fusion of vesicular structures necessary for the biological response. A role for PI3-kinase in intracellular vesicles following the activation of PTKs has also been suggested (Cantley et al, 1991; Kelly et al, 1992).

Southern blotting data suggests there may be two genes for PI3-kinase in rats and humans. Evidence for the existence of a second gene in rat DNA is also provided by the results of Carpenter et al., (1990), who identified two forms of p110 in their purified PI3-kinase preparation. In situ hybridization confirms the presence of two closely related sequences in human DNA, although one could be a pseudogene. Two forms of p85 (p85α and p85β) have been characterized (Otsu et al, 1991), although only p85α is found associated with p110 in PI3-kinase from bovine brain. It is possible to speculate that p85β associates with a second form of p110.

Although, at present, the function of the 3-phosphorylated phosphoinositides produced by PI3-kinase is unclear, the availability of expression systems which allow their generation will aid in the determination of their function.

EXAMPLE 2

Using the bovine cDNA probe constituted by the XbaI-PstI fragment of the sequence of FIG. 9 (probe a, bottom panel) and genomic DNAs from several species, Southern blot analyses prove positive against the bovine probe in the following species:- bovine (calf thymus), human (HeLa cells), rat (liver), simian (COS cells), porcine (ZNR cells), chicken (from Promega), and Xenopus (liver).

The human cDNA was isolated from a cDNA library, made from mRNA isolated from the human cell line KGla using standard techniques. The probe was a partial cDNA from the second half of the bovine p110 cDNA. The probe was labelled with $^{32}p$ and hybridised overnight to the library filters at 65° C. in 1M NaPi, 7% SDS buffer. The filters were washed in 2×SSC at −50° C., and exposed to X-ray film at −70° C. The nucleotide sequence is shown in FIG. 16 together with the corresponding amino acid sequence. The human p110 sequence has 95% homology to the bovine p110 sequence at the DNA level and is 98% identical at the protein level (FIGS. 17 and 18). The protein sequence is shown in FIG. 19. Primers (357) AAG GAT CAG AAC AAT GCC T and (416) AGG CTT TCT TTA GCC ATC A were used to amplify, using RT-PCR (94° C. 30 sec 50° C. 30 sec, 72° C. 60 secs; for 35 cycles) the partial sequence of a highly related p110 gene (p110–11). P110–11 has 96% nucleotide homology to p110 (sequence not provided).

Two novel cDNAs related to p110 have been cloned. Degenerate primers were designed to conserved sequences between human p110 and the related yeast gene VPS34 (Sense (GDDLRQD) 5' GGN GAT/C GAT/C T/C TA/G CGN CAA/G GA-3' antisense (FHIDFGHF) 5'A/GAA A/GTG ICC A/GAA A/GTC A/G/TAT A/GTG A/GAA-3). These were used in RT-PCR reactions using mRNA from the human cell lines MOLT4 and U937 (940° C. 30 sec, 50° C. 30 sec, 72° C. 30 sec for 35 cycles). Two novel cDNA's, PITR-c and PITR-f, related to p110, were isolte. The PITR-c nucleotide sequence is shown in FIG. 20. This gene is highly related to the yeast gene VPS34, the VPS34 protein is involved in the protein sorting from the golgi to the vacuole and has an intrinsic PI3-kinase activity. The PITR-f nucleotide sequence is shown in FIG. 21 and is more similar to p110 than PITR-c and is likely also to possess PI3-kinase activity. The alignment of human p110, the human PI3-kinase related genes PITR-c and PITR-f and the yeast PI3-kinase VPS34 are shown in FIG. 22. The amino acids conserved in 3 or more of the proteins are shown in the upper case.

The interation of the p85 and p110 subunits of PI3-kinase are thought to be required for the activity of the kinase in mammalian cells. Thus inhibiting the interaction between the subunits could provide a means of inhibiting the activity of this signal transduction pathway. In order to design reagents to p110 which will block the interaction, it is useful to define the region of p110 which binds to the p85 subunits. To do this a series of mutants were constructed which express various domains of the p110 protein (FIG. 23B). These fragments were expressed as GST fusion proteins in bacteria. The proteins were then bound to a glutathione sepharose column (Pharmicia) according to the manufacturer's instructions (Panayotou G et al (1992) EmboJ 11:4261–4272). The ability of these protein fragments to bind the p85 subunits was assessed by the ability of the column specifically to retain p85 subunits purified from baculovirus (Otsu et al(1991) Cell 65:91–104). As shown in FIG. 23A, only p110-N (aα1–128) was capable of binding the p85α and β subunits. To further characterise the binding domain, deletion mutants and PCR fragments were made from the p110-N fragment as shown in FIG. 24. The results in FIG. 25 demonstrate that a domain containing amino acids 19–110 of human p110 is sufficient to associate with the p85 subunits. Removal of a further 20 amino acids from either the amino or carboxy termini led to loss of binding activity. Now that this domain has been identified it allows the design of specific peptides, antibodies or small molecules which can inhibit the interaction between the subunits.

The invention includes a human PI3-kinase p110 subunit sequence comprising amino acids 19 to 110 of human p110, or an amino terminal truncated or carboxy terminal truncated derivative thereof having less than 20 amino acids deleted from the amino terminal or carboxy terminal end, respectively, and also included is a method of inhibiting p85 and p110 mammalian PI3-kinase subunit interaction, which comprises utilizing a molecule which blocks the binding domain located between amino acids 19 and 110 of human p110.

The invention further provides the use of a sequence or derivative as defined above in screening for a therapeutic or prophylactic agent which operates by inhibiting interaction between p85 and p110 mammalian PI3-kinase subunits.

References

Anderson, D et al., (1990), Science 250, 979–982.
Ashmum, R A et al., (1989), Blood 73, 827–837.
Auger, K R et al., (1989), J. Biol. Chem. 264, 20181–20184.
Auger, K R et al., (1991), Cancer Cells 3, 263–270.
Berridge, M J et al., (1989), Nature 341, 197–205.
Bjorge, J D et al., (1990), Proc. Natl. Acad. Sci. USA 87,, 3816–3820.
Cantley, L C et al., (1991), Cell 64, 281–302.
Carpenter, C L et al., (1990), Biochemistry 29, 11147–11156.
Carpenter, C L et al., (1990), J. Biol. Chem. 265, 19704–19711.
Chan, T 0 et al., (1990), Mol. Cell. Biol. 10, 3280–3283.
Chirgwin, J M et al., (1979), Biochemistry 18, 294–299.
Cohen, B et al., (1990), Mol. Cell. Biol. 10, 2909–2915.
Cooper, J A et al., (1983), Methods Enzymol. 99, 387–402.
Coughlin, S R et al., (1989), Science 243, 1191–1194.
Courtneidge, S A et al., (1987), Cell 50, 1031–1037.
Devereux, J et al., (1984), Nucleic Acids Res. 12, 387–395.
Downes, C P et al., (1990), Eur. J. Biochem. 193, 1–18.
Downes, C P et al., (1991), Cellular Signalling 3, 501–513.
Enderman, G et al., (1987), Biochemistry 26, 6845–6852.
Escobedo, J A et al., (1988), Nature 335, 85–87.
Escobedo, J A et al., (1991a), Mol. Cell. Biol. 11, 1125–1132.
Escobedo, J A et al., (1991b), Cell 65, 75–82.
Frohman, M A et al., (1988), Proc. Nat. Acad. Sci. USA 85, 8998–9002.
Fukui, Y et al., (1989), Mol. Cell. Biol. 9, 1651–1658.
Graziani, A et al., (1991), J. Biol. Chem. 266, 22087–22090.
Hanks, S K et al., (1988), Science 241, 42–52.
Hanks, S K (1991), Current Opinion in Structural Biology 1, 369–383.
Harvey, R J et al., (1991), Nuc. Acids. Res. 19, 4002.
Henikoff, S (1984), Gene 28, 351–359.
Herman, P K et al., (1990), Mol. Cell. Biol. 10, 6742–6754.
Hu, P et al., (1992), Mol. Cell. Biol. 12, 981–990.
Kaplan, D R et al., (1986), Proc. Natl. Acad. Sci. USA 83, 3624–3628.
Kaplan, D R et al., (1987), Cell 50, 1021–1029.
Kaplan, D R et al., (1990), Cell 61, 125–133.
Kaufman, R J et al., (1989), Mol. Cell. Biol. 9, 946–958.
Kawasaki, H et al., (1990), Anal. Biochem. 186, 264–268.
Kazlauskas, A et al., (1989), Cell 58, 1121–1133.
Kazlauskas, A et al., (1990), EMBO J. 9, 3279–3286.
Kazlauskas, A et al., (1990), Science 247, 1578–1581.
Kazlauskas, A et al., (1991), Cell Regulation 2, 413–425.
Kelly, K L et al., (1992), J. Biol. Chem. 267, 3423–3428.
Kemp, B E et al., (1990), TIBS 15, 342–346.
Knighton, D R et al., (1991a), Science 253, 407–414.
Knighton, D R et al., (1991b), Science 253, 414–420.
Koch, C A et al., (1991), Science 252, 668–674.
Kozak, M (1987), Nucl. Acids Res. 15, 8125–8148.
Kucera, G L et al., (1990), J. Biol. Chem. 265, 5345–5348.
Kypta, R M et al., (1988), EMBO J. 7, 3837–3844.
Kypta, R M et al., (1990), Cell 62, 481–492.
Lev, S et al., (1991), EMBO J. 10, 647–654.
Lips, D L (1989), J. Biol. Chem. 264, 8759–8763.
Majerus, P W et al., (1990), Cell 63, 459–465.
Maniatis, T et al., (1982) Molecular Cloning: a laboratory manual (Cold Spring Harbor Laboratory).
Margolis, B et al., (1990), EMBO J. 9, 4375–4380.
Matsuda, M et al., (1991), Mol. Cell. Biol. 11, 1607–1613.
Mayer, B J et al., (1990), Proc. Natl. Acad. Sci. USA 87, 2638–2642.
Mayer, B J et al., (1991), Proc. Natl. Acad. Sci. USA 88, 627–631.
Meisenhelder, J et al., (1989), Cell 57, 1109–1122.
McGlade, C J et al., (1992), Mol. Cell. Biol. 12, 991–997.
Moran, M F et al., (1990), Proc. Natl. Acad. Sci. USA 87, 8622–8626.
Morgan, S J et al., (1990), Eur. J. Biochem. 191, 761–767.
Morrison, D K et al., (1989), Cell 58, 649–657.
Otsu, M et al., (1991), Cell 65, 91–104.
Page, M J (1989), Nucl. Acids Res. 17, 454.
Pendergast, A M et al., (1991), Cell 66, 161–171.
Rhee, S G (1991), Trends Biochem. Sci. 16, 297–301.
Rigby, P W J et al.,(1977), I. J. Mol. Biol. 113, 237–251.
Robinson, J S et al., (1988), Mol. Cell. Biol. 8, 4936–4948.
Ruderman, N B et al., (1990), Proc. Natl. Acad. Sci. USA 87 1411–1415.
Saraste, M et al., (1990), Trends Biochem. Sci. 15, 430–434.
Serunian, L A et al., (1989), J. Biol. Chem. 264, 17809–17815.
Shurtleff, S A et al., (1990), EMBO J. 9, 2415–2421.
Shibasaki, F et al., (1991), J. Biol. Chem. 266, 8108–8114.
Skolnik, E Y et al., (1991), Cell 65, 83–90.
Shurtleff, S A et al., (1990), EMBO J. 9, 2415–2421.
Stephens, L R et al., (1991), Nature 351, 33–39.
Summers, M D et al., (1987), A Manual of Methods for Baculovirus Insect Vectors and Insect Cell Culture Procedures; Texas Agri. Exp. Station Bull. No 1555.
Talmage, D A et al., (1989), Cell 59, 55–65.
Thom D, et al., (1977), Biochem. J. 168, 187–194.
Traynor-Kaplan, A E et al., (1988), Nature 334, 353–356
Ullrich, A et al., (1990), Cell 61, 203–212.
Ulug, E T et al., (1990), J. Virol. 64, 3895–3904.
Varticovski, L et al., (1989), Nature 342, 699–702.
Varticovski, L et al., (1991), Mol. Cell. Biol. 11, 1107–1113.
Whitley, G S J et al., (1987), Mol. Cell. Endocrinol. 52, 279–284.
Whitman, M et al., (1985), Nature 315, 239–242.
Whitman, M et al., (1987), Biochem. J. 247, 165–174.
Whitman, M et al., (1988), Biochem. Biophys. Acta. 948, 327–344.

Whitman, M et al., (1988), Nature 332, 644–646.
Woodgett, J R (1989), Anal. Biochem. 180, 237–241.

Yanisch-Perron, C et al., (1985), Gene 33, 103–119.
Yu, J C et al., (1991), Mol. Cell. Biol. 11, 3780–3785.

Claims

1. A method for making an antibody which specifically binds to a polypeptide which has PI3 kinase activity and a molecular weight of about 110 kilodaltons as determined by SDS-PAGE, comprising administering an immunogen to a subject animal, wherein said immunogen comprises a peptide, the amino acid sequence of which consists of the amino acid sequence set forth at SEQ ID NO: 32, in an amount sufficient to provoke an antibody response against said immunogen by said subject animal, and isolating said antibody from said subject animal.

2. The method of claim 1, wherein said immunogen comprises keyhole limpet hemocyanin complexed to said peptide.

3. An isolated antibody which specifically binds to the PI3 kinase having the amino acid sequence set forth in SEQ ID.

NO: 32, wherein said antibody binds to said PI3 kinase at an epitope positioned in the region defined by amino acids 1–128 of SEQ ID. NO: 32.

4. The antibody of claim 3, wherein said epitope is positioned in the region defined by amino acids 19–110 of SEQ. ID. NO: 32.

5. The antibody of claim 3, wherein said epitope is positioned in the region defined by amino acids 19–108 of SEQ. ID. NO: 32.

6. The antibody of claim 3, wherein said epitope is positioned in the region defined by amino acids 1–108 of SEQ ID. NO: 32.

7. An antibody which binds to a polypeptide which has PI3 kinase activity and a molecular weight of about 110 kilodaltons as determined by SDS-PAGE, produced by immunizing a subject animal with an immunogen, said immunogen comprising a peptide, the amino acid sequence of which consists of the amino acid sequence set forth at SEQ ID NO: 32.

8. The antibody of claim 7, wherein said immunogen comprises keyhold limpet hemocyanin complexed to said peptide.

9. The antibody of claim 7, wherein said antibody is a monoclonal antibody.

10. A method for determining if a polypeptide which has PI3 kinase activity and a molecular weight of about 110 kilodaltons as determined by SDS-PAGE is present in a sample, comprising contacting said sample with the antibody of claim 7 and determining binding of said antibody as a determination of said polypeptide in said sample.

* * * * *

UNITED STATES PATENT AND TRADEMARK OFFICE
CERTIFICATE OF CORRECTION

PATENT NO. : 6,274,327 B1
DATED : August 14, 2001
INVENTOR(S) : Hiles et al.

It is certified that error appears in the above-identified patent and that said Letters Patent is hereby corrected as shown below:

Column 15,
Lines 25 and 29, change "p85α" to -- p85β --.

Column 16,
Line 65, change "phopeptide" to -- phosphopeptide --.

Column 19,
Line 57, change "5α 106" to -- $5 \times 10^6$ --.

Column 21,
Line 45, change "AM" to -- µM --.

Column 22,
Line 2, change "Rypta" to -- Kypta --.

Column 24,
Line 14, change "DFC" to -- DFG --.

Column 27,
Line 60, change "-50 ° C" to -- 50° C --.

Column 28,
Line 13, change "isolte" to -- isolated --.

Signed and Sealed this

Twenty-sixth Day of March, 2002

Attest:

JAMES E. ROGAN
*Attesting Officer*   *Director of the United States Patent and Trademark Office*

```
                              SEQUENCE LISTING (1) GENERAL INFORMATION:

(iii) NUMBER OF SEQUENCES: 50

(2) INFORMATION FOR SEQ ID NO: 1:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 1:

Gly Glu Ser Asp Gly Gly Tyr Met Asp Met Ser Lys
1               5                   10

(2) INFORMATION FOR SEQ ID NO: 2:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO: 2:

Asp Met Ser Lys Asp Glu Ser Val Asp Tyr Val Pro Met Leu Asp Met
1               5                   10                  15

Lys (2) INFORMATION FOR SEQ ID NO: 3:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO: 3:

Cys Asp Glu Ser Val Asp Tyr Val Pro Met Leu
1               5                   10

(2) INFORMATION FOR SEQ ID NO: 4:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO: 4:

Ala Arg Asp Ile Met Arg Asp Ser Asn Tyr Ile Ser Lys Gly Ser Thr
1               5                   10                  15

Phe (2) INFORMATION FOR SEQ ID NO: 5:

(i) SEQUENCE CHARACTERISTICS:
        (A) LENGTH: 13 amino acids
        (B) TYPE: amino acid
        (C) STRANDEDNESS: single
        (D) TOPOLOGY: linear
```

(xi) SEQUENCE DESCRIPTION: SEQ ID NO: 5:

Glu Phe Cys Pro Asp Pro Leu Tyr Glu Val Met Leu Lys
1               5                  10

(2) INFORMATION FOR SEQ ID NO: 6:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO: 6:

Arg Arg Phe Thr Ser Thr Glu Pro Gln Tyr Gln Pro Gly Glu Asn Leu
1               5                  10                  15

(2) INFORMATION FOR SEQ ID NO: 7:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 7:

Arg Arg Leu Ile Glu Asp Asn Glu Tyr Thr Ala Arg Gly
1               5                  10

(2) INFORMATION FOR SEQ ID NO: 8:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 8:

Thr Leu Ala Tyr Pro Val Tyr Ala Gln Gln Arg Arg
1               5                  10

(2) INFORMATION FOR SEQ ID NO: 9:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO: 9:

Thr Leu Ala His Pro Val Arg Ala Pro Gly Pro Gly Pro Pro Ala Ala
1               5                  10                  15
Arg (2) INFORMATION FOR SEQ ID NO: 10:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 10:

Tyr Xaa Xaa Met
1

(2) INFORMATION FOR SEQ ID NO: 11:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 11:

```
Met Asp Trp Ile Phe His Thr
1               5
```

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 12:

```
AARATGGAYT GGATHTTYCA YAC                                              23
```

(2) INFORMATION FOR SEQ ID NO: 13:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 13:

```
Asp Asp Gly Gln Leu Phe His Ile Asp Phe Gly His Phe
1               5                   10
```

(2) INFORMATION FOR SEQ ID NO: 14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 14:

```
GATGATGGCC ARCTGTTYCA YATWGAYTTT GGCCA                                 35
```

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 15:

```
AATTCACACA CTGGCATGCC GAT                                              23
```

(2) INFORMATION FOR SEQ ID NO: 16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 16:

```
GACTCGAGTC GACATCGATT TTTTTTTTTT TTTTT                                 35
```

(2) INFORMATION FOR SEQ ID NO: 17:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 17:

TTTAAGCTTA GGCATTCTAA AGTCACTATC ATCCC                      35

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 18:

GACTCGAGTC GACATCGA                                            18

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 19:

CAGGCCTGGC TTCCTGT                                             17

(2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 20:

AACCAGGCTC AACTGTT                                             17

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 21:

TGCTGTAAAT TCTAATGCTG                                      20

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 22:

GTATTTCATG AAACAAATGA                                      20

(2) INFORMATION FOR SEQ ID NO: 23:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO: 23:

```
Cys Lys Met Asp Trp Ile Phe His Thr Ile Lys Gln His Ala Leu Asn
1               5                   10                  15
```

(2) INFORMATION FOR SEQ ID NO: 24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 24:

AAGGATCAGA ACAATGCCT                                                19

(2) INFORMATION FOR SEQ ID NO: 25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 25:

AGGCTTTCTT TAGCCATCA                                                19

(2) INFORMATION FOR SEQ ID NO: 26:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 26:

```
Gly Asp Asp Leu Arg Gln Asp
1               5
```

(2) INFORMATION FOR SEQ ID NO: 27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 27:

GGNGAYGAYY TRCGNCARGA                                            20

(2) INFORMATION FOR SEQ ID NO: 28:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 28:

```
Phe His Ile Asp Phe Gly His Phe
1               5
```

(2) INFORMATION FOR SEQ ID NO: 29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 29:

```
RAARTGCCRA ARTCDATRTG RAA                                              23
```

(2) INFORMATION FOR SEQ ID NO: 30:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO: 30:

```
Glu Glu Glu Glu Glu Tyr Met Pro Met Xaa Xaa
1               5                   10
```

(2) INFORMATION FOR SEQ ID NO: 31:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 31:

```
Asp Asp Asp Asp Asp Val
1               5
```

(2) INFORMATION FOR SEQ ID NO: 32:

(i) SEQUENCE CHARACTERISTICS:
        (A) LENGTH: 3412 base pairs
        (B) TYPE: nucleic acid
        (C) STRANDEDNESS: single or double
        (D) TOPOLOGY: linear (ix) FEATURE:
        (A) NAME/KEY: CDS
        (B) LOCATION: 1..3204
        (D) OTHER INFORMATION: /standard_name= "CDS"

(xi) SEQUENCE DESCRIPTION: SEQ ID NO: 32:

```
ATG CCT CCA AGA CCA TCA TCA GGT GAA CTG TGG GGC ATC CAC TTG ATG         48
Met Pro Pro Arg Pro Ser Ser Gly Glu Leu Trp Gly Ile His Leu Met
1               5                   10                  15

CCC CCA AGA ATC CTA GTG GAA TGT TTA CTA CCA AAT GGA ATG ATA GTG         96
Pro Pro Arg Ile Leu Val Glu Cys Leu Leu Pro Asn Gly Met Ile Val
                20                  25                  30

ACT TTA GAA TGC CTC CGT GAG GCT ACA TTA GTA ACT ATA AAG CAT GAA        144
Thr Leu Glu Cys Leu Arg Glu Ala Thr Leu Val Thr Ile Lys His Glu
            35                  40                  45

CTA TTT AAA GAA GCA AGA AAA TAC CCT CTC CAT CAA CTT CTT CAA GAT        192
Leu Phe Lys Glu Ala Arg Lys Tyr Pro Leu His Gln Leu Leu Gln Asp
        50                  55                  60

GAA TCT TCT TAC ATT TTC GTA AGT GTT ACC CAA GAA GCA GAA AGG GAA        240
Glu Ser Ser Tyr Ile Phe Val Ser Val Thr Gln Glu Ala Glu Arg Glu
65                  70                  75                  80

GAA TTT TTT GAT GAA ACA AGA CGA CTT TGT GAT CTT CGG CTT TTT CAA        288
```

-continued

```
              Glu Phe Phe Asp Glu Thr Arg Arg Leu Cys Asp Leu Arg Leu Phe Gln
                              85                  90                  95

CCA TTT TTA AAA GTA ATT GAA CCA GTA GGC AAC CGT GAA GAA AAG ATC           336
Pro Phe Leu Lys Val Ile Glu Pro Val Gly Asn Arg Glu Glu Lys Ile
            100                 105                 110

CTC AAT CGA GAA ATT GGT TTT GCT ATC GGC ATG CCA GTG TGC GAA TTT           384
Leu Asn Arg Glu Ile Gly Phe Ala Ile Gly Met Pro Val Cys Glu Phe
            115                 120                 125

GAT ATG GTT AAA GAT CCT GAA GTA CAG GAC TTC AGA AGA AAT ATT CTT           432
Asp Met Val Lys Asp Pro Glu Val Gln Asp Phe Arg Arg Asn Ile Leu
        130                 135                 140

AAT GTT TGT AAA GAA GCT GTG GAT CTT AGG GAT CTT AAT TCA CCT CAT           480
Asn Val Cys Lys Glu Ala Val Asp Leu Arg Asp Leu Asn Ser Pro His
145                 150                 155                 160

AGT AGA GCA ATG TAT GTC TAT CCG CCA CAT GTA GAA TCT TCA CCA GAG           528
Ser Arg Ala Met Tyr Val Tyr Pro Pro His Val Glu Ser Ser Pro Glu
                165                 170                 175

CTG CCA AAG CAC ATA TAT AAT AAA TTG GAT AGA GGC CAA ATA ATA GTG           576
Leu Pro Lys His Ile Tyr Asn Lys Leu Asp Arg Gly Gln Ile Ile Val
            180                 185                 190

GTG ATT TGG GTA ATA GTT TCT CCA AAT AAT GAC AAG CAG AAG TAT ACT           624
Val Ile Trp Val Ile Val Ser Pro Asn Asn Asp Lys Gln Lys Tyr Thr
            195                 200                 205

CTG AAA ATC AAC CAT GAC TGT GTG CCA GAA CAA GTA ATT GCT GAA GCA           672
Leu Lys Ile Asn His Asp Cys Val Pro Glu Gln Val Ile Ala Glu Ala
        210                 215                 220

ATC AGG AAA AAA ACT AGA AGT ATG TTG CTA TCA TCT GAA CAA TTA AAA           720
Ile Arg Lys Lys Thr Arg Ser Met Leu Leu Ser Ser Glu Gln Leu Lys
225                 230                 235                 240

CTC TGT GTT TTA GAA TAT CAG GGC AAG TAC ATT TTA AAA GTG TGT GGA           768
Leu Cys Val Leu Glu Tyr Gln Gly Lys Tyr Ile Leu Lys Val Cys Gly
                245                 250                 255

TGT GAT GAA TAC TTC CTA GAA AAA TAT CCT CTG AGT CAG TAT AAG TAT           816
Cys Asp Glu Tyr Phe Leu Glu Lys Tyr Pro Leu Ser Gln Tyr Lys Tyr
            260                 265                 270

ATA AGA AGC TGT ATA ATG CTT GGG AGG ATG CCC AAT TTG AAG ATG ATG           864
Ile Arg Ser Cys Ile Met Leu Gly Arg Met Pro Asn Leu Lys Met Met
            275                 280                 285

GCT AAA GAA AGC CTT TAT TCT CAA CTG CCA ATG GAC TGT TTT ACA ATG           912
Ala Lys Glu Ser Leu Tyr Ser Gln Leu Pro Met Asp Cys Phe Thr Met
        290                 295                 300

CCA TCT TAT TCC AGA CGC ATT TCC ACA GCT ACA CCA TAT ATG AAT GGA           960
Pro Ser Tyr Ser Arg Arg Ile Ser Thr Ala Thr Pro Tyr Met Asn Gly
305                 310                 315                 320

GAA ACA TCT ACA AAA TCC CTT TGG GTT ATA AAT AGA GCA CTC AGA ATA          1008
Glu Thr Ser Thr Lys Ser Leu Trp Val Ile Asn Arg Ala Leu Arg Ile
                325                 330                 335

AAA ATT CTT TGT GCA ACC TAC GTG AAT CTA AAT ATT CGA GAC ATT GAC          1056
Lys Ile Leu Cys Ala Thr Tyr Val Asn Leu Asn Ile Arg Asp Ile Asp
            340                 345                 350

AAG ATT TAT GTT CGA ACA GGT ATC TAC CAT GGA GGA GAA CCC TTA TGT          1104
Lys Ile Tyr Val Arg Thr Gly Ile Tyr His Gly Gly Glu Pro Leu Cys
            355                 360                 365

GAC AAT GTG AAC ACT CAA AGA GTA CCT TGT TCC AAT CCC AGG TGG AAT          1152
Asp Asn Val Asn Thr Gln Arg Val Pro Cys Ser Asn Pro Arg Trp Asn
        370                 375                 380

GAA TGG CTG AAT TAT GAT ATA TAC ATT CCT GAT CTT CCT CGT GCT GCT          1200
Glu Trp Leu Asn Tyr Asp Ile Tyr Ile Pro Asp Leu Pro Arg Ala Ala
385                 390                 395                 400
```

```
CGA CTT TGC CTT TCC ATT TGC TCT GTT AAA GGC CGA AAG GGT GCT AAA        1248
Arg Leu Cys Leu Ser Ile Cys Ser Val Lys Gly Arg Lys Gly Ala Lys
                405                 410                 415

GAG GAA CAC TGT CCA TTG GCA TGG GGA AAT ATA AAC TTG TTT GAT TAC        1296
Glu Glu His Cys Pro Leu Ala Trp Gly Asn Ile Asn Leu Phe Asp Tyr
                420                 425                 430

ACA GAC ACT CTA GTA TCT GGA AAA ATG GCT TTG AAT CTT TGG CCA GTA        1344
Thr Asp Thr Leu Val Ser Gly Lys Met Ala Leu Asn Leu Trp Pro Val
                435                 440                 445

CCT CAT GGA TTA GAA GAT TTG CTG AAC CCT ATT GGT GTT ACT GGA TCA        1392
Pro His Gly Leu Glu Asp Leu Leu Asn Pro Ile Gly Val Thr Gly Ser
        450                 455                 460

AAT CCA AAT AAA GAA ACT CCA TGC TTA GAG TTG GAG TTT GAC TGG TTC        1440
Asn Pro Asn Lys Glu Thr Pro Cys Leu Glu Leu Glu Phe Asp Trp Phe
465                 470                 475                 480

AGC AGT GTG GTA AAG TTC CCA GAT ATG TCA GTG ATT GAA GAG CAT GCC        1488
Ser Ser Val Val Lys Phe Pro Asp Met Ser Val Ile Glu Glu His Ala
                    485                 490                 495

AAT TGG TCT GTA TCC CGA GAA GCA GGA TTT AGC TAT TCC CAC GCA GGA        1536
Asn Trp Ser Val Ser Arg Glu Ala Gly Phe Ser Tyr Ser His Ala Gly
                500                 505                 510

CTG AGT AAC AGA CTA GCT AGA GAC AAT GAA TTA AGG GAA AAT GAC AAA        1584
Leu Ser Asn Arg Leu Ala Arg Asp Asn Glu Leu Arg Glu Asn Asp Lys
            515                 520                 525

GAA CAG CTC AAA GCA ATT TCT ACA CGA GAT CCT CTC TCT GAA ATC ACT        1632
Glu Gln Leu Lys Ala Ile Ser Thr Arg Asp Pro Leu Ser Glu Ile Thr
530                 535                 540

GAG CAG GAG AAA GAT TTT CTA TGG AGT CAC AGA CAC TAT TGT GTA ACT        1680
Glu Gln Glu Lys Asp Phe Leu Trp Ser His Arg His Tyr Cys Val Thr
545                 550                 555                 560

ATC CCC GAA ATT CTA CCC AAA TTG CTT CTG TCT GTT AAA TGG AAT TCT        1728
Ile Pro Glu Ile Leu Pro Lys Leu Leu Leu Ser Val Lys Trp Asn Ser
                565                 570                 575

AGA GAT GAA GTA GCC CAG ATG TAT TGC TTG GTA AAA GAT TGG CCT CCA        1776
Arg Asp Glu Val Ala Gln Met Tyr Cys Leu Val Lys Asp Trp Pro Pro
                580                 585                 590

ATC AAA CCT GAA CAG GCT ATG GAA CTT CTG GAC TGT AAT TAC CCA GAT        1824
Ile Lys Pro Glu Gln Ala Met Glu Leu Leu Asp Cys Asn Tyr Pro Asp
            595                 600                 605

CCT ATG GTT CGA GGT TTT GCT GTT CGG TGC TTG GAA AAA TAT TTA ACA        1872
Pro Met Val Arg Gly Phe Ala Val Arg Cys Leu Glu Lys Tyr Leu Thr
610                 615                 620

GAT GAC AAA CTT TCT CAG TAT TTA ATT CAG CTA GTA CAG GTC CTA AAA        1920
Asp Asp Lys Leu Ser Gln Tyr Leu Ile Gln Leu Val Gln Val Leu Lys
625                 630                 635                 640

TAT GAA CAA TAT TTG GAT AAC TTG CTT GTG AGA TTT TTA CTG AAG AAA        1968
Tyr Glu Gln Tyr Leu Asp Asn Leu Leu Val Arg Phe Leu Leu Lys Lys
                645                 650                 655

GCA TTG ACT AAT CAA AGG ATT GGG CAC TTT TTC TTT TGG CAT TTA AAA        2016
Ala Leu Thr Asn Gln Arg Ile Gly His Phe Phe Phe Trp His Leu Lys
                660                 665                 670

TCT GAG ATG CAC AAT AAA ACA GTT AGC CAG AGG TTT GGC CTG CTT TTG        2064
Ser Glu Met His Asn Lys Thr Val Ser Gln Arg Phe Gly Leu Leu Leu
            675                 680                 685

GAG TCC TAT TGT CGT GCA TGT GGG ATG TAT TTG AAG CAC CTG AAT AGG        2112
Glu Ser Tyr Cys Arg Ala Cys Gly Met Tyr Leu Lys His Leu Asn Arg
690                 695                 700

CAA GTC GAG GCA ATG GAA AAG CTC ATT AAC TTA ACT GAC ATT CTC AAA        2160
Gln Val Glu Ala Met Glu Lys Leu Ile Asn Leu Thr Asp Ile Leu Lys
705                 710                 715                 720
```

```
CAG GAG AGG AAG GAT GAA ACA CAA AAG GTA CAG ATG AAG TTT TTA GTT      2208
Gln Glu Arg Lys Asp Glu Thr Gln Lys Val Gln Met Lys Phe Leu Val
                725                 730                 735

GAG CAA ATG AGG CGA CCA GAT TTC ATG GAT GCC CTA CAG GGC TTG CTG      2256
Glu Gln Met Arg Arg Pro Asp Phe Met Asp Ala Leu Gln Gly Leu Leu
            740                 745                 750

TCT CCT CTA AAC CCT GCT CAT CAA CTA GGA AAC CTC AGG CTT AAA GAG      2304
Ser Pro Leu Asn Pro Ala His Gln Leu Gly Asn Leu Arg Leu Lys Glu
                755                 760                 765

TGT CGA ATT ATG TCT TCT GCA AAA AGG CCA CTG TGG TTG AAT TGG GAG      2352
Cys Arg Ile Met Ser Ser Ala Lys Arg Pro Leu Trp Leu Asn Trp Glu
            770                 775                 780

AAC CCA GAC ATC ATG TCA GAG TTA CTG TTT CAG AAC AAT GAG ATC ATC      2400
Asn Pro Asp Ile Met Ser Glu Leu Leu Phe Gln Asn Asn Glu Ile Ile
785                 790                 795                 800

TTT AAA AAT GGG GAT GAT TTA CGG CAA GAT ATG CTA ACA CTT CAA ATT      2448
Phe Lys Asn Gly Asp Asp Leu Arg Gln Asp Met Leu Thr Leu Gln Ile
                805                 810                 815

ATT CGT ATT ATG GAA AAT ATC TGG CAA AAT CAA GGT CTT GAT CTT CGA      2496
Ile Arg Ile Met Glu Asn Ile Trp Gln Asn Gln Gly Leu Asp Leu Arg
            820                 825                 830

ATG TTA CCT TAT GGT TGT CTG TCA ATC GGT GAC TGT GTG GGA CTT ATT      2544
Met Leu Pro Tyr Gly Cys Leu Ser Ile Gly Asp Cys Val Gly Leu Ile
                835                 840                 845

GAG GTG GTG CGA AAT TCT CAC ACT ATT ATG CAA ATT CAG TGC AAA GGC      2592
Glu Val Val Arg Asn Ser His Thr Ile Met Gln Ile Gln Cys Lys Gly
            850                 855                 860

GGC TTG AAA GGT GCA CTG CAG TTC AAC AGC CAC ACA CTA CAT CAG TGG      2640
Gly Leu Lys Gly Ala Leu Gln Phe Asn Ser His Thr Leu His Gln Trp
865                 870                 875                 880

CTC AAA GAC AAG AAC AAA GGA GAA ATA TAT GAT GCA GCC ATT GAC CTG      2688
Leu Lys Asp Lys Asn Lys Gly Glu Ile Tyr Asp Ala Ala Ile Asp Leu
                885                 890                 895

TTT ACA CGT TCA TGT GCT GGA TAC TGT GTA GCT ACC TTC ATT TTG GGA      2736
Phe Thr Arg Ser Cys Ala Gly Tyr Cys Val Ala Thr Phe Ile Leu Gly
            900                 905                 910

ATT GGA GAT CGT CAC AAT AGT AAC ATC ATG GTG AAA GAC GAT GGA CAA      2784
Ile Gly Asp Arg His Asn Ser Asn Ile Met Val Lys Asp Asp Gly Gln
                915                 920                 925

CTG TTT CAT ATA GAT TTT GGA CAC TTT TTG GAT CAC AAG AAG AAA AAA      2832
Leu Phe His Ile Asp Phe Gly His Phe Leu Asp His Lys Lys Lys Lys
930                 935                 940

TTT GGT TAT AAA CGA GAA CGT GTG CCA TTT GTT TTG ACA CAG GAT TTC      2880
Phe Gly Tyr Lys Arg Glu Arg Val Pro Phe Val Leu Thr Gln Asp Phe
945                 950                 955                 960

TTA ATA GTG ATT AGT AAA GGA GCC CAA GAA TGC ACA AAG ACA AGA GAA      2928
Leu Ile Val Ile Ser Lys Gly Ala Gln Glu Cys Thr Lys Thr Arg Glu
                965                 970                 975

TTT GAG AGG TTT CAG GAG ATG TGT TAC AAG GCT TAT CTA GCT ATT CGA      2976
Phe Glu Arg Phe Gln Glu Met Cys Tyr Lys Ala Tyr Leu Ala Ile Arg
            980                 985                 990

CAG CAT GCC AAT CTC TTC ATA AAT CTT TTC TCA ATG ATG CTT GGC TCT      3024
Gln His Ala Asn Leu Phe Ile Asn Leu Phe Ser Met Met Leu Gly Ser
                995                 1000                1005

GGA ATG CCA GAA CTA CAA TCT TTT GAT GAC ATT GCA TAC ATT CGA AAG      3072
Gly Met Pro Glu Leu Gln Ser Phe Asp Asp Ile Ala Tyr Ile Arg Lys
            1010                1015                1020

ACC CTA GCC TTA GAT AAA ACT GAG CAA GAG GCT TTG GAG TAT TTC ATG      3120
Thr Leu Ala Leu Asp Lys Thr Glu Gln Glu Ala Leu Glu Tyr Phe Met
```

```
1025              1030              1035              1040
AAA CAA ATG AAT GAT GCA CAT CAT GGT GGC TGG ACA ACA AAA ATG GAT          3168
Lys Gln Met Asn Asp Ala His His Gly Gly Trp Thr Thr Lys Met Asp
                    1045              1050              1055

TGG ATC TTC CAC ACA ATT AAA CAG CAT GCA TTG AAC TGAAAGATAA              3214
Trp Ile Phe His Thr Ile Lys Gln His Ala Leu Asn
            1060              1065

CTGAGAAAAT GAAAGCTCAC TCTGGACACT ACACTGCACT GTTAATAACT CTCAGCAGGC       3274

AAAGACCGAT TGCATAGGAA TTGCACAATC CATGAACAGC ATTAGATTTA CAGCAAGAAC       3334

AGAAATAAAA TACTATATAA TTTAAATAAT GTAAACGCAA ACAGGGTTTG ATAGCACTTA       3394

AACTAGTTCA TTTCAAAA                                                     3412

(2) INFORMATION FOR SEQ ID NO: 33:

(i) SEQUENCE CHARACTERISTICS:
        (A) LENGTH: 868 amino acids residues
        (B) TYPE: amino acid
        (C) STRANDEDNESS: single
        (D) TOPOLOGY: linear (xi) SEQUENCE DESCRIPTION: SEQ ID NO: 33:

Asn Ile Thr Phe Cys Val Ser Gln Asp Leu Asp Val Pro Leu Lys Val
1               5                   10                  15

Lys Ile Lys Ser Leu Glu Gly His Lys Pro Leu Leu Lys Pro Ser Gln
            20                  25                  30

Lys Ile Leu Asn Pro Glu Leu Met Leu Ile Gly Ser Asn Val Phe Pro
        35                  40                  45

Ser Ser Asp Leu Ile Val Ser Leu Gln Val Phe Asp Lys Glu Arg Asn
    50                  55                  60

Arg Asn Leu Thr Leu Pro Ile Tyr Thr Pro Tyr Ile Pro Phe Arg Asn
65                  70                  75                  80

Ser Arg Thr Trp Asp Tyr Trp Leu Thr Leu Pro Ile Arg Ile Lys Gln
                85                  90                  95

Leu Thr Phe Ser Ser His Leu Arg Ile Ile Leu Trp Glu Tyr Asn Gly
            100                 105                 110

Ser Lys Gln Ile Pro Phe Phe Asn Leu Glu Thr Ser Ile Phe Asn Leu
        115                 120                 125

Lys Asp Cys Thr Leu Lys Arg Gly Phe Glu Ser Leu Lys Phe Arg Tyr
    130                 135                 140

Asp Val Ile Asp His Cys Glu Val Val Thr Asp Asn Lys Asp Gln Glu
145                 150                 155                 160

Asn Leu Asn Lys Tyr Phe Gln Gly Glu Phe Thr Arg Leu Pro Trp Leu
                165                 170                 175

Asp Glu Ile Thr Ile Ser Lys Leu Arg Lys Gln Arg Glu Asn Arg Thr
            180                 185                 190

Trp Pro Gln Gly Thr Phe Val Leu Asn Leu Glu Phe Pro Met Leu Glu
        195                 200                 205

Leu Pro Val Val Phe Ile Glu Arg Glu Ile Met Asn Thr Gln Met Asn
    210                 215                 220

Ile Pro Thr Leu Lys Asn Asn Pro Gly Leu Ser Thr Asp Leu Arg Glu
225                 230                 235                 240

Pro Asn Arg Asn Asp Pro Gln Ile Lys Ile Ser Leu Gly Asp Lys Tyr
                245                 250                 255

His Ser Thr Leu Lys Phe Tyr Asp Pro Asp Gln Pro Asn Asn Asp Pro
            260                 265                 270
```

-continued

```
Ile Glu Glu Lys Tyr Arg Arg Leu Glu Arg Ala Ser Lys Asn Ala Asn
            275                 280                 285

Leu Asp Lys Gln Val Lys Pro Asp Ile Lys Lys Arg Asp Tyr Leu Asn
290                 295                 300

Lys Ile Ile Asn Tyr Pro Pro Gly Thr Lys Leu Thr Ala His Glu Lys
305                 310                 315                 320

Gly Ser Ile Trp Lys Tyr Arg Tyr Tyr Leu Met Asn Asn Lys Lys Ala
                325                 330                 335

Leu Thr Lys Leu Leu Gln Ser Thr Asn Leu Arg Glu Glu Ser Glu Arg
            340                 345                 350

Val Glu Val Leu Glu Leu Met Asp Ser Trp Ala Glu Ile Asp Ile Asp
        355                 360                 365

Asp Ala Leu Glu Leu Leu Gly Ser Thr Phe Lys Asn Leu Ser Val Arg
370                 375                 380

Ser Tyr Ala Val Asn Arg Leu Lys Lys Ala Ser Asp Lys Glu Leu Glu
385                 390                 395                 400

Leu Tyr Leu Leu Gln Leu Val Glu Ala Val Cys Phe Glu Asn Leu Ser
                405                 410                 415

Thr Phe Ser Asp Lys Ser Asn Ser Glu Phe Thr Ile Val Asp Ala Val
            420                 425                 430

Ser Ser Gln Lys Leu Ser Gly Asp Ser Met Leu Leu Ser Thr Ser His
        435                 440                 445

Ala Asn Gln Lys Leu Leu Lys Ser Ile Ser Ser Glu Ser Glu Thr Ser
450                 455                 460

Gly Thr Glu Ser Leu Pro Ile Val Ile Ser Pro Leu Ala Glu Phe Leu
465                 470                 475                 480

Ile Arg Arg Ala Leu Val Asn Pro Arg Leu Gly Ser Phe Phe Tyr Trp
                485                 490                 495

Tyr Leu Lys Ser Glu Ser Glu Asp Lys Pro Tyr Leu Asp Gln Ile Leu
            500                 505                 510

Ser Ser Phe Trp Ser Arg Leu Asp Lys Lys Ser Arg Asn Ile Leu Asn
        515                 520                 525

Asp Gln Val Arg Leu Ile Asn Val Leu Arg Glu Cys Cys Glu Thr Ile
530                 535                 540

Lys Arg Leu Lys Asp Thr Thr Ala Lys Lys Met Glu Leu Leu Val His
545                 550                 555                 560

Leu Leu Glu Thr Lys Val Arg Pro Leu Val Lys Val Arg Pro Ile Ala
                565                 570                 575

Leu Pro Leu Asp Pro Asp Val Leu Ile Cys Asp Val Cys Pro Glu Thr
            580                 585                 590

Ser Lys Val Phe Lys Ser Ser Leu Ser Pro Leu Lys Ile Thr Phe Lys
        595                 600                 605

Thr Thr Leu Asn Gln Pro Tyr His Leu Met Phe Lys Val Gly Asp Asp
610                 615                 620

Leu Arg Gln Asp Gln Leu Val Val Gln Ile Ile Ser Leu Met Asn Glu
625                 630                 635                 640

Leu Leu Lys Asn Glu Asn Val Asp Leu Lys Leu Thr Pro Tyr Lys Ile
                645                 650                 655

Leu Ala Thr Gly Pro Gln Glu Gly Ala Ile Glu Phe Ile Pro Asn Asp
            660                 665                 670

Thr Leu Ala Ser Ile Leu Ser Lys Tyr His Gly Ile Leu Gly Tyr Leu
        675                 680                 685
```

| Lys | Leu | His | Tyr | Pro | Asp | Glu | Asn | Ala | Thr | Leu | Gly | Val | Gln | Gly | Trp |
|   | 690 |   |   |   | 695 |   |   |   |   | 700 |   |   |   |   |   |

Val Leu Asp Asn Phe Val Lys Ser Cys Ala Gly Tyr Cys Val Ile Thr
705                     710                     715                     720

Tyr Ile Leu Gly Val Gly Asp Arg His Leu Asp Asn Leu Leu Val Thr
                    725                     730                     735

Pro Asp Gly His Phe Phe His Ala Asp Phe Gly Tyr Ile Leu Gly Gln
            740                     745                     750

Asp Pro Lys Pro Phe Pro Pro Leu Met Lys Leu Pro Pro Gln Ile Ile
        755                     760                     765

Glu Ala Phe Gly Gly Ala Glu Ser Ser Asn Tyr Asp Lys Phe Arg Ser
    770                     775                     780

Tyr Cys Phe Val Ala Tyr Ser Ile Leu Arg Arg Asn Ala Gly Leu Ile
785                     790                     795                     800

Leu Asn Leu Phe Glu Leu Met Lys Thr Ser Asn Ile Pro Asp Ile Arg
                    805                     810                     815

Ile Asp Pro Asn Gly Ala Ile Leu Arg Val Arg Glu Arg Phe Asn Leu
            820                     825                     830

Asn Met Ser Glu Glu Asp Ala Thr Val His Phe Gln Asn Leu Ile Asn
        835                     840                     845

Asp Ser Val Asn Ala Leu Leu Pro Ile Val Ile Asp His Leu His Asn
    850                     855                     860

Leu Ala Gln Tyr
865

(2) INFORMATION FOR SEQ ID NO: 34:

(i) SEQUENCE CHARACTERISTICS:
        (A) LENGTH: 3240 base pairs
        (B) TYPE: nucleic acid
        (C) STRANDEDNESS: single
        (D) TOPOLOGY: linear (xi) SEQUENCE DESCRIPTION: SEQ ID NO: 34:

```
ATGCCTCCAA GACCATCATC AGGTGAACTG TGGGGCATCC ACTTGATGCC CCCAAGAATC      60

CTAGTGGAAT GTTTACTACC AAATGGAATG ATAGTGACTT TAGAATGCCT CCGTGAGGCT     120

ACATTAGTAA CTATAAAGCA TGAACTATTT AAAGAAGCAA GAAAATACCC TCTCCATCAA     180

CTTCTTCAAG ATGAATCTTC TTACATTTTC GTAAGTGTTA CCCAAGAAGC AGAAAGGGAA     240

GAATTTTTTG ATGAAACAAG ACGACTTTGT GATCTTCGGC TTTTTCAACC ATTTTTAAAA     300

GTAATTGAAC CAGTAGGCAA CCGTGAAGAA AAGATCCTCA ATCGAGAAAT TGGTTTTGCT     360

ATCGGCATGC CAGTGTGCGA ATTTGATATG GTTAAAGATC CTGAAGTACA GGACTTCCGA     420

AGAAATATTC TTAATGTTTG TAAAGAAGCT GTGGATCTTA GGGATCTTAA TTCACCTCAT     480

AGTAGAGCAA TGTATGTCTA TCCGCCACAT GTAGAATCTT CACCAGAGCT GCCAAAGCAC     540

ATATATAATA AATTGGATAG AGGCCAAATA ATAGTGGTGA TTTGGGTAAT AGTTTCTCCA     600

AATAATGACA AGCAGAAGTA TACTCTGAAA ATCAACCATG ACTGTGTGCC AGAACAAGTA     660

ATTGCTGAAG CAATCAGGAA AAAAACTAGA AGTATGTTGC TATCATCTGA ACAATTAAAA     720

CTCTGTGTTT TAGAATATCA GGGCAAGTAC ATTTTAAAAG TGTGTGGATG TGATGAATAC     780

TTCCTAGAAA AATATCCTCT GAGTCAGTAT AAGTATATAA GAAGCTGTAT AATGCTTGGG     840

AGGATGCCCA ATTTGAAGAT GATGGCTAAA GAAAGCCTTT ATTCTCAACT GCCAATGGAC     900

TGTTTTACAA TGCCATCTTA TTCCAGACGC ATTTCCACAG CTACACCATA TATGAATGGA     960
```

-continued

```
GAAACATCTA CAAAATCCCT TTGGGTTATA AATAGAGCAC TCAGAATAAA AATTCTTTGT    1020

GCAACCTATG TGAATGTAAA TATTCGAGAC ATTGACAAGA TTTATGTTCG AACAGGTATC    1080

TACCATGGAG GAGAACCCTT ATGTGACAAT GTGAACACTC AAAGAGTACC TTGTTCCAAT    1140

CCCAGGTGGA ATGAATGGCT GAATTATGAT ATATACATTC CTGATCTTCC TCGTGCTGCT    1200

CGACTTTGCC TTTCCATTTG CTCTGTTAAA GGCCGAAAGG GTGCTAAAGA GGAACACTGT    1260

CCATTGGCAT GGGGAAATAT AAACTTGTTT GATTACACAG ACACTCTAGT ATCTGGAAAA    1320

ATGGCTTTGA ATCTTTGGCC AGTACCTCAT GGATTAGAAG ATTTGCTGAA CCCTATTGGT    1380

GTTACTGGAT CAAATCCAAA TAAAGAAACT CCATGCTTAG AGTTGGAGTT TGACTGGTTC    1440

AGCAGTGTGG TAAAGTTCCC AGATATGTCA GTGATTGAAG AGCATGCCAA TTGGTCTGTA    1500

TCCCGAGAAG CAGGATTTAG CTATTCCCAC GCAGGACTGA GTAACAGACT AGCTAGAGAC    1560

AATGAATTAA GGGAAAATGA CAAAGAACAG CTCAAAGCAA TTTCTACACG AGATCCTCTC    1620

TCTGAAATCA CTGAGCAGGA GAAAGATTTT CTATGGAGTC ACAGACACTA TTGTGTAACT    1680

ATCCCCGAAA TTCTACCCAA ATTGCTTCTG TCTGTTAAAT GGAATTCTAG AGATGAAGTA    1740

GCCCAGATGT ATTGCTTGGT AAAAGATTGG CCTCCAATCA AACCTGAACA GGCTATGGAA    1800

CTTCTGGACT GTAATTACCC AGATCCTATG GTTCGAGGTT TTGCTGTTCG GTGCTTGGAA    1860

AAATATTTAA CAGATGACAA ACTTTCTCAG TATTTAATTC AGCTAGTACA GGTCCTAAAA    1920

TATGAACAAT ATTTGGATAA CTTGCTTGTG AGATTTTTAC TGAAGAAAGC ATTGACTAAT    1980

CAAAGGATTG GGCACTTTTT CTTTTGGCAT TTAAAATCTG AGATGCACAA TAAAACAGTT    2040

AGCCAGAGGT TTGGCCTGCT TTTGGAGTCC TATTGTCGTG CATGTGGGAT GTATTTGAAG    2100

CACCTGAATA GGCAAGTCGA GGCAATGGAA AAGCTCATTA ACTTAACTGA CATTCTCAAA    2160

CAGGAGAGGA AGGATGAAAC ACAAAAGGTA CAGATGAAGT TTTTAGTTGA GCAAATGAGG    2220

CGACCAGATT TCATGGATGC CCTACAGGGC TTGCTGTCTC CTCTAAACCC TGCTCATCAA    2280

CTAGGAAACC TCAGGCTTAA AGAGTGTCGA ATTATGTCTT CTGCAAAAAG GCCACTGTGG    2340

TTGAATTGGG AGAACCCAGA CATCATGTCA GAGTTACTGT TTCAGAACAA TGAGATCATC    2400

TTTAAAAATG GGGATGATTT ACGGCAAGAT ATGCTAACAC TTCAAATTAT TCGTATTATG    2460

GAAAATATCT GGCAAAATCA AGGTCTTGAT CTTCGAATGT TACCTTATGG TTGTCTGTCA    2520

ATCGGTGACT GTGTGGGACT TATTGAGGTG GTGCGAAATT CTCACACTAT TATGCAAATT    2580

CAGTGCAAAG GCGGCTTGAA AGGTGCACTG CAGTTCAACA GCCACACACT ACATCAGTGG    2640

CTCAAAGACA AGAACAAAGG AGAAATATAT GATGCAGCCA TTGACCTGTT TACACGTTCA    2700

TGTGCTGGAT ACTGTGTAGC TACCTTCATT TTGGGAATTG GAGATCGTCA CAATAGTAAC    2760

ATCATGGTGA AAGACGATGG ACAACTGTTT CATATAGATT TTGGACACTT TTTGGATCAC    2820

AAGAAGAAAA AATTTGGTTA TAAACGAGAA CGTGTGCCAT TTGTTTTGAC ACAGGATTTC    2880

TTAATAGTGA TTAGTAAAGG AGCCCAAGAA TGCACAAAGA CAAGAGAATT TGAGAGGTTT    2940

CAGGAGATGT GTTACAAGGC TTATCTAGCT ATTCGACAGC ATGCCAATCT CTTCATAAAT    3000

CTTTTCTCAA TGATGCTTGG CTCTGGAATG CCAGAACTAC AATCTTTTGA TGACATTGCA    3060

TACATTCGAA AGACCCTAGC CTTAGATAAA ACTGAGCAAG AGGCTTTGGA GTATTTCATG    3120

AAACAAATGA ATGATGCACA TCATGGTGGC TGGACAACAA AAATGGATTG GATCTTCCAC    3180

ACAATTAAAC AGCATGCATT GAACTGAAAG ATAACTGAGA AAATGAAAGC TCACTCTGGA    3240
```

(2) INFORMATION FOR SEQ ID NO: 35:

(i) SEQUENCE CHARACTERISTICS:
    (A) LENGTH: 3207 base pairs
    (B) TYPE: nucleic acid
    (C) STRANDEDNESS: single
    (D) TOPOLOGY: linear (xi) SEQUENCE DESCRIPTION: SEQ ID NO: 35:

| | | | | | |
|---|---|---|---|---|---|
| ATGCCTCCAA | GACCATCATC | AGGTGAACTG | TGGGGCATCC | ACTTGATGCC | CCCAAGAATC | 60 |
| CTAGTAGAAT | GTTTACTACC | AAATGGGATG | ATAGTGACTT | TAGAATGCCT | CCGTGAGGCT | 120 |
| ACGTTAATAA | CGATAAAGCA | TGAACTATTT | AAAGAAGCAA | GAAAATACCC | TCTCCATCAA | 180 |
| CTTCTTCAAG | ATGAATCTTC | TTACATTTTC | GTAAGTGTTA | CCCAAGAAGC | AGAAAGGGAA | 240 |
| GAATTTTTTG | ATGAAACAAG | ACGACTTTGT | GACCTTCGGC | TTTTTCAACC | CTTTTTAAAA | 300 |
| GTAATTGAAC | CAGTAGGCAA | CCGTGAAGAA | AAGATCCTCA | ATCGAGAAAT | TGGTTTTGCT | 360 |
| ATCGGCATGC | CAGTGTGTGA | ATTCGATATG | GTTAAAGATC | CAGAAGTACA | GGACTTCCGA | 420 |
| AGAAATATTC | TCAATGTTTG | TAAAGAAGCT | GTGGATCTTA | GGGATCTTAA | TTCACCTCAT | 480 |
| AGTAGAGCAA | TGTATGTTTA | TCCTCCAAAT | GTAGAATCTT | CACCGAGAACT | GCCAAAGCAC | 540 |
| ATATATAATA | AATTGGATAA | AGGGCAAATA | ATAGTGGTGA | TTTGGGTAAT | AGTTTCTCCA | 600 |
| AATAATGACA | AACAGAAGTA | TACTCTGAAA | ATCAACCATG | ACTGTGTGCC | AGAACAAGTA | 660 |
| ATTGCTGAAG | CAATCAGGAA | AAAAACTCGA | AGTATGTTGC | TATCATCTGA | ACAACTAAAA | 720 |
| CTCTGTGTTT | TAGAATATCA | GGGCAAGTAT | ATTTTAAAAG | TGTGTGGATG | TGATGAATAC | 780 |
| TTCCTAGAAA | AATATCCTCT | GAGTCAGTAT | AAGTATATAA | GAAGCTGTAT | AATGCTTGGG | 840 |
| AGGATGCCCA | ATTTGATGCT | GATGGCTAAA | GAAAGCCTCT | ATTCTCAACT | GCCAATGGAC | 900 |
| TGTTTTACAA | TGCCATCATA | TTCCAGACGC | ATCTCCACAG | CTACGCCATA | TATGAATGGA | 960 |
| GAAACATCTA | CAAAATCCCT | TGGGTTATA  | AATAGTGCAC | TCAGAATAAA | AATTCTTTGT | 1020 |
| GCAACCTATG | TGAATGTAAA | TATTCGAGAC | ATTGACAAGA | TTTATGTTCG | AACAGGTATC | 1080 |
| TACCATGGAG | GAGAACCCTT | ATGTGATAAT | GTGAACACTC | AAAGAGTACC | TTGTTCCAAT | 1140 |
| CCCAGGTGGA | ATGAATGGCT | GAATTACGAT | ATATACATTC | CTGATCTTCC | TCGTGCTGCT | 1200 |
| CGACTTTGCC | TTTCCATTTG | TTCTGTTAAA | GGCCGAAAGG | GTGCTAAAGA | GGAACACTGT | 1260 |
| CCATTGGCCT | GGGGAAATAT | AAACTTGTTT | GATTACACAG | ATACTCTAGT | ATCTGGAAAA | 1320 |
| ATGGCTTTGA | ATCTTTGGCC | AGTACCTCAT | GGACTAGAAG | ATTTGCTGAA | CCCTATTGGT | 1380 |
| GTTACTGGAT | CAAATCCAAA | TAAAGAAACT | CCATGTTTAG | AGTTGGAGTT | TGACTGGTTC | 1440 |
| AGCAGTGTGG | TAAAGTTTCC | AGATATGTCA | GTGATTGAAG | AGCATGCCAA | TTGGTCTGTA | 1500 |
| TCCCGTGAAG | CAGGATTTAG | TTATTCCCAT | GCAGGACTGA | GTAACAGACT | AGCTAGAGAC | 1560 |
| AATGAATTAA | GAGAAAATGA | TAAAGAACAG | CTCCGAGCAA | TTTGTACACG | AGATCCTCTA | 1620 |
| TCTGAAATCA | CTGAGCAAGA | GAAAGATTTT | CTGTGGAGCC | ACAGACACTA | TTGTGTAACT | 1680 |
| ATCCCCGAAA | TTCTACCCAA | ATTGCTTCTG | TCTGTTAAAT | GGAACTCTAG | AGATGAAGTA | 1740 |
| GCTCAGATGT | ACTGCTTGGT | AAAAGATTGG | CCTCCAATCA | AGCCTGAACA | GGCTATGGAG | 1800 |
| CTTCTGGACT | GCAATTACCC | AGATCCTATG | GTTCGAGGTT | TTGCTGTTCG | GTGCTTAGAA | 1860 |
| AAATATTTAA | CAGATGACAA | ACTTTCTCAG | TACCTAATTC | AGCTAGTACA | GGTACTAAAA | 1920 |
| TATGAACAGT | ATTTGGATAA | CCTGCTTGTG | AGATTTTTAC | TCAAAAAAGC | GTTAACTAAT | 1980 |
| CAAAGGATCG | GTCACTTTTT | CTTTTGGCAT | TTAAAATCTG | AGATGCACAA | TAAAACAGTT | 2040 |
| AGTCAGAGGT | TTGGCCTGCT | TTTGGAGTCC | TATTGCCGTG | CATGTGGGAT | GTATCTGAAG | 2100 |
| CACCTTAATA | GGCAAGTTGA | GGCTATGGAA | AAGCTCATTA | ACTTGACTGA | CATTCTCAAA | 2160 |

-continued

```
CAAGAGAAGA AGGATGAAAC ACAAAAGGTA CAGATGAAGT TTTTAGTTGA GCAAATGCGG      2220

CGACCAGATT TCATGGATGC TCTCCAGGGC TTTCTGTCTC CTCTAAACCC TGCTCATCAG      2280

CTGGGAAATC TCAGGCTTGA AGAGTGTCGA ATTATGTCTT CTGCAAAAAG GCCACTGTGG      2340

TTGAATTGGG AGAACCCAGA CATCATGTCA GAATTACTCT TTCAGAACAA TGAGATCATC      2400

TTTAAAAATG GGGATGATTT ACGGCAAGAT ATGCTAACCC TTCAGATTAT TCGCATTATG      2460

GAAAATATCT GGCAAAATCA AGGTCTTGAT CTTCGAATGT TACCTTATGG ATGTCTGTCA      2520

ATCGGTGACT GTGTGGGACT TATCGAGGTG GTGAGAAATT CTCACACTAT AATGCAGATT      2580

CAGTGTAAAG GAGGCCTGAA AGGTGCACTG CAGTTTAACA GCCACACACT CCATCAGTGG      2640

CTCAAAGACA AGAACAAGGG GGAAATATAT GATGCGGCCA TCGATTTGTT TACACGATCA      2700

TGTGCTGGAT ATTGTGTTGC CACCTTCATT TTGGGAATTG GAGATCGTCA CAATAGTAAT      2760

ATCATGGTTA AAGATGATGG ACAACTGTTT CATATAGATT TTGGACACTT TTTGGATCAC      2820

AAGAAGAAAA AATTTGGTTA TAAACGAGAG CGCGTGCCGT TTGTTTTGAC ACAAGATTTC      2880

TTAATAGTGA TTAGTAAAGG AGCCCAAGAA TGCACAAAGA CAAGAGAATT TGAGAGGTTT      2940

CAGGAGATGT GTTACAAGGC TTATCTAGCT ATTCGGCAGC ATGCCAATCT CTTCATAAAT      3000

CTTTTCTCAA TGATGCTTGG CTCTGGAATG CCAGAACTGC AATCTTTTGA TGATATTGCA      3060

TACATTCGAA AGACCCTAGC TTTAGATAAA ACTGAGCAAG AGGCTTTGGA GTATTTCATG      3120

AAACAAATGA ATGATGCACA CCATGGTGGC TGGACAACAA AAATGGATTG GATCTTCCAC      3180

ACAATTAAGC AGCATGCTTT GAACTGA                                         3207
```

(2) INFORMATION FOR SEQ ID NO: 36:

(i) SEQUENCE CHARACTERISTICS:
        (A) LENGTH: 1080 amino acids
        (B) TYPE: amino acid
        (C) STRANDEDNESS: single
        (D) TOPOLOGY: linear (xi) SEQUENCE DESCRIPTION: SEQ ID NO: 36:

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro His Val Glu Ser Ser Pro Glu
```

```
                165                 170                 175
Leu Pro Lys His Ile Tyr Asn Lys Leu Asp Arg Gly Gln Ile Ile Val
            180                 185                 190

Val Ile Trp Val Ile Val Ser Pro Asn Asp Lys Gln Lys Tyr Thr
        195                 200                 205

Leu Lys Ile Asn His Asp Cys Val Pro Glu Gln Val Ile Ala Glu Ala
            210                 215                 220

Ile Arg Lys Lys Thr Arg Ser Met Leu Ser Ser Glu Gln Leu Lys
225                 230                 235                 240

Leu Cys Val Leu Glu Tyr Gln Gly Lys Tyr Ile Leu Lys Val Cys Gly
            245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Lys Met Met
            275                 280                 285

Ala Lys Glu Ser Leu Tyr Ser Gln Leu Pro Met Asp Cys Phe Thr Met
            290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Arg Ala Leu Arg Ile
                325                 330                 335

Lys Ile Leu Cys Ala Thr Tyr Val Asn Leu Asn Ile Arg Asp Ile Asp
                340                 345                 350

Lys Ile Tyr Val Arg Thr Gly Ile Tyr His Gly Gly Glu Pro Leu Cys
                355                 360                 365

Asp Asn Val Asn Thr Gln Arg Val Pro Cys Ser Asn Pro Arg Trp Asn
            370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
            450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
            515                 520                 525

Glu Gln Leu Lys Ala Ile Ser Thr Arg Asp Pro Leu Ser Glu Ile Thr
            530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590
```

```
Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Arg Lys Asp Glu Thr Gln Lys Val Gln Met Lys Phe Leu Val
                725                 730                 735

Glu Gln Met Arg Arg Pro Asp Phe Met Asp Ala Leu Gln Gly Leu Leu
            740                 745                 750

Ser Pro Leu Asn Pro Ala His Gln Leu Gly Asn Leu Arg Leu Lys Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn Leu Phe Ser Met Met Leu Gly Ser
        995                 1000                1005
```

```
Gly Met Pro Glu Leu Gln Ser Phe Asp Asp Ile Ala Tyr Ile Arg Lys
    1010                1015                1020

Thr Leu Ala Leu Asp Lys Thr Glu Gln Glu Ala Leu Glu Tyr Phe Met
1025                1030                1035                1040

Lys Gln Met Asn Asp Ala His His Gly Gly Trp Thr Thr Lys Met Asp
                1045                1050                1055

Trp Ile Phe His Thr Ile Lys Gln His Ala Leu Asn Xaa Lys Ile Thr
            1060                1065                1070

Glu Lys Met Lys Ala His Ser Gly
        1075                1080

(2) INFORMATION FOR SEQ ID NO: 37:

(i) SEQUENCE CHARACTERISTICS:
        (A) LENGTH: 1069 amino acids
        (B) TYPE: amino acid
        (C) STRANDEDNESS: single
        (D) TOPOLOGY: linear (xi) SEQUENCE DESCRIPTION: SEQ ID NO: 37:

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285
```

```
Ala Lys Glu Ser Leu Tyr Ser Gln Leu Pro Met Asp Cys Phe Thr Met
    290                 295                 300
Pro Ser Tyr Ser Arg Arg Ile Ser Thr Ala Thr Pro Tyr Met Asn Gly
305                 310                 315                 320
Glu Thr Ser Thr Lys Ser Leu Trp Val Ile Asn Ser Ala Leu Arg Ile
                325                 330                 335
Lys Ile Leu Cys Ala Thr Tyr Val Asn Val Asn Ile Arg Asp Ile Asp
                340                 345                 350
Lys Ile Tyr Val Arg Thr Gly Ile Tyr His Gly Gly Glu Pro Leu Cys
                355                 360                 365
Asp Asn Val Asn Thr Gln Arg Val Pro Cys Ser Asn Pro Arg Trp Asn
370                 375                 380
Glu Trp Leu Asn Tyr Asp Ile Tyr Ile Pro Asp Leu Pro Arg Ala Ala
385                 390                 395                 400
Arg Leu Cys Leu Ser Ile Cys Ser Val Lys Gly Arg Lys Gly Ala Lys
                405                 410                 415
Glu Glu His Cys Pro Leu Ala Trp Gly Asn Ile Asn Leu Phe Asp Tyr
                420                 425                 430
Thr Asp Thr Leu Val Ser Gly Lys Met Ala Leu Asn Leu Trp Pro Val
                435                 440                 445
Pro His Gly Leu Glu Asp Leu Leu Asn Pro Ile Gly Val Thr Gly Ser
        450                 455                 460
Asn Pro Asn Lys Glu Thr Pro Cys Leu Glu Leu Glu Phe Asp Trp Phe
465                 470                 475                 480
Ser Ser Val Val Lys Phe Pro Asp Met Ser Val Ile Glu Glu His Ala
                485                 490                 495
Asn Trp Ser Val Ser Arg Glu Ala Gly Phe Ser Tyr Ser His Ala Gly
                500                 505                 510
Leu Ser Asn Arg Leu Ala Arg Asp Asn Glu Leu Arg Glu Asn Asp Lys
                515                 520                 525
Glu Gln Leu Arg Ala Ile Cys Thr Arg Asp Pro Leu Ser Glu Ile Thr
        530                 535                 540
Glu Gln Glu Lys Asp Phe Leu Trp Ser His Arg His Tyr Cys Val Thr
545                 550                 555                 560
Ile Pro Glu Ile Leu Pro Lys Leu Leu Leu Ser Val Lys Trp Asn Ser
                565                 570                 575
Arg Asp Glu Val Ala Gln Met Tyr Cys Leu Val Lys Asp Trp Pro Pro
                580                 585                 590
Ile Lys Pro Glu Gln Ala Met Glu Leu Leu Asp Cys Asn Tyr Pro Asp
        595                 600                 605
Pro Met Val Arg Gly Phe Ala Val Arg Cys Leu Glu Lys Tyr Leu Thr
        610                 615                 620
Asp Asp Lys Leu Ser Gln Tyr Leu Ile Gln Leu Val Gln Val Leu Lys
625                 630                 635                 640
Tyr Glu Gln Tyr Leu Asp Asn Leu Leu Val Arg Phe Leu Leu Lys Lys
                645                 650                 655
Ala Leu Thr Asn Gln Arg Ile Gly His Phe Phe Phe Trp His Leu Lys
                660                 665                 670
Ser Glu Met His Asn Lys Thr Val Ser Gln Arg Phe Gly Leu Leu Leu
                675                 680                 685
Glu Ser Tyr Cys Arg Ala Cys Gly Met Tyr Leu Lys His Leu Asn Arg
        690                 695                 700
```

```
Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
                740                 745                 750

Ser Pro Leu Asn Pro Ala His Gln Leu Gly Asn Leu Arg Leu Glu Glu
                755                 760                 765

Cys Arg Ile Met Ser Ser Ala Lys Arg Pro Leu Trp Leu Asn Trp Glu
770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
                820                 825                 830

Met Leu Pro Tyr Gly Cys Leu Ser Ile Gly Asp Cys Val Gly Leu Ile
                835                 840                 845

Glu Val Val Arg Asn Ser His Thr Ile Met Gln Ile Gln Cys Lys Gly
850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
                900                 905                 910

Ile Gly Asp Arg His Asn Ser Asn Ile Met Val Lys Asp Asp Gly Gln
                915                 920                 925

Leu Phe His Ile Asp Phe Gly His Phe Leu Asp His Lys Lys Lys Lys
                930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
                980                 985                 990

Gln His Ala Asn Leu Phe Ile Asn Leu Phe Ser Met Met Leu Gly Ser
                995                 1000                1005

Gly Met Pro Glu Leu Gln Ser Phe Asp Asp Ile Ala Tyr Ile Arg Lys
            1010                1015                1020

Thr Leu Ala Leu Asp Lys Thr Glu Gln Glu Ala Leu Glu Tyr Phe Met
1025                1030                1035                1040

Lys Gln Met Asn Asp Ala His His Gly Gly Trp Thr Thr Lys Met Asp
                1045                1050                1055

Trp Ile Phe His Thr Ile Lys Gln His Ala Leu Asn Xaa
            1060                1065
```

(2) INFORMATION FOR SEQ ID NO: 38:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ix) FEATURE:

```
            (A) NAME/KEY: CDS
            (B) LOCATION: 1..381

(xi) SEQUENCE DESCRIPTION: SEQ ID NO: 38:

GGA GAC GAC TTG CGA CAG GAT CAA CTT ATT CTT CAA ATC ATT TCA CTC      48
Gly Asp Asp Leu Arg Gln Asp Gln Leu Ile Leu Gln Ile Ile Ser Leu
 1               5                  10                  15

ATG GAC AAG CTG TTA CGG AAA GAA AAT CTG GAC TTG AAA TTG ACA CCT      96
Met Asp Lys Leu Leu Arg Lys Glu Asn Leu Asp Leu Lys Leu Thr Pro
             20                  25                  30

TAT AAG GTG TTA GCC ACC AGT ACA AAA CAT GGC TTC ATG CAG TTT ATC     144
Tyr Lys Val Leu Ala Thr Ser Thr Lys His Gly Phe Met Gln Phe Ile
         35                  40                  45

CAG TCA GTT CCT GTG GCT GAA GTT CTT GAT ACA GAG GGA AGC ATT CAG     192
Gln Ser Val Pro Val Ala Glu Val Leu Asp Thr Glu Gly Ser Ile Gln
     50                  55                  60

AAC TTT TTT AGA AAA TAT GCA CCA AGT GAG AAT GGG CCA AAT GGG ATT     240
Asn Phe Phe Arg Lys Tyr Ala Pro Ser Glu Asn Gly Pro Asn Gly Ile
 65                  70                  75                  80

AGT GCT GAG GTC ATG GAC ACT TAC GTT AAA AGC TGT GCT GGA TAT TGC     288
Ser Ala Glu Val Met Asp Thr Tyr Val Lys Ser Cys Ala Gly Tyr Cys
                 85                  90                  95

GTG ATC ACC TAT ATA CTT GGA GTT GGA GAC AGG CAC CTG GAT AAC CTT     336
Val Ile Thr Tyr Ile Leu Gly Val Gly Asp Arg His Leu Asp Asn Leu
            100                 105                 110

TTG CTA ACC AAA ACA GGC AAA CTC TTC CAC ATC GAT TTC GGC CAC         381
Leu Leu Thr Lys Thr Gly Lys Leu Phe His Ile Asp Phe Gly His
        115                 120                 125

(2) INFORMATION FOR SEQ ID NO: 39:

(i) SEQUENCE CHARACTERISTICS:
          (A) LENGTH: 127 amino acids
          (B) TYPE: amino acid
          (D) TOPOLOGY: linear (ii) MOLECULE TYPE: protein (xi) SEQUENCE DESCRIPTION: SEQ ID NO: 39:

Gly Asp Asp Leu Arg Gln Asp Gln Leu Ile Leu Gln Ile Ile Ser Leu
 1               5                  10                  15

Met Asp Lys Leu Leu Arg Lys Glu Asn Leu Asp Leu Lys Leu Thr Pro
             20                  25                  30

Tyr Lys Val Leu Ala Thr Ser Thr Lys His Gly Phe Met Gln Phe Ile
         35                  40                  45

Gln Ser Val Pro Val Ala Glu Val Leu Asp Thr Glu Gly Ser Ile Gln
     50                  55                  60

Asn Phe Phe Arg Lys Tyr Ala Pro Ser Glu Asn Gly Pro Asn Gly Ile
 65                  70                  75                  80

Ser Ala Glu Val Met Asp Thr Tyr Val Lys Ser Cys Ala Gly Tyr Cys
                 85                  90                  95

Val Ile Thr Tyr Ile Leu Gly Val Gly Asp Arg His Leu Asp Asn Leu
            100                 105                 110

Leu Leu Thr Lys Thr Gly Lys Leu Phe His Ile Asp Phe Gly His
        115                 120                 125

(2) INFORMATION FOR SEQ ID NO: 40:

(i) SEQUENCE CHARACTERISTICS:
          (A) LENGTH: 393 base pairs
          (B) TYPE: nucleic acid
```

(C) STRANDEDNESS: single
        (D) TOPOLOGY: linear (ix) FEATURE:
        (A) NAME/KEY: CDS
        (B) LOCATION: 1..393

(xi) SEQUENCE DESCRIPTION: SEQ ID NO: 40:

GGG GAT GAC TTA CGG CAG GAC ATG CTA ACG CTG CAG ATG ATT CGC ATC        48
Gly Asp Asp Leu Arg Gln Asp Met Leu Thr Leu Gln Met Ile Arg Ile
 1               5                  10                  15

ATG AGC AAG ATC TGG GTC CAG GAG GGG CTG GAC ATG CGC ATG GTC ATC        96
Met Ser Lys Ile Trp Val Gln Glu Gly Leu Asp Met Arg Met Val Ile
                 20                  25                  30

TTC CGC TGC TTC TCC ACC GGC CGG GGC AGA GGG ATG GTG GAG ATG ATC       144
Phe Arg Cys Phe Ser Thr Gly Arg Gly Arg Gly Met Val Glu Met Ile
             35                  40                  45

CCT AAT GCT GAG ACC CTG CGT AAG ATC CAG GTG GAG CAT GGG GTG ACC       192
Pro Asn Ala Glu Thr Leu Arg Lys Ile Gln Val Glu His Gly Val Thr
         50                  55                  60

GGC TCG TTC AAG GAC CGG CCC CTG GCA GAC CGG CTG CAG AAA CAC AAC       240
Gly Ser Phe Lys Asp Arg Pro Leu Ala Asp Arg Leu Gln Lys His Asn
 65                  70                  75                  80

CCT GGG GAG GAC GAG TAT GAG AAG GCT GTG GAG AAC TTT ATC TAC TCC       288
Pro Gly Glu Asp Glu Tyr Glu Lys Ala Val Glu Asn Phe Ile Tyr Ser
                 85                  90                  95

TGC GCT GGC TGC TGC GTG GCC ACG TAC GTC TTG GGC ATC TGT GAC CGA       336
Cys Ala Gly Cys Cys Val Ala Thr Tyr Val Leu Gly Ile Cys Asp Arg
             100                 105                 110

CAT AAT GAC AAC ATC ATG CTG AAG ACC ACT GGT CAC ATG TTC CAC ATC       384
His Asn Asp Asn Ile Met Leu Lys Thr Thr Gly His Met Phe His Ile
         115                 120                 125

GAC TTC GGC                                                           393
Asp Phe Gly
    130

(2) INFORMATION FOR SEQ ID NO: 41:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO: 41:

Gly Asp Asp Leu Arg Gln Asp Met Leu Thr Leu Gln Met Ile Arg Ile
 1               5                  10                  15

Met Ser Lys Ile Trp Val Gln Glu Gly Leu Asp Met Arg Met Val Ile
                 20                  25                  30

Phe Arg Cys Phe Ser Thr Gly Arg Gly Arg Gly Met Val Glu Met Ile
             35                  40                  45

Pro Asn Ala Glu Thr Leu Arg Lys Ile Gln Val Glu His Gly Val Thr
         50                  55                  60

Gly Ser Phe Lys Asp Arg Pro Leu Ala Asp Arg Leu Gln Lys His Asn
 65                  70                  75                  80

Pro Gly Glu Asp Glu Tyr Glu Lys Ala Val Glu Asn Phe Ile Tyr Ser
                 85                  90                  95

Cys Ala Gly Cys Cys Val Ala Thr Tyr Val Leu Gly Ile Cys Asp Arg
             100                 105                 110

His Asn Asp Asn Ile Met Leu Lys Thr Thr Gly His Met Phe His Ile

Asp Phe Gly
    130

(2) INFORMATION FOR SEQ ID NO: 42:

(i) SEQUENCE CHARACTERISTICS:
        (A) LENGTH: 66 amino acids
        (B) TYPE: amino acid
        (C) STRANDEDNESS: single
        (D) TOPOLOGY: linear (xi) SEQUENCE DESCRIPTION: SEQ ID NO: 42:

Gly Asp Asp Leu Arg Gln Asp Gln Leu Val Val Gln Ile Ile Ser Leu
1               5                   10                  15

Met Asn Glu Leu Leu Lys Asn Glu Asn Val Asp Leu Lys Leu Thr Pro
            20                  25                  30

Tyr Lys Ile Leu Ala Thr Gly Pro Gln Glu Gly Ala Ile Glu Phe Ile
            35                  40                  45

Pro Asn Asp Thr Leu Ala Ser Ile Leu Ser Lys Tyr His Gly Ile Leu
        50                  55                  60

Gly Tyr
65

(2) INFORMATION FOR SEQ ID NO: 43:

(i) SEQUENCE CHARACTERISTICS:
        (A) LENGTH: 60 amino acids
        (B) TYPE: amino acid
        (C) STRANDEDNESS: single
        (D) TOPOLOGY: linear (xi) SEQUENCE DESCRIPTION: SEQ ID NO: 43:

Leu Lys Leu His Tyr Pro Asp Glu Asn Ala Thr Leu Gly Val Gln Gly
1               5                   10                  15

Trp Val Leu Asp Asn Phe Val Lys Ser Cys Ala Gly Tyr Cys Val Ile
            20                  25                  30

Thr Tyr Ile Leu Gly Val Gly Asp Arg His Leu Asp Asn Leu Leu Val
            35                  40                  45

Thr Pro Asp Gly His Phe Phe His Ala Asp Phe Gly
        50                  55                  60

(2) INFORMATION FOR SEQ ID NO: 44:

(i) SEQUENCE CHARACTERISTICS:
        (A) LENGTH: 66 amino acids
        (B) TYPE: amino acid
        (C) STRANDEDNESS: single
        (D) TOPOLOGY: linear (xi) SEQUENCE DESCRIPTION: SEQ ID NO: 44:

Gly Asp Asp Leu Arg Gln Asp Gln Leu Ile Leu Gln Ile Ile Ser Leu
1               5                   10                  15

Met Asp Lys Leu Leu Arg Lys Glu Asn Leu Asp Leu Lys Leu Thr Pro
            20                  25                  30

Tyr Lys Val Leu Ala Thr Ser Thr Lys His Gly Phe Met Gln Phe Ile
            35                  40                  45

Gln Ser Val Pro Val Ala Glu Val Leu Asp Thr Glu Gly Ser Ile Gln
        50                  55                  60

Asn Phe
65

(2) INFORMATION FOR SEQ ID NO: 45:

(i) SEQUENCE CHARACTERISTICS:
       (A) LENGTH: 60 amino acids
       (B) TYPE: amino acid
       (C) STRANDEDNESS: single
       (D) TOPOLOGY: linear (xi) SEQUENCE DESCRIPTION: SEQ ID NO: 45:

Phe Arg Lys Tyr Ala Pro Ser Glu Asn Gly Pro Asn Gly Ile Ser Ala
1               5                   10                  15

Glu Val Met Asp Thr Tyr Val Lys Ser Cys Ala Gly Tyr Cys Val Ile
            20                  25                  30

Thr Tyr Ile Leu Gly Val Gly Asp Arg His Leu Asp Asn Leu Leu Leu
        35                  40                  45

Thr Lys Thr Gly Lys Leu Phe His Ile Asp Phe Gly
    50                  55                  60

(2) INFORMATION FOR SEQ ID NO: 46:

(i) SEQUENCE CHARACTERISTICS:
       (A) LENGTH: 85 amino acids
       (B) TYPE: amino acid
       (C) STRANDEDNESS: single
       (D) TOPOLOGY: linear (xi) SEQUENCE DESCRIPTION: SEQ ID NO: 46:

Gly Asp Asp Leu Arg Gln Asp Met Leu Thr Leu Gln Ile Ile Arg Ile
1               5                   10                  15

Met Glu Asn Ile Trp Gln Asn Gln Gly Leu Asp Leu Arg Met Leu Pro
            20                  25                  30

Tyr Gly Cys Leu Ser Ile Gly Asp Cys Val Gly Leu Ile Glu Val Val
        35                  40                  45

Arg Asn Ser His Thr Ile Met Gln Ile Gln Cys Lys Gly Gly Leu Lys
    50                  55                  60

Gly Ala Leu Gln Phe Asn Ser His Thr Leu His Gln Trp Leu Lys Asp
65                  70                  75                  80

Lys Asn Lys Gly Glu
            85

(2) INFORMATION FOR SEQ ID NO: 47:

(i) SEQUENCE CHARACTERISTICS:
       (A) LENGTH: 47 amino acids
       (B) TYPE: amino acid
       (C) STRANDEDNESS: single
       (D) TOPOLOGY: linear (xi) SEQUENCE DESCRIPTION: SEQ ID NO: 47:

Ile Tyr Asp Ala Ala Ile Asp Leu Phe Thr Arg Ser Cys Ala Gly Tyr
1               5                   10                  15

Cys Val Ala Thr Phe Ile Leu Gly Ile Gly Asp Arg His Asn Ser Asn
            20                  25                  30

Ile Met Val Lys Asp Asp Gly Gln Leu Phe His Ile Asp Phe Gly
35                  40                  45

(2) INFORMATION FOR SEQ ID NO: 48:

(i) SEQUENCE CHARACTERISTICS:
       (A) LENGTH: 66 amino acids
       (B) TYPE: amino acid

```
            (C) STRANDEDNESS: single
            (D) TOPOLOGY: linear (xi) SEQUENCE DESCRIPTION: SEQ ID NO: 48:

Gly Asp Asp Leu Arg Gln Asp Met Leu Thr Leu Gln Met Ile Arg Ile
1               5                   10                  15

Met Ser Lys Ile Trp Val Gln Glu Gly Leu Asp Met Arg Met Val Ile
            20                  25                  30

Phe Arg Cys Phe Ser Thr Gly Arg Gly Arg Gly Met Val Glu Met Ile
            35                  40                  45

Pro Asn Ala Glu Thr Leu Arg Lys Ile Gln Val Glu His Gly Val Thr
    50                  55                  60

Gly Ser
65

(2) INFORMATION FOR SEQ ID NO: 49:

(i) SEQUENCE CHARACTERISTICS:
        (A) LENGTH: 65 amino acids
        (B) TYPE: amino acid
        (C) STRANDEDNESS: single
        (D) TOPOLOGY: linear (xi) SEQUENCE DESCRIPTION: SEQ ID NO: 49:

Phe Lys Asp Arg Pro Leu Ala Asp Arg Leu Gln Lys His Asn Pro Gly
1               5                   10                  15

Glu Asp Glu Tyr Glu Lys Ala Val Glu Asn Phe Ile Tyr Ser Cys Ala
            20                  25                  30

Gly Cys Cys Val Ala Thr Tyr Val Leu Gly Ile Cys Asp Arg His Asn
            35                  40                  45

Asp Asn Ile Met Leu Lys Thr Thr Gly His Met Phe His Ile Asp Phe
    50                  55                  60

Gly
65

(2) INFORMATION FOR SEQ ID NO: 50:

(i) SEQUENCE CHARACTERISTICS:
        (A) LENGTH: 62 amino acids
        (B) TYPE: amino acid
        (C) STRANDEDNESS: single
        (D) TOPOLOGY: linear (xi) SEQUENCE DESCRIPTION: SEQ ID NO: 50:

Gly Asp Asp Leu Arg Gln Asp Leu Leu Gln Ile Ile Met Glu Leu Asp
1               5                   10                  15

Leu Pro Tyr Leu Thr Gly Gly Ile Glu Ile Asn Gly Ile Gly Leu Asn
            20                  25                  30

Ile Asp Phe Val Ser Cys Ala Gly Tyr Cys Val Thr Tyr Ile Leu Gly
            35                  40                  45

Gly Asp Arg His Asp Asn Gly Leu Phe His Ile Asp Phe Gly
    50                  55                  60
```